US011779579B2

(12) United States Patent
Tabuteau

(10) Patent No.: US 11,779,579 B2
(45) Date of Patent: *Oct. 10, 2023

(54) BUPROPION AS A MODULATOR OF DRUG ACTIVITY

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,147

(22) Filed: Sep. 1, 2022

(65) Prior Publication Data

US 2023/0099206 A1  Mar. 30, 2023

Related U.S. Application Data

(63) Continuation of application No. 17/547,050, filed on Dec. 9, 2021, now Pat. No. 11,433,067, which is a continuation-in-part of application No. 17/066,310, filed on Oct. 8, 2020, now Pat. No. 11,229,640, which is a continuation-in-part of application No. 16/822,697, filed on Mar. 18, 2020, now Pat. No. 11,090,300, and a continuation-in-part of application No. 16/817,119, filed on Mar. 12, 2020, now Pat. No. 10,813,924, said application No. 16/822,697 is a continuation-in-part of application No. 16/359,958, filed on Mar. 20, 2019, now Pat. No. 10,881,657, said application No. 16/817,119 is a continuation-in-part of application No. 16/359,996, filed on Mar. 20, 2019, now Pat. No. 10,688,066, said application No. 16/359,958 is a continuation-in-part of application No. 15/821,563, filed on Nov. 22, 2017, now Pat. No. 10,512,643, which is a continuation-in-part of application No. 15/645,939, filed on Jul. 10, 2017, now Pat. No. 9,867,819, which is a continuation-in-part of application No. 15/263,138, filed on Sep. 12, 2016, now Pat. No. 9,700,553, which is a continuation of application No. 15/164,746, filed on May 25, 2016, now Pat. No. 9,457,023, which is a continuation-in-part of application No. 14/879,002, filed on Oct. 8, 2015, now Pat. No. 9,375,429, which is a continuation of application No. 14/554,988, filed on Nov. 26, 2014, now Pat. No. 9,205,083, which is a continuation of application No. 14/550,618, filed on Nov. 21, 2014, now Pat. No. 9,198,905, which is a continuation-in-part of application No. PCT/US2014/064184, filed on Nov. 5, 2014.

(60) Provisional application No. 62/645,751, filed on Mar. 20, 2018, provisional application No. 62/576,538, filed on Oct. 24, 2017, provisional application No. 61/900,354, filed on Nov. 5, 2013.

(51) Int. Cl.
| | |
|---|---|
| A61K 31/439 | (2006.01) |
| A61K 31/165 | (2006.01) |
| A61K 31/485 | (2006.01) |
| A61K 31/135 | (2006.01) |
| A61K 31/137 | (2006.01) |
| A61K 31/15 | (2006.01) |
| A61K 31/343 | (2006.01) |
| A61K 31/381 | (2006.01) |
| A61K 9/00 | (2006.01) |

(52) U.S. Cl.
CPC .......... *A61K 31/485* (2013.01); *A61K 9/0053* (2013.01); *A61K 31/135* (2013.01); *A61K 31/137* (2013.01); *A61K 31/15* (2013.01); *A61K 31/343* (2013.01); *A61K 31/381* (2013.01)

(58) Field of Classification Search
CPC .......................... A61K 31/439; A61K 31/165
USPC ................................. 514/281, 617
See application file for complete search history.

(56) References Cited

U.S. PATENT DOCUMENTS

| | | |
|---|---|---|
| 2,676,177 A | 4/1954 | Schnider et al. |
| 3,819,706 A | 6/1974 | Mehta |
| 4,687,660 A | 8/1987 | Baker et al. |
| 5,166,207 A | 11/1992 | Smith |
| 5,206,248 A | 4/1993 | Smith |
| 5,350,756 A | 9/1994 | Smith |
| 6,034,091 A | 3/2000 | Dante |
| 6,197,830 B1 | 3/2001 | Frome |
| 6,207,674 B1 | 3/2001 | Smith |
| 6,333,332 B1 | 12/2001 | Han et al. |
| 6,342,496 B1 | 1/2002 | Jerussi et al. |
| 6,436,938 B1 | 8/2002 | Howard |
| 6,458,374 B1 | 10/2002 | McCullough et al. |
| 6,562,835 B1 | 5/2003 | Caruso |
| 6,608,073 B1 | 8/2003 | Hussain et al. |
| 6,780,871 B2 | 8/2004 | Glick et al. |
| 6,897,241 B2 | 5/2005 | Frome |
| 7,569,610 B2 | 8/2009 | Oberegger et al. |
| 7,569,611 B2 | 8/2009 | Oberegger et al. |
| 7,579,380 B2 | 8/2009 | Oberegger et al. |
| 7,659,282 B2 | 2/2010 | Yakatan et al. |
| 7,674,479 B2 | 3/2010 | Zerbe et al. |
| 7,884,136 B2 | 2/2011 | Oberegger et al. |
| 7,973,043 B2 | 7/2011 | Migaly |

(Continued)

FOREIGN PATENT DOCUMENTS

| | | |
|---|---|---|
| AU | 2015350559 B2 | 12/2018 |
| EP | 1224930 | 7/2002 |

(Continued)

OTHER PUBLICATIONS

US 11,123,342 B2, 09/2021, Tabuteau (withdrawn)

(Continued)

*Primary Examiner* — Raymond J Henley, III
(74) *Attorney, Agent, or Firm* — MASCHOFF BRENNAN; Brent A. Johnson; Yuefen Zhou

(57) ABSTRACT

Dosage forms, drug delivery systems, and methods related to sustained release of dextromethorphan or improved therapeutic effects are disclosed. Typically, bupropion or a related compound is orally administered to a human being to be treated with, or being treated with, dextromethorphan.

22 Claims, 16 Drawing Sheets

(56) References Cited

U.S. PATENT DOCUMENTS

| | | |
|---|---|---|
| 7,973,049 B2 | 7/2011 | Tung |
| 8,017,623 B2 | 9/2011 | Singh |
| 8,188,110 B2 | 5/2012 | Tung |
| 8,227,484 B2 | 7/2012 | Yakatan et al. |
| 8,461,102 B2 | 6/2013 | Royster |
| 8,524,780 B2 | 9/2013 | Czarnik |
| 8,541,436 B2 | 9/2013 | Tung |
| 8,569,328 B1 | 10/2013 | Tabuteau |
| 8,728,528 B2 | 5/2014 | Biggs et al. |
| 8,796,302 B2 | 8/2014 | Hong et al. |
| 8,932,628 B2 | 1/2015 | Oberegger et al. |
| 9,168,234 B2 | 10/2015 | Tabuteau |
| 9,198,905 B2 | 12/2015 | Tabuteau |
| 9,205,083 B2 | 12/2015 | Tabuteau |
| 9,238,032 B2 | 1/2016 | Tabuteau |
| 9,278,095 B2 | 3/2016 | Tabuteau |
| 9,314,462 B2 | 4/2016 | Tabuteau |
| 9,370,513 B2 | 6/2016 | Tabuteau |
| 9,375,429 B2 | 6/2016 | Tabuteau |
| 9,402,843 B2 | 8/2016 | Tabuteau |
| 9,402,844 B2 | 8/2016 | Tabuteau |
| 9,408,815 B2 | 8/2016 | Tabuteau |
| 9,421,176 B1 | 8/2016 | Tabuteau |
| 9,457,023 B1 | 10/2016 | Tabuteau |
| 9,457,025 B2 | 10/2016 | Tabuteau |
| 9,474,731 B1 | 10/2016 | Tabuteau |
| 9,486,450 B2 | 11/2016 | Tabuteau |
| 9,700,528 B2 | 7/2017 | Tabuteau |
| 9,700,553 B2 | 7/2017 | Tabuteau |
| 9,707,191 B2 | 7/2017 | Tabuteau |
| 9,732,031 B2 | 8/2017 | DeWitt et al. |
| 9,763,932 B2 | 9/2017 | Tabuteau |
| 9,861,595 B2 | 1/2018 | Tabuteau |
| 9,867,819 B2 | 1/2018 | Tabuteau |
| 9,968,568 B2 | 5/2018 | Tabuteau |
| 10,058,518 B2 | 8/2018 | Tabuteau |
| 10,064,857 B2 | 9/2018 | Tabuteau |
| 10,080,727 B2 | 9/2018 | Tabuteau |
| 10,092,560 B2 | 10/2018 | Tabuteau |
| 10,092,561 B2 | 10/2018 | Tabuteau |
| 10,105,327 B2 | 10/2018 | Tabuteau |
| 10,105,361 B2 | 10/2018 | Tabuteau |
| 10,251,879 B2 | 4/2019 | Tabuteau |
| 10,463,634 B2 | 11/2019 | Tabuteau |
| 10,512,643 B2 | 12/2019 | Tabuteau |
| 10,548,857 B2 | 2/2020 | Tabuteau |
| 10,596,167 B2 | 3/2020 | Tabuteau |
| 10,688,066 B2 | 6/2020 | Tabuteau |
| 10,772,850 B2 | 9/2020 | Tabuteau |
| 10,780,064 B2 | 9/2020 | Tabuteau |
| 10,780,066 B2 | 9/2020 | Tabuteau |
| 10,786,469 B2 | 9/2020 | Tabuteau |
| 10,786,496 B2 | 9/2020 | Tabuteau |
| 10,799,497 B2 | 10/2020 | Tabuteau |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 | 1/2021 | Tabuteau |
| 10,894,047 B2 | 1/2021 | Tabuteau |
| 10,898,453 B2 | 1/2021 | Tabuteau |
| 10,925,842 B2 | 2/2021 | Tabuteau |
| 10,933,034 B2 | 3/2021 | Tabuteau |
| 10,940,124 B2 | 3/2021 | Tabuteau |
| 10,945,973 B2 | 3/2021 | Tabuteau |
| 10,966,941 B2 | 4/2021 | Tabuteau |
| 10,966,942 B2 | 4/2021 | Tabuteau |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 | 10/2021 | Tabuteau |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 | 12/2021 | Tabuteau |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 | 2/2022 | Tabuteau |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 | 2/2023 | Tabuteau |
| 11,576,909 B2 | 2/2023 | Tabuteau |
| 11,590,124 B2 | 2/2023 | Tabuteau |
| 11,596,627 B2 | 3/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 2002/0004078 A1 | 1/2002 | Gelber et al. |
| 2002/0035105 A1 | 3/2002 | Caruso |
| 2002/0103109 A1 | 8/2002 | Glick et al. |
| 2003/0144220 A1 | 7/2003 | Obach |
| 2004/0092511 A1 | 5/2004 | Billstein et al. |
| 2005/0085463 A1 | 4/2005 | Weiner et al. |
| 2005/0203125 A1 | 9/2005 | Yakatan et al. |
| 2005/0209218 A1 | 9/2005 | Meyerson et al. |
| 2005/0250767 A1 | 11/2005 | Weiner et al. |
| 2006/0167032 A1 | 7/2006 | Galer et al. |
| 2006/0258721 A1 | 11/2006 | Maddaford et al. |
| 2007/0027213 A1 | 2/2007 | Oberegger |
| 2007/0042969 A1 | 2/2007 | Rauschkolb-Loffler et al. |
| 2008/0008748 A1 | 1/2008 | Beyreuther et al. |
| 2008/0081072 A1 | 4/2008 | Cherukuri |
| 2008/0213217 A1 | 9/2008 | Storer et al. |
| 2008/0280936 A1 | 11/2008 | Tung |
| 2008/0286344 A1 | 11/2008 | Darmuzey et al. |
| 2009/0023744 A1 | 1/2009 | Fava |
| 2009/0111846 A1 | 4/2009 | Berg |
| 2009/0124583 A1 | 5/2009 | Nelson et al. |
| 2009/0162421 A1 | 6/2009 | Geisslinger et al. |

(56) References Cited

U.S. PATENT DOCUMENTS

| | | |
|---|---|---|
| 2009/0191257 A1 | 7/2009 | Smith |
| 2010/0029665 A1 | 2/2010 | Meyerson et al. |
| 2010/0040679 A1 | 2/2010 | Chang et al. |
| 2011/0039875 A1 | 2/2011 | Singh |
| 2011/0206780 A1 | 8/2011 | Gant et al. |
| 2011/0217371 A1 | 9/2011 | Shin et al. |
| 2011/0245208 A1 | 10/2011 | Diatchenko et al. |
| 2012/0053169 A1 | 3/2012 | Thomas |
| 2012/0083487 A1 | 4/2012 | Thomas |
| 2012/0252833 A1 | 10/2012 | Wertz et al. |
| 2013/0137714 A1 | 5/2013 | Berg |
| 2014/0018436 A1 | 1/2014 | Czarnik |
| 2014/0162965 A1 | 6/2014 | Maggio |
| 2015/0087669 A1 | 3/2015 | Lammert et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0128998 A1 | 5/2016 | Tabuteau |
| 2016/0136155 A1 | 5/2016 | Tabuteau |
| 2016/0143901 A1 | 5/2016 | Siffert et al. |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |
| 2017/0360774 A1 | 12/2017 | Tabuteau |
| 2017/0360776 A1 | 12/2017 | Tabuteau |
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1 | 1/2021 | Tabuteau |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |

(56) References Cited

U.S. PATENT DOCUMENTS

| | | |
|---|---|---|
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |
| 2023/0131854 A1 | 4/2023 | Tabuteau |
| 2023/0142244 A1 | 5/2023 | Tabuteau |

FOREIGN PATENT DOCUMENTS

| | | |
|---|---|---|
| EP | 2397158 | 12/2011 |
| EP | 2418211 | 2/2012 |
| WO | 1998050044 | 11/1998 |
| WO | 2000016762 | 3/2000 |
| WO | 2000041684 | 7/2000 |
| WO | 2000059486 | 10/2000 |
| WO | 2001045708 | 6/2001 |
| WO | 2002060425 | 8/2002 |
| WO | 2004075832 | 9/2004 |
| WO | 2006092691 | 9/2006 |
| WO | 2009006194 | 1/2009 |
| WO | 2009011412 | 1/2009 |
| WO | 2009062318 | 5/2009 |
| WO | 2009062319 | 5/2009 |
| WO | 2010000073 | 1/2010 |
| WO | 2010010343 | 1/2010 |
| WO | 2010062690 | 6/2010 |
| WO | 2010062692 | 6/2010 |
| WO | 2012118562 | 9/2012 |
| WO | 2012118563 | 9/2012 |
| WO | 2013136078 | 9/2013 |
| WO | 2013158680 | 10/2013 |
| WO | 2013190013 | 12/2013 |
| WO | 2014100501 | 6/2014 |
| WO | 2014138669 | 9/2014 |
| WO | 2015069809 A1 | 5/2015 |
| WO | 2015095713 | 6/2015 |
| WO | 2020146412 A1 | 7/2020 |
| WO | 2021202419 A1 | 10/2021 |

OTHER PUBLICATIONS

U.S. Appl. No. 14/628,062, filed Feb. 20, 2015 First Named Inventor: Herriot Tabuteau Assignee: Antecip Bioventures II LLC.
U.S. Appl. No. 14/863,284, filed Sep. 23, 2015 First Named Inventor: Herriot Tabuteau Assignee: Antecip Bioventures II LLC.
U.S. Appl. No. 14/878,998, filed Oct. 8, 2015 First Named Inventor: Herriot Tabuteau Assignee: Antecip Bioventures II LLC.
U.S. Appl. No. 14/879,002, filed Oct. 8, 2015 First Named Inventor: Herriot Tabuteau Assignee: Antecip Bioventures II LLC.
U.S. Appl. No. 14/978,976, filed Dec. 22, 2015 First Named Inventor: Herriot Tabuteau Assignee: Antecip Bioventures II LLC.
U.S. Appl. No. 14/997,316, filed Jan. 15, 2016 First Named Inventor: Herriot Tabuteau Assignee: Antecip Bioventures II LLC.
U.S. Appl. No. 15/057,983, filed Mar. 1, 2016 First Named Inventor: Herriot Tabuteau Assignee: Antecip Bioventures II LLC.
U.S. Appl. No. 15/130,807, filed Apr. 15, 2016 First Named Inventor: Herriot Tabuteau Assignee: Antecip Bioventures II LLC.
U.S. Appl. No. 15/164,746, filed May 25, 2016 First Named Inventor: Herriot Tabuteau Assignee: Antecip Bioventures II LLC.
U.S. Appl. No. 15/164,767, filed May 25, 2016 First Named Inventor: Herriot Tabuteau Assignee: Antecip Bioventures II LLC.
U.S. Appl. No. 15/206,057, filed Jul. 8, 2016 First Named Inventor: Herriot Tabuteau Assignee: Antecip Bioventures II LLC.
U.S. Appl. No. 15/182,253, filed Jun. 14, 2016 First Named Inventor: Herriot Tabuteau Assignee: Antecip Bioventures II LLC.
Wadhwa et al., Large-Dose Oral Dextromethorphan as an Adjunct to Patient-Controlled Analgesia with Morphine after Knee Surgery, Anesthesia & Analgesia, 92(2), 448-454, Feb. 2001.
Walker et al., An Open Label Trial of Dextromethorphan in Huntington's Disease, Clinical Neuropharmacology, 12(4), 322-330, Aug. 1989.
Weinbroum et al., The Role of Dextromethorphan in Pain Control, Canadian Journal of Anesthesia, 47(6), 585-596, Jun. 2000.
Zhu et al., CYP2B6 and Bupropion's Smoking—Cessation Pharmacology: The Role of Hydroxybupropion, Clinical Pharmacology & Therapeutics, 92(6), 771-777, Dec. 2012.
U.S. Appl. No. 15/213,283, filed Jul. 18, 2016 First Named Inventor: Herriot Tabuteau Assignee: Antecip Bioventures II LLC.
U.S. Appl. No. 15/216,545, filed Jul. 21, 2016 First Named Inventor: Herriot Tabuteau Assignee: Antecip Bioventures II LLC.
U.S. Appl. No. 15/224,233, filed Jul. 29, 2016 First Named Inventor: Herriot Tabuteau Assignee: Antecip Bioventures II LLC.
Jefferson, J. W., et al. (2005) "Bupropion for Major Depressive Disorder: Pharmacokinetic and Formulation Considerations," Clinical Therapeutics : vol. 27(11), pp. 1685-1695.
U.S. Appl. No. 15/236,290, filed Aug. 12, 2016 First Named Inventor: Herriot Tabuteau Assignee: Antecip Bioventures II LLC.
U.S. Appl. No. 15/238,182, filed Aug. 16, 2016 First Named Inventor: Herriot Tabuteau Assignee: Antecip Bioventures II LLC.
U.S. Appl. No. 15/263,138, filed Sep. 12, 2016 First Named Inventor: Herriot Tabuteau Assignee: Antecip Bioventures II LLC.
U.S. Appl. No. 15/275,177, filed Sep. 23, 2016 First named Inventor: Herriot Tabuteau Assignee: Antecip Bioventures II LLC.
U.S. Appl. No. 15/280,938, filed Sep. 29, 2016 First named Inventor: Herriot Tabuteau Assignee: Antecip Bioventures II LLC.
"Avanir & Concert Announce Exclusive License Agreement," http://drug-dev.com/Main/Current-News/362012-573, aspx, Mar. 6, 2012, publication.
Wellbutrin XL (bupropion hydrochloride extended-release) tablets for oral use, Dec. 2014.
Devane, Hum. Psychopharmacol. Clin. Exp. 13:5, 329-336, 1998.
Dwoskin et al., "Review of the Pharmacology and Clinical Profile of Bupropion, an Antidepressant and Tobacco Use Cessation Agent," CNS Drug Reviews, v12, No. 3-4, pp. 178-207, 2006.
Extended European Search Report for EP14859589 (corresponding to PCT/US2014064184), Mar. 8, 2017.
Patent Application No. PCT/US2017/024140 Filed: Mar. 24, 2017 First named Inventor: Herriot Tabuteau Assignee: Antecip Bioventures II LLC.
U.S. Appl. No. 15/599,163, filed May 18, 2017 First named Inventor: Herriot Tabuteau Assignee: Antecip Bioventures II LLC.
U.S. Appl. No. 15/621,882, filed Jun. 13, 2017 First named Inventor: Herriot Tabuteau Assignee: Antecip Bioventures II LLC.
U.S. Appl. No. 15/645,939, filed Jul. 10, 2017 First named Inventor: Herriot Tabuteau Assignee: Antecip Bioventures II LLC.
U.S. Appl. No. 15/647,069, filed Jul. 11, 2017 First named Inventor: Herriot Tabuteau Assignee: Antecip Bioventures II LLC.
U.S. Appl. No. 15/647,852, filed Jul. 12, 2017 First named Inventor: Herriot Tabuteau Assignee: Antecip Bioventures II LLC.
U.S. Appl. No. 15/688,660. filed Aug. 28, 2017 First named Inventor: Herriot Tabuteau Assignee: Antecip Bioventures II LLC.
U.S. Appl. No. 15/691,532, filed Aug. 30, 2017 First named Inventor: Herriot Tabuteau Assignee: Antecip Bioventures II LLC.
U.S. Appl. No. 15/691,549. filed Aug. 30, 2017 First named Inventor: Herriot Tabuteau Assignee: Antecip Bioventures II LLC.
U.S. Appl. No. 15/695,995, filed Sep. 5, 2017 First named Inventor: Herriot Tabuteau Assignee: Antecip Bioventures II LLC.
U.S. Appl. No. 15/821,563, filed Nov. 22, 2017 First named Inventor: Herriot Tabuteau Assignee: Antecip Bioventures II LLC.
U.S. Appl. No. 15/842,599, filed Dec. 14, 2017 First named Inventor: Herriot Tabuteau Assignee: Antecip Bioventures II LLC.
U.S. Appl. No. 15/856,853, filed Dec. 28, 2017 First named Inventor: Herriot Tabuteau Assignee: Antecip Bioventures II LLC.

(56) References Cited

OTHER PUBLICATIONS

U.S. Appl. No. 15/933,075, filed Mar. 22, 2018 First named Inventor: Herriot Tabuteau Assignee: Antecip Bioventures II LLC.
U.S. Appl. No. 15/977,276, filed May 11, 2018 First named Inventor: Herriot Tabuteau Assignee: Antecip Bioventures II LLC.
Coles et al., "Stereoselective Metabolism of Bupropion by Cytochrome P4502B6 (CYP2B6) and Human Liver Microsomes", Pharmaceutical Research, vol. 25, No. 6, 1405-1411, Jun. 2008.
Coles et al., "Stereoselective Analysis of Bupropion and Hydroxybupropion in Human Plasma and Urine by LC/MS/MS", Journal of Chromatography B, vol. 857, No. 1, 67-75, Sep. 2007.
Joy et al., "Use of Enantiomeric Bupropion and Hydroxybupropion to Assess CYP2B6 Activity in Glomerular Kidney Diseases", Journal of Clinical Pharmacology, 50, 714-720, 2010.
Sager et al., "In Vitro to In Vivo Extrapolation of the Complex Drug-Drug Interaction of Bupropion and Its Metabolites with CYP2D6; Simultaneous Reversible Inhibition and CYP2D6 Downregulation", Biochem. Pharmacol., 123, 85-96, Jan. 2017.
Abdel-Rahman et al., Potent Inhibition of Cytochrome P-450 2D6-mediated Dextromethorphan O-Demethylation by Terbinafine, Drug Metabolism and Disposition, 27(7), 770-775, Jul. 1999.
Bachmann, K., Chapter 12—Drug-drug interactions with an emphasis on drug metabolism and transport, Pharmacology Principles and Practice, Academic Press, 303-325, 2009.
Chyka et al., Dextromethorphan Poisoning: An Evidence-Based Consensus Guideline for Out-of-Hospital Management, Clinical Toxicology, 45(6): 662-677, Sep. 2007.
Desmeules et al., Contribution of Cytochrome P-4502D6 Phenotype to the Neuromodulatory Effects of Dextromethorphan, Journal of Pharmacology and Experimental Therapeutics, 288(2), 607-612, Feb. 1999.
Dextromethorphan Product Labeling Under the OTC Monograph 21 CFR 341.74, 1 pg., last accessed Nov. 2013.
Droll et al., Comparison of Three CYP2D6 Probe Substrates and Genotype in Ghanaians, Chinese and Caucasians Pharmacogenetics and Genomics, 8(4), 325-333, Aug. 1998.
Drug Interactions between Dextromethorphan/Guaifenesin and Wellbutrin XL®, Drugs.com, last accessed Apr. 11, 2016, 1 pg., available at: http://www.drugs.com/drug-interactions/dextromethorphan-guaifenesin-with-wellbutrin-xl-846-0-440-2469.html.
Fairstein et al., Regional-Dependent Intestinal Permeability and BCS Classification: Elucidation of pH-Related Complexity in Rats Using Pseudoephedrine, The AAPS Journal, 15(2), 589-597, Apr. 2013.
Garnock-Jones, Dextromethorphan/Quinidine: In Pseudobulbar Affect, CNS Drugs, 25(5), 435-45, May 2011.
Gilron et al., A Randomized, Controlled Trial of High-Dose Dextromethorphan in Facial Neuralgias, Neurology, 55(7), 964-971, Oct. 2000.
Glaxosmithkline, Wellbutrin XL® Prescribing Information, 2009, 33 pgs., available at: http://www.accessdata.fda.gov/drugsatfda_docs/label/2009/021515s023s024lbl.pdf.
Glaxosmithkline, Zyban® Prescribing Information, Aug. 2011, 28 pgs, available at: http://www.accessdata.fda.gov/drugsatfda_docs/label/2011/020711s026lbl.pdf.
Güzey et al., Change from the CYP2D6 Extensive Metabolizer to the Poor Metabolizer Phenotype During Treatment with Bupropion, Therapeutic Drug Monitoring, 24(3), 436-437, Jun. 2002.
Howard et al., The Efficacy and Toxicity of Bupropion in the Elderly, Jefferson Journal of Psychiatry, 15(1), 34-38, Jan. 2000.
Humanwell Puracap Pharmaceutical (Wuhan), Ltd., Dextromethorphan HBR, Prescribing information, 4 pgs., revised Jan. 2014.
Kelly et al., The Utility of the Combination of Dextromethorphan and Quinidine in the Treatment of Bipolar II and Bipolar NOS Journal of Affective Disorders, 167, 333-335, Oct. 2014.
Kiptoo et al., Transdermal Delivery of Bupropion and its Active Metabolite, Hydroxybupropion: A Prodrug Strategy as an Alternative Approach, Journal of Pharmaceutical Sciences, 98(2), 583-594, Feb. 2009.

Kotlyar et al., Inhibition of CYP2D6 Activity by Bupropion, Journal of Clinical Psychopharmacology, 25(2), 226-229, Jun. 2005.
Lauterbach, Dextromethorphan as a Potential Rapid-Acting Antidepressant, Medical Hypotheses, 76(5), 717-719, May 2011.
Lauterbach, An Extension of Hypotheses Regarding Rapid-Acting, Treatment-Refractory, and Conventional Antidepressant Activity of Dextromethorphan and Dextrorphan, Medical Hypotheses, 78(6), 693-702, Jun. 2012.
Lee et al., The DRD2/ANKK1 Gene is Associated with Response to Add-on Dextromethorphan Treatment in Bipolar Disorder, Journal of Affective Disorders, 138(3), 295-300, May 2012.
Mizoguchi et al., Efficacy of a Single Evening Dose of Syrup containing Paracetamol, Dextromethorophan Hydrobromide, Doxylamine Succinate and Ephedrine Sulfate in Subjects with Multiple Common Cold Symptoms, International Journal of Clinical Pharmacology and Therapeutics, 45(4), 230-236, Apr. 2007.
Nakashima et al., Effect of Cinacalcet Hydrochloride, a New Calcimimetic Agent, on the Pharmacokinetics of Dextromethorphan: In Vitro and Clinical Studies, The Journal of Clinical Pharmacology, 47(10), 1311-1319, Oct. 2007.
Nelson et al., High-Dose Oral Dextromethorphan Versus Placebo in Painful Diabetic Neuropathy and Postherpetic Neuralgia, Neurology, 48(5), 1212-1218, May 1997.
Nguyen et al., Involvement of Sigma-1 Receptors in the Antidepressant-like Effects of Dextromethorphan, PLOS One, 9(2), 9 pgs., Feb. 2014.
Olney et al., AVP-923, A Combination of Dextromethorphan Hydrobromide and Quinidine Sulfate for the Treatment of Pseudobulbar Affect and Neuropathic Pain, IDrugs: The Investigational Drugs Journal, 13(4), 254-265, Apr. 2010.
Pioro et al., Dextromethorphan Plus Ultra Low-Dose Quinidine Reduces Pseudobulbar Affect, Annals of Neurology, 68(5), 693-702, Nov. 2010.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Reese et al., An in Vitro Mechanistic Study to Elucidate the Desipramine/Bupropion Clinical Drug-Drug Interaction, Drug Metabolism and Disposition, 36(7), 1198-1201, Jul. 2008.
Rosen, Dextromethorphan/Quinidine Sulfate (ZENVIA™) for Pseudobulbar Affect, Drugs of Today, 44(9), 661-668, Sep. 2008.
Rowley, Regulatory History and Background on Over-the-Counter Dextromethorphan, FDA Drug Safety and Risk Management Advisory Committee Meeting, Presentation, 21 pgs., Sep. 14, 2010.
Sang et al., Dextromethorphan and Memantine in Painful Diabetic Neuropathy and Postherpetic Neuralgia, Anesthesiology, 96(5), 1053-1061, May 2002.
Semenchuk et al., Efficacy of Sustained-Release Bupropion in Neuropathic Pain: An Open-Label Study, The Clinical Journal of Pain, 16(1), 6-11, Mar. 2000.
Semenchuk et al., Double-Blind, Randomized Trial of Bupropion SR for the Treatment of Neuropathic Pain, Neurology, 57(9), 1583-1588, Nov. 2001.
Shah et al., Bupropion for the Treatment of Neuropathic Pain, American Journal of Hospice & Palliative Medicine, 27(5), 333-336, Aug. 2010.
Shaibani et al., Efficacy and Safety of Dextromethorphan/Quinidine at Two Dosage Levels for Diabetic Neuropathic Pain: A Double-Blind, Placebo-Controlled, Multicenter Study, Pain Medicine, 13(2), 243-254, Feb. 2012.
Silverstone et al., Convulsive Liability of Bupropion Hydrochloride Metabolites in Swiss Albino Mice, Annals of General Psychiatry, 7(1), Article 19, 8 pgs., Oct. 2008.
Smith, Dextromethorphan/Quinidine: A Novel Dextromethorphan Product for the Treatment of Emotional Lability, Expert Opinion on Pharmacotherapy, 7(18), 2581-2598, Dec. 2006.
Spina et al., Clinically Relevant Pharmacokinetic Drug Interactions with Second-Generation Antidepressants: An Update, Clinical Therapeutics, 30(7), 1206-1227, Jul. 2008.

(56) References Cited

OTHER PUBLICATIONS

Struthers et al., Mecamylamine, Dihydro-β-Erythroidine, and Dextromethorphan Block Conditioned Responding Evoked by the Conditional Stimulus Effects of Nicotine, Pharmacology, Biochemistry and Behavior, 94(2), 319-328, Dec. 2009.
Thisted et al., Dextromethorphan and Quinidine in Adult Patients with Uncontrolled Painful Diabetic Peripheral Neuropathy: A 29-Day, Multicenter, Open-Label, Dose-Escalation Study, Clinical Therapeutics, 28(10), 1607-1618, Oct. 2006.
Tod et al., Quantitative Prediction of Cytochrome P450 (CYP) 2D6-Mediated Drug Interactions, Clinical Pharmacokinetics, 50(8), 519-530, Aug. 2011.
U.S. Appl. No. 13/478,023, filed May 22, 2012 First Named Inventor: Herriot Tabuteau Assignee: Antecip Bioventures II LLC.
U.S. Appl. No. 14/550,618, filed Nov. 21, 2014 First Named Inventor: Herriot Tabuteau Assignee: Antecip Bioventures II LLC.
U.S. Appl. No. 14/554,947, filed Nov. 26, 2014 First Named Inventor: Herriot Tabuteau Assignee: Antecip Bioventures II LLC.
U.S. Appl. No. 14/554,988, filed Nov. 26, 2014 First Named Inventor: Herriot Tabuteau Assignee: Antecip Bioventures II LLC.
U.S. Appl. No. 14/555,085, filed Nov. 26, 2014 First Named Inventor: Herriot Tabuteau Assignee: Antecip Bioventures II LLC.
U.S. Appl. No. 14/602,177, filed Jan. 21, 2015 First Named Inventor: Herriot Tabuteau Assignee: Antecip Bioventures II LLC.
U.S. Appl. No. 14/604,397, filed Jan. 23, 2015 First Named Inventor: Herriot Tabuteau Assignee: Antecip Bioventures II LLC.
U.S. Appl. No. 14/617,624, filed Feb. 9, 2015 First Named Inventor: Herriot Tabuteau Assignee: Antecip Bioventures II LLC.
Wellbutrin SR® "Information for the Patient", Glaxo Wellcome Inc. North Carolina USA, Mar. 2001.
Siu et al., "Dextromethorphan: A Review of N-methyl-D-aspartate Receptor Antagonist in the Management of Pain", DNS Drug Reviews, 13(1), 96-106, 2007.
Shah et al., "Bupropion for the Treatment of Neuropathic Pain", American Journal of Hospice & Palliative Medicine, 27(5), 333-336, 2010.
U.S. Appl. No. 17/373,299, filed Jul. 12, 2021 First Named Inventor: Herriot Tabuteau Assignee: Antecip Bioventures II LLC.
U.S. Appl. No. 17/380,751, filed Jul. 20, 2021 First Named Inventor: Herriot Tabuteau Assignee: Antecip Bioventures II LLC.
U.S. Appl. No. 17/395,222, filed Aug. 5, 2021 First Named Inventor: Herriot Tabuteau Assignee: Antecip Bioventures II LLC.
U.S. Appl. No. 17/405,429, filed Aug. 18, 2021 First Named Inventor: Herriot Tabuteau Assignee: Antecip Bioventures II LLC.
International Preliminary Report on Patentability, PCT/US2020/012612, dated Jul. 22, 2021.
U.S. Appl. No. 17/468,149, filed Sep. 7, 2021 First Named Inventor: Herriot Tabuteau Assignee: Antecip Bioventures II LLC.
U.S. Appl. No. 17/470,831, filed Sep. 9, 2021 First Named Inventor: Herriot Tabuteau Assignee: Antecip Bioventures II LLC.
U.S. Appl. No. 17/471,895, filed Sep. 10, 2021 First Named Inventor: Herriot Tabuteau Assignee: Antecip Bioventures II LLC.
U.S. Appl. No. 17/471,983, filed Sep. 10, 2021 First Named Inventor: Herriot Tabuteau Assignee: Antecip Bioventures II LLC.
U.S. Appl. No. 17/473,860, filed Sep. 13, 2021 First Named Inventor: Herriot Tabuteau Assignee: Antecip Bioventures II LLC.
U.S. Appl. No. 17/482,241, filed Sep. 22, 2021 First Named Inventor: Herriot Tabuteau Assignee: Antecip Bioventures II LLC.
U.S. Appl. No. 17/498,507, filed Oct. 11, 2021 First Named Inventor: Herriot Tabuteau Assignee: Antecip Bioventures II LLC.
U.S. Appl. No. 17/525,339, filed Nov. 12, 2021 First Named Inventor: Herriot Tabuteau Assignee: Antecip Bioventures II LLC.
U.S. Appl. No. 17/526,676, filed Nov. 15, 2021 First Named Inventor: Herriot Tabuteau Assignee: Antecip Bioventures II LLC.
U.S. Appl. No. 17/541,461, filed Dec. 3, 2021 First Named Inventor: Herriot Tabuteau Assignee: Antecip Bioventures II LLC.
U.S. Appl. No. 17/547,050, filed Dec. 9, 2021 First Named Inventor: Herriot Tabuteau Assignee: Antecip Bioventures II LLC.
U.S. Appl. No. 17/571,110, filed Jan. 7, 2022 First Named Inventor: Herriot Tabuteau Assignee: Antecip Bioventures II LLC.
U.S. Appl. No. 17/574,378, filed Jan. 12, 2022 First Named Inventor: Herriot Tabuteau Assignee: Antecip Bioventures II LLC.
U.S. Appl. No. 17/581,292, filed Jan. 21, 2022 First Named Inventor: Herriot Tabuteau Assignee: Antecip Bioventures II LLC.
U.S. Appl. No. 17/693,711, filed Mar. 14, 2022 First Named Inventor: Herriot Tabuteau Assignee: Antecip Bioventures II LLC.
U.S. Appl. No. 17/705,930, filed Mar. 28, 2022 First Named Inventor: Herriot Tabuteau Assignee: Antecip Bioventures II LLC.
U.S. Appl. No. 17/707,221, filed Mar. 29, 2022 First Named Inventor: Herriot Tabuteau Assignee: Antecip Bioventures II LLC.
U.S. Appl. No. 17/657,832, filed Apr. 4, 2022 First Named Inventor: Herriot Tabuteau Assignee: Antecip Bioventures II LLC.
U.S. Appl. No. 17/712,970, filed Apr. 4, 2022 First Named Inventor: Herriot Tabuteau Assignee: Antecip Bioventures II LLC.
U.S. Appl. No. 17/716,796, filed Apr. 8, 2022 First Named Inventor: Herriot Tabuteau Assignee: Antecip Bioventures II LLC.
U.S. Appl. No. 17/717,516, filed Apr. 11, 2022 First Named Inventor: Herriot Tabuteau Assignee: Antecip Bioventures II LLC.
U.S. Appl. No. 17/721,827, filed Apr. 15, 2022 First Named Inventor: Herriot Tabuteau Assignee: Antecip Bioventures II LLC.
Siffert, Letters to the Editor, Dextromethorphan/Quinidine for Agitation in Alzheimer's Disease, Neurology Today, Nov. 5, 2015. (/neurotodayonline/pages/default.aspx).
U.S. Appl. No. 17/730,814. filed Apr. 27, 2022 First Named Inventor: Herriot Tabuteau Assignee: Antecip Bioventures II LLC.
U.S. Appl. No. 17/735,470, filed May 3, 2022 First Named Inventor: Herriot Tabuteau Assignee: Antecip Bioventures II LLC.
U.S. Appl. No. 17/748,475, filed May 19, 2022 First Named Inventor: Herriot Tabuteau Assignee: Antecip Bioventures II LLC.
U.S. Appl. No. 17/836,560, filed Jun. 9, 2022 First Named Inventor: Herriot Tabuteau Assignee: Antecip Bioventures II LLC.
U.S. Appl. No. 17/841,274, filed Jun. 15, 2022 First Named Inventor: Herriot Tabuteau Assignee: Antecip Bioventures II LLC.
Wood et al., OTC Dextromethorphan-Induced Serotonin Syndrome, U.S. Pharmacist, Apr. 2010. (https://www.uspharmacist.com/article/otc-dextromethorphan-induced-serotonin-syndrome).
Written Opinion of the International Searching Authority for PCT/US2014/071519 (corresponding to WO2015095713) dated Feb. 10, 2015.
U.S. Appl. No. 16/107,472, filed Aug. 21, 2018 First Named Inventor: Herriot Tabuteau Assignee: Antecip Bioventures II LLC.
U.S. Appl. No. 16/116,393, filed Aug. 29, 2018 First Named Inventor: Herriot Tabuteau Assignee: Antecip Bioventures II LLC.
U.S. Appl. No. 16/119,852, filed Aug. 31, 2018 First Named Inventor: Herriot Tabuteau Assignee: Antecip Bioventures II LLC.
U.S. Appl. No. 16/127,832, filed Sep. 11, 2018 First Named Inventor: Herriot Tabuteau Assignee: Antecip Bioventures II LLC.
U.S. Appl. No. 16/129,531, filed Sep. 12, 2018 First Named Inventor: Herriot Tabuteau Assignee: Antecip Bioventures II LLC.
U.S. Appl. No. 16/130,898, filed Sep. 13, 2018 First Named Inventor: Herriot Tabuteau Assignee: Antecip Bioventures II LLC.
U.S. Appl. No. 16/133,553, filed Sep. 17, 2018 First Named Inventor: Herriot Tabuteau Assignee: Antecip Bioventures II LLC.
U.S. Appl. No. 16/246,347, filed Jan. 11, 2019 First Named Inventor: Herriot Tabuteau Assignee: Antecip Bioventures II LLC.
U.S. Appl. No. 16/290,653, filed Mar. 1, 2019 First Named Inventor: Herriot Tabuteau Assignee: Antecip Bioventures II LLC.
U.S. Appl. No. 16/359,958, filed Mar. 20, 2019 First Named Inventor: Herriot Tabuteau Assignee: Antecip Bioventures II LLC.
U.S. Appl. No. 16/359,996, filed Mar. 20, 2019 First Named Inventor: Herriot Tabuteau Assignee: Antecip Bioventures II LLC.
U.S. Appl. No. 16/364,005, filed Mar. 25, 2019 First Named Inventor: Herriot Tabuteau Assignee: Antecip Bioventures II LLC.
U.S. Appl. No. 16/364,463, filed Mar. 26, 2019 First Named Inventor: Herriot Tabuteau Assignee: Axsome Therapeutics, Inc.
U.S. Appl. No. 16/579,305, filed Sep. 23, 2019 First Named Inventor: Herriot Tabuteau Assignee: Axsome Therapeutics, Inc.
U.S. Appl. No. 16/588,399, filed Sep. 30, 2019 First Named Inventor: Herriot Tabuteau Assignee: Antecip Bioventures II LLC.
U.S. Appl. No. 16/681,317, filed Nov. 12, 2019 First Named Inventor: Herriot Tabuteau Assignee: Antecip Bioventures II LLC.

(56) References Cited

OTHER PUBLICATIONS

Murrough et al., Dextromethorphan/quinidine pharmacotherapy in patients with treatment resistant depression: a proof of concept clinical trial, Journal of affective disorders, 218, 277-283, Aug. 2017.
U.S. Appl. No. 16/736,752, filed Jan. 7, 2020 First Named Inventor: Herriot Tabuteau Assignee: Antecip Bioventures II LLC.
U.S. Appl. No. 16/745,105, filed Jan. 16, 2020 First Named Inventor: Herriot Tabuteau Assignee: Antecip Bioventures II LLC.
Drugs.com, Bupropion Hydrochloride, Feb. 5, 2018.
U.S. Appl. No. 16/817,119, filed Mar. 12, 2020 First Named Inventor: Herriot Tabuteau Assignee: Antecip Bioventures II LLC.
U.S. Appl. No. 16/821,330, filed Mar. 17, 2020 First Named Inventor: Herriot Tabuteau Assignee: Antecip Bioventures II LLC.
U.S. Appl. No. 16/821,462, filed Mar. 17, 2020 First Named Inventor: Herriot Tabuteau Assignee: Antecip Bioventures II LLC.
U.S. Appl. No. 16/822,564, filed Mar. 18, 2020 First Named Inventor: Herriot Tabuteau Assignee: Antecip Bioventures II LLC.
U.S. Appl. No. 16/822,697, filed Mar. 18, 2020 First Named Inventor: Herriot Tabuteau Assignee: Antecip Bioventures II LLC.
U.S. Appl. No. 16/823,724, filed Mar. 19, 2020 First Named Inventor: Herriot Tabuteau Assignee: Antecip Bioventures II LLC.
U.S. Appl. No. 16/823,807, filed Mar. 19, 2020 First Named Inventor: Herriot Tabuteau Assignee: Antecip Bioventures II LLC.
U.S. Appl. No. 16/825,195, filed Mar. 20, 2020 First Named Inventor: Herriot Tabuteau Assignee: Antecip Bioventures II LLC.
U.S. Appl. No. 16/825,228, filed Mar. 20, 2020 First Named Inventor: Herriot Tabuteau Assignee: Antecip Bioventures II LLC.
U.S. Appl. No. 16/826,580, filed Mar. 23, 2020 First Named Inventor: Herriot Tabuteau Assignee: Antecip Bioventures II LLC.
U.S. Appl. No. 16/826,598, filed Mar. 23, 2020 First Named Inventor: Herriot Tabuteau Assignee: Antecip Bioventures II LLC.
U.S. Appl. No. 16/828,237, filed Mar. 24, 2020 First Named Inventor: Herriot Tabuteau Assignee: Antecip Bioventures II LLC.
U.S. Appl. No. 16/838,829, filed Apr. 2, 2020 First Named Inventor: Herriot Tabuteau Assignee: Antecip Bioventures II LLC.
Avanir Pharmaceuticals v. Actavis South Atlantic, Cite as 36 F.Supp. 3d 475 (D.Del. 2014), accessed an Apr. 16, 2020.
U.S. Appl. No. 16/852,939, filed Apr. 20, 2020 First Named Inventor: Herriot Tabuteau Assignee: Antecip Bioventures II LLC.
U.S. Appl. No. 16/853,062, filed Apr. 20, 2020 First Named Inventor: Herriot Tabuteau Assignee: Antecip Bioventures II LLC.
International Search Report and Written Opinion of the International Searching Authority for PCT/US2020/012612, dated Apr. 30, 2020.
Lauterbach, Treatment Resistant Depression with Loss of Antidepressant Response: Rapid-Acting Antidepressant Action of Dextromethorphan, a Possible Treatment Bridging Molecule, Psychopharmacology Bulletin, 46(2), 53-57, Aug. 2016.
Koshino et al., The efficacy and safety of bupropion sustained-release formulation for the treatment of major depressive disorder: a multi-center, randomized, double-blind, placebo-controlled study in Asian patients, Neuropsychiatric Disease and Treatment, 9, 1273-1280, Aug. 2013.
Sheng et al., Sustained-Release Bupropion for Smoking Cessation in a Chinese Sample: A Double-Blind,Placebo-Controlled, Randomized Trial, Nicotine &Tobacco Research, 15(2), 320-325, Feb. 2013.
Leelahanaj, Developing Thai Economic Model to Study Cost-Effectiveness of Switching to Bupropion Compared to Combination with Bupropion after the Failure of an SSRI for Major Depressive Disorder, J Med Assoc Thai, 93 (Suppl 6), S35-S42, 2010.
Nofziger et al., Evaluation of dextromethorphan with select antidepressant therapy for the treatment of depression in the acute care psychiatric setting, Mental Health Clinician, 9(2), 76-81, Mar. 2019.
SPRAVATO™ (esketamine) Highlights of Prescribing Information, Mar. 2019.
Gideons et al., Mechanisms underlying differential effectiveness of memantine and ketamine in rapid antidepressant responses, Proceedings of the National Academy of Sciences, 111(23), 8649-8654, Jun. 2014.

Muhonen et al., Double-Blind, Randomized Comparison of Memantine and Escitalopram for the Treatment of Major Depressive Disorder Comorbid with Alcohol Dependence, The Journal of Clinical Psychiatry, 69(3), 392-399, Mar. 2008.
"Rapastinel Fails to Outperform Placebo in Phase 3 Studies", Mar. 2019, downloaded from https://www.psychcongress.com/article/rapastinel-fails-outperform-placebo-phase-3-studies, on May 28, 2020.
Rogoz et al., Amantadine as an additive treatment in patients suffering from drug-resistant unipolar depression, Pharmacological Reports, 59(6), 778-784, Nov. 2007.
Smith et al., Antidepressant Augmentation Using the NMDA-Antagonist Memantine: a Randomized, Double-Blind, Placebo-Controlled Trial, The Journal of Clinical Psychiatry, 74(10), 966-973, Oct. 2013.
Wright Jr. et al., Comparative Effects of Dextromethorphan and Dextrorphan on Nicotine Discrimination in Rats, Pharmacology Biochemistry and Behavior, 85(3), 507-513, Nov. 2006.
Zarate Jr. et al., A Double-Blind, Placebo-Controlled Study of Memantine in the Treatment of Major Depression, American Journal of Psychiatry, 163(1), 153-155, Jan. 2006.
Ferguson et al., An open-label, flexible-dose study of memantine in major depressive disorder, Clinical Neuropharmacology, 30(3), 136-144, May 2007.
Chou et al., Binding of dimemorfan to sigma-1 receptor and its anticonvulsant and locomotor effects in mice, compared with dextromethorphan and dextrorphan, Brain research, 821(2), 516-519, Mar. 1999.
Foley et al., Bupropion: pharmacology and therapeutic applications, Expert review of neurotherapeutics, 6(9), 1249-1265, Sep. 2006.
U.S. Appl. No. 16/894,713, filed Jun. 5, 2020 First Named Inventor: Herriot Tabuteau Assignee: Antecip Bioventures II LLC.
U.S. Appl. No. 16/926,458, filed Jul. 10, 2020 First Named Inventor: Herriot Tabuteau Assignee: Antecip Bioventures II LLC.
U.S. Appl. No. 16/983,873, filed Aug. 3, 2020 First Named Inventor: Herriot Tabuteau Assignee: Antecip Bioventures II LLC.
U.S. Appl. No. 17/002,017, filed Aug. 25, 2020 First Named Inventor: Herriot Tabuteau Assignee: Antecip Bioventures II LLC.
U.S. Appl. No. 17/003,777, filed Aug. 26, 2020 First Named Inventor: Herriot Tabuteau Assignee: Antecip Bioventures II LLC.
U.S. Appl. No. 17/020,393, filed Sep. 14, 2020 First Named Inventor: Herriot Tabuteau Assignee: Antecip Bioventures II LLC.
U.S. Appl. No. 17/022,629, filed Sep. 16, 2020 First Named Inventor: Herriot Tabuteau Assignee: Antecip Bioventures II LLC.
U.S. Appl. No. 17/022,781, filed Sep. 16, 2020 First Named Inventor: Herriot Tabuteau Assignee: Antecip Bioventures II LLC.
U.S. Appl. No. 17/024,145, filed Sep. 17, 2020 First Named Inventor: Herriot Tabuteau Assignee: Antecip Bioventures II LLC.
U.S. Appl. No. 17/025,849, filed Sep. 18, 2020 First Named Inventor: Herriot Tabuteau Assignee: Antecip Bioventures II LLC.
U.S. Appl. No. 17/027,608, filed Sep. 21, 2020 First Named Inventor: Herriot Tabuteau Assignee: Antecip Bioventures II LLC.
U.S. Appl. No. 17/030,129, filed Sep. 23, 2020 First Named Inventor: Herriot Tabuteau Assignee: Antecip Bioventures II LLC.
U.S. Appl. No. 17/039,551, filed Sep. 30, 2020 First Named Inventor: Herriot Tabuteau Assignee: Antecip Bioventures II LLC.
U.S. Appl. No. 17/061,047, filed Oct. 1, 2020 First Named Inventor: Herriot Tabuteau Assignee: Antecip Bioventures II LLC.
U.S. Appl. No. 17/063,364, filed Oct. 5, 2020 First Named Inventor: Herriot Tabuteau Assignee: Antecip Bioventures II LLC.
U.S. Appl. No. 17/066,310, filed Oct. 8, 2020 First Named Inventor: Herriot Tabuteau Assignee: Antecip Bioventures II LLC.
U.S. Appl. No. 17/068,309, filed Oct. 12, 2020 First Named Inventor: Herriot Tabuteau Assignee: Antecip Bioventures II LLC.
U.S. Appl. No. 17/070,706, filed Oct. 14, 2020 First Named Inventor: Herriot Tabuteau Assignee: Antecip Bioventures II LLC.
U.S. Appl. No. 17/071,925, filed Oct. 15, 2020 First Named Inventor: Herriot Tabuteau Assignee: Antecip Bioventures II LLC.
U.S. Appl. No. 17/075,189, filed Oct. 20, 2020 First Named Inventor: Herriot Tabuteau Assignee: Antecip Bioventures II LLC.
U.S. Appl. No. 17/087,890, filed Nov. 3, 2020 First Named Inventor: Herriot Tabuteau Assignee: Antecip Bioventures II LLC.
U.S. Appl. No. 17/092,968, filed Nov. 9, 2020 First Named Inventor: Herriot Tabuteau Assignee: Antecip Bioventures II LLC.

(56) References Cited

OTHER PUBLICATIONS

U.S. Appl. No. 17/095,256, filed Nov. 11, 2020 First Named Inventor: Herriot Tabuteau Assignee: Antecip Bioventures II LLC.
U.S. Appl. No. 17/097,486, filed Nov. 13, 2020 First Named Inventor: Herriot Tabuteau Assignee: Antecip Bioventures II LLC.
U.S. Appl. No. 17/099,226, filed Nov. 16, 2020 First Named Inventor: Herriot Tabuteau Assignee: Antecip Bioventures II LLC.
U.S. Appl. No. 16/950,838, filed Nov. 17, 2020 First Named Inventor: Herriot Tabuteau Assignee: Antecip Bioventures II LLC.
U.S. Appl. No. 17/100,456, filed Nov. 20, 2020 First Named Inventor: Herriot Tabuteau Assignee: Antecip Bioventures II LLC.
U.S. Appl. No. 17/103,819, filed Nov. 24, 2020 First Named Inventor: Herriot Tabuteau Assignee: Antecip Bioventures II LLC.
U.S. Appl. No. 17/115,073, filed Dec. 8, 2020 First Named Inventor: Herriot Tabuteau Assignee: Antecip Bioventures II LLC.
U.S. Appl. No. 17/191,014, filed Mar. 3, 2021 First Named Inventor: Herriot Tabuteau Assignee: Antecip Bioventures II LLC.
U.S. Appl. No. 17/192,192, filed Mar. 4, 2021 First Named Inventor: Herriot Tabuteau Assignee: Antecip Bioventures II LLC.
U.S. Appl. No. 17/192,563, filed Mar. 4, 2021 First Named Inventor: Herriot Tabuteau Assignee: Antecip Bioventures II LLC.
U.S. Appl. No. 17/193,306, filed Mar. 5, 2021 First Named Inventor: Herriot Tabuteau Assignee: Antecip Bioventures II LLC.
U.S. Appl. No. 17/193,340, filed Mar. 5, 2021 First Named Inventor: Herriot Tabuteau Assignee: Antecip Bioventures II LLC.
U.S. Appl. No. 17/194,739, filed Mar. 8, 2021 First Named Inventor: Herriot Tabuteau Assignee: Antecip Bioventures II LLC.
U.S. Appl. No. 17/196,338, filed Mar. 9, 2021 First Named Inventor: Herriot Tabuteau Assignee: Antecip Bioventures II LLC.
U.S. Appl. No. 17/197,971, filed Mar. 10, 2021 First Named Inventor: Herriot Tabuteau Assignee: Antecip Bioventures II LLC.
U.S. Appl. No. 17/199,112, filed Mar. 11, 2021 First Named Inventor: Herriot Tabuteau Assignee: Antecip Bioventures II LLC.
U.S. Appl. No. 17/201,820, filed Mar. 15, 2021 First Named Inventor: Herriot Tabuteau Assignee: Antecip Bioventures II LLC.
U.S. Appl. No. 17/207,256, filed Mar. 19, 2021 First Named Inventor: Herriot Tabuteau Assignee: Antecip Bioventures II LLC.
U.S. Appl. No. 17/217,311, filed Mar. 30, 2021 First Named Inventor: Herriot Tabuteau Assignee: Antecip Bioventures II LLC.
U.S. Appl. No. 17/314,647, filed May 7, 2021 First Named Inventor: Herriot Tabuteau Assignee: Antecip Bioventures II LLC.
U.S. Appl. No. 17/316,194, filed May 10, 2021 First Named Inventor: Herriot Tabuteau Assignee: Antecip Bioventures II LLC.
Communication of Notices of Opposition over European Patent No. 3220909 from European Patent Office dated Jun. 25, 2021.
Sansone et al., "Pain, Pain, Go Away: Antidepressants and Pain Management" Psychiatry (Edgemont), 5(12), Dec. 16-19, 2008.
Matsumoto et al., "Involvement of Sigma-1 Receptors in the Antidepressant-like Effects of Dextromethorphan" PLOS One, 9(2), e89985, Feb. 1-9, 2014.
U.S. Appl. No. 17/929,147, filed Sep. 1, 2022 First Named Inventor: Herriot Tabuteau Assignee: Antecip Bioventures II LLC.
U.S. Appl. No. 17/930,829, filed Sep. 9, 2022 First Named Inventor: Herriot Tabuteau Assignee: Antecip Bioventures II LLC.
Hurt et al., A Comparison of Sustained-Release Bupropion and Placebo for Smoking Cessation, New England Journal of Medicine, 337(17), 1195-202, Oct. 1997.
International Preliminary Report on Patentability with Written Opinion, PCT/US2021/024718, dated Oct. 13, 2022.
Anderson, A. et al., Efficacy and Safety of AXS-05, an Oral NMDA Receptor Antagonist with Multimodal Activity, in Major Depressive Disorder: Results of a Phase 2, Double-Blind, Active-Controlled Trial, W43 ASCP Annual Meeting, May 2019 [retrieved on Nov. 1, 2022], (URL:https://d3dyybxyjb4kyh.cloudfront.net/pdfs/Axsome-AXS-05-Poster-Presentation-ASCP2019.pdf).
O'Gorman, C. et al., AXS-05: A Mechanistically Novel Oral Therapeutic in Development for Neuropsychiatric Disorders, P7-141 APA Annual Meeting, May 2019 [retrieved on Nov. 1, 2022], (URL:https://d3dyybxyjb4kyh.cloudfront.net/pdfs/Axsome-AXS-05-Poster-APA-2019-1.pdf).

O'Gorman, C. et al., AXS-05 (Dextromethorphan/Bupropion): An Innovative Treatment in Clinical Development for Agitation Associated with Alzheimer's Disease, P2-033 AAIC Conference, Jul. 2018 [retrieved on Nov. 1, 2022], URL:https://d3dyybxyjb4kyh.cloudfront.net/pdfs/Axsome-AXS-05-Poster-AAIC-2018-1-1.pdf).
Stahl, S.M., Dextromethorphan/Bupropion: A Novel Oral NMDA (N-methyl-d-aspartate) Receptor Antagonist with Multimodal Activity, CNS Spectrums, vol. 24, Issue 5, pp. 461-466, published online Sep. 30, 2019 [retrieved on Nov. 1, 2022], (D01:10.1017/S1092852919001470).
AXS Pipeline: About AXS-05 [online], AXSOME, retrieved on Nov. 1, 2022 from https://www.axsome.com/axs-portfolio/pipeline/about-axs-05.
International Search Report, PCT/US2021/024718.
U.S. Appl. No. 18/056,804, filed Nov. 18, 2022 First Named Inventor: Herriot Tabuteau Assignee: Antecip Bioventures II LLC.
U.S. Appl. No. 18/056,848, filed Nov. 18, 2022 First Named Inventor: Herriot Tabuteau Assignee: Antecip Bioventures II LLC.
U.S. Appl. No. 18/061,091, filed Dec. 2, 2022 First Named Inventor: Herriot Tabuteau Assignee: Antecip Bioventures II LLC.
U.S. Appl. No. 18/062,236, filed Dec. 6, 2022 First Named Inventor: Herriot Tabuteau Assignee: Antecip Bioventures II LLC.
U.S. Appl. No. 18/062,273, filed Dec. 6, 2022 First Named Inventor: Herriot Tabuteau Assignee: Antecip Bioventures II LLC.
U.S. Appl. No. 18/063,261, filed Dec. 8, 2022 First Named Inventor: Herriot Tabuteau Assignee: Antecip Bioventures II LLC.
U.S. Appl. No. 18/066,739, filed Dec. 15, 2022 First Named Inventor: Herriot Tabuteau Assignee: Antecip Bioventures II LLC.
Cao et al., A Comparative Study of Bupropion in the Treatment of Depression, Chinese Journal of Misdiagnosis, vol. 8, No. 15, p. 3569-3570, May 2008. (English translation also included).
Choi et al., A Study on the Changes of Sexual Dysfunction after Substitution of a Serotonin Reuptake Inhibitor (SRI) with Bupropion Sustained Release in Major Depressive Disorder Patients With SRI-induced Sexual Dysfunction, Journal of the Korean Society of Biological Therapies in Psychiatry, vol. 11, No. 1, p. 62-8, 2005. (English translation also included).
Clinical Trial, NCT00330616, Study of Bupropion SR (323U66) in Patients with Major Depressive Disorder in Japan, accessed in Feb. 2023.
U.S. Appl. No. 18/156,825, filed Jan. 19, 2023 First Named Inventor: Herriot Tabuteau Assignee: Antecip Bioventures II LLC.
U.S. Appl. No. 18/157,266, filed Jan. 20, 2023 First Named Inventor: Herriot Tabuteau Assignee: Antecip Bioventures II LLC.
U.S. Appl. No. 18/157,393, filed Jan. 20, 2023 First Named Inventor: Herriot Tabuteau Assignee: Antecip Bioventures II LLC.
U.S. Appl. No. 18/158,268, filed Jan. 23, 2023 First Named Inventor: Herriot Tabuteau Assignee: Antecip Bioventures II LLC.
U.S. Appl. No. 18/169,571, filed Feb. 15, 2023 First Named Inventor: Herriot Tabuteau Assignee: Antecip Bioventures II LLC.
U.S. Appl. No. 18/170,120, filed Feb. 16, 2023 First Named Inventor: Herriot Tabuteau Assignee: Antecip Bioventures II LLC.
U.S. Appl. No. 18/170,151, filed Feb. 16, 2023 First Named Inventor: Herriot Tabuteau Assignee: Antecip Bioventures II LLC.
U.S. Appl. No. 18/172,555, filed Feb. 22, 2023 First Named Inventor: Herriot Tabuteau Assignee: Antecip Bioventures II LLC.
U.S. Appl. No. 18/172,617, filed Feb. 22, 2023 First Named Inventor: Herriot Tabuteau Assignee: Antecip Bioventures II LLC.
U.S. Appl. No. 18/173,291, filed Feb. 23, 2023 First Named Inventor: Herriot Tabuteau Assignee: Antecip Bioventures II LLC.
U.S. Appl. No. 18/173,372, filed Feb. 23, 2023 First Named Inventor: Herriot Tabuteau Assignee: Antecip Bioventures II LLC.
U.S. Appl. No. 18/174,123, filed Feb. 24, 2023 First Named Inventor: Herriot Tabuteau Assignee: Antecip Bioventures II LLC.
U.S. Appl. No. 18/174,278, filed Feb. 24, 2023 First Named Inventor: Herriot Tabuteau Assignee: Antecip Bioventures II LLC.
U.S. Appl. No. 18/175,862, filed Feb. 28, 2023 First Named Inventor: Herriot Tabuteau Assignee: Antecip Bioventures II LLC.
U.S. Appl. No. 18/175,865, filed Feb. 28, 2023 First Named Inventor: Herriot Tabuteau Assignee: Antecip Bioventures II LLC.
International Search Report, PCT/US2022/074713.
International Written Opinion, PCT/US2022/074713.

(56) References Cited

OTHER PUBLICATIONS

Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021. <URL: https://clinicaltrials.gov/ct2/show/NCT04608396> [retrieved online Mar. 3, 2023].

O'Gorman C et al., "Effects of AXS-05 On Patient Reported Depressive Symptoms in Major Depressive Disorder: Results From the Gemini Trial," Value in Health, Jun. 2021, vol. 24, abstract No. PHM40, p. S135. DOI:10.1016/j.jval.2021.04.662.

Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI:10.1016/j.jval.2021.04.662.

O'Gorman Cedric et al., "Rapid Effects of AXS-05, an Oral NMDA Receptor Antagonist, in Major Depressive Disorder: Results from Two Randomized, Double-Blind, Controlled Trials ," W19 ASCP Annual Meeting, Jun. 1-4, 2021 [retrieved from the Internet on Jul. 6, 2022]. <URL: https://d3dyybxyjb4kyh.cloudfront.net/pdfs/ASCP+2021+AXS-05+Rapid+MDD+Poster+FINAL.pdf>.

Axsome Therapeutics, Inc.: "A Randomized, Double-Blind, Active-Controlled Trial of AXS-05 Administered Orally to Subjects with Major Depressive Disorder ," ClinicalTrials.gov, NCT03595579 version 5, Jul. 30, 2021. <URL https://clinicaltrials.gov/ct2/show/NCT03595579> [retrieved online Mar. 3, 2023].

Auvelity (dextromethorphan hydrobromide and bupropion hydrochloride), Highlights of Prescribing Information and Medication Guide, issued Dec. 2022.

International Preliminary Report on Patentability, PCT/US2021/061492, dated Jun. 15, 2023.

International Search Report and Written Opinion, PCT/US2021/061492 dated Jun. 15, 2023.

International Search Report and Written Opinion, PCT/US2022/012768 dated Jul. 5, 2023.

International Search Report and Written Opinion, PCT/US2023/067062 dated Jul. 12, 2023.

Axsome therapeutics announces topline results of the stride-1 phase 3 trial in treatment resistant depression and expert call to discuss clinical implications, Mar. 2020 (retrieved from internet on Jul. 19, 2023). <axsometherapeuticsinc.gcs-web.com/node/9176/pdf>.

O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+Final.pdf> (Jun. 2021).

O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.

BUPROPION AS A MODULATOR OF DRUG ACTIVITY

CROSS REFERENCE TO RELATED APPLICATIONS

[1] This application is a continuation of U.S. patent application Ser. No. 17/547,050, filed Dec. 9, 2021, now U.S. Pat. No. 11,433,067; which is a continuation-in-part of U.S. patent application Ser. No. 17/066,310, filed Oct. 8, 2020, now U.S. Pat. No. 11,229,640; which is a continuation-in-part of U.S. patent application Ser. No. 16/817,119, filed Mar. 12, 2020, now U.S. Pat. No. 10,813,924; which is a continuation-in-part of U.S. patent application Ser. No. 16/359,996, filed Mar. 20, 2019, now U.S. Pat. No. 10,688,066; which claims the benefit of U.S. Prov. Pat. App. No. 62/645,751, filed Mar. 20, 2018; U.S. patent application Ser. No. 17/066,310 is also a continuation-in-part of U.S. patent application Ser. No. 16/822,697, filed Mar. 18, 2020, now U.S. Pat. No. 11,090,300; which is a continuation-in-part of U.S. patent application Ser. No. 16/359,958, filed Mar. 20, 2019, now U.S. Pat. No. 10,881,657; which is a continuation-in-part of U.S. patent application Ser. No. 15/821,563, filed Nov. 22, 2017, now U.S. Pat. No. 10,512,643; which is a continuation-in-part of U.S. patent application Ser. No. 15/645,939, filed Jul. 10, 2017, now U.S. Pat. No. 9,867,819; which is a continuation-in-part of U.S. patent application Ser. No. 15/263,138, filed on Sep. 12, 2016, now U.S. Pat. No. 9,700,553; which is a continuation of U.S. patent application Ser. No. 15/164,746, filed on May 25, 2016, now U.S. Pat. No. 9,457,023; which is a continuation-in-part of U.S. patent application Ser. No. 14/879,002, filed Oct. 8, 2015, now U.S. Pat. No. 9,375,429; which is a continuation of U.S. patent application Ser. No. 14/554,988, filed Nov. 26, 2014, now U.S. Pat. No. 9,205,083; which is a continuation of U.S. patent application Ser. No. 14/550,618, filed Nov. 21, 2014, now U.S. Pat. No. 9,198,905; which is a continuation-in-part of International Pat. App. No. PCT/US2014/064184, filed Nov. 5, 2014; which claims the benefit of U.S. Prov. Pat. App. No. 61/900,354, filed Nov. 5, 2013; U.S. patent application Ser. No. 15/821,563 also claims the benefit of U.S. Prov. Pat. App. No. 62/576,538, filed Oct. 24, 2017; all of the above applications, U.S. patents issued from, or U.S. publications of any of the above applications are incorporated by reference in their entirety.

SUMMARY

Some embodiments include a method of increasing dextromethorphan plasma levels in a human being, comprising co-administering bupropion, hydroxybupropion, erythrohydroxybupropion, threohydroxybupropion, or a metabolite or prodrug of any of these compounds with dextromethorphan.

Some embodiments include a method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in an $AUC_{0-12}$ of dextromethorphan that is at least about 40 ng·hr/mL.

Some embodiments include a method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in a $C_{max}$ of dextromethorphan that is at least about 6 ng/mL.

Some embodiments include a method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in a $C_{avg}$ of dextromethorphan, over the period between two separate and consecutive administrations of dextromethorphan, that is at least about 5 ng/mL.

Some embodiments include a method of increasing the metabolic lifetime of dextromethorphan, comprising administering threohydroxybupropion, or a prodrug thereof, to a human being in need of treatment with dextromethorphan, wherein the human being is an extensive metabolizer of dextromethorphan, and wherein dextromethorphan is present in the body of the human being at the same time as threohydroxybupropion.

Some embodiments include a method of reducing an adverse event associated with treatment by dextromethorphan, comprising co-administering threohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include an oral sustained release delivery system for dextromethorphan, comprising bupropion, hydroxybupropion, erythrohydroxybupropion, threohydroxybupropion, or a prodrug of any of these compounds, dextromethorphan, and a water soluble vehicle.

Some embodiments include a method of decreasing the number of doses of dextromethorphan that can be administered without loss of efficacy, comprising orally administering an effective amount of bupropion, hydroxybupropion, erythrohydroxybupropion, threohydroxybupropion, or a prodrug of any of these compounds, to a human being in need of treatment with dextromethorphan.

Some embodiments include a method of decreasing dextrorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of treatment with dextromethorphan, wherein a decrease in the dextrorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of decreasing dextrorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of treatment with dextromethorphan, wherein a decrease in the dextrorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of decreasing dextrorphan plasma levels comprising co-administering bupropion and dextromethorphan to a human being in need of treatment with dextromethorphan, wherein the bupropion is administered on the first day of at least two days of treatment with dextromethorphan, wherein a decrease in the dextrorphan plasma level occurs on the first day that bupropion and dextromethorphan are co-administered, as compared to the same amount of dextromethorphan administered without bupropion.

Some embodiments include a method of decreasing dextrorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of treatment with dextromethorphan, wherein a decrease in the dextrorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of decreasing dextrorphan plasma levels comprising co-administering bupropion and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion for eight consecutive days.

Some embodiments include a method of decreasing dextrorphan plasma levels comprising co-administering hydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without hydroxybupropion, or a prodrug thereof, for eight consecutive days.

Some embodiments include a method of decreasing dextrorphan plasma levels comprising co-administering erythrohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without erythrohydroxybupropion, or a prodrug thereof, for eight consecutive days.

Some embodiments include a method of decreasing dextrorphan plasma levels comprising co-administering threohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without threohydroxybupropion, or a prodrug thereof, for eight consecutive days.

Some embodiments include a method of decreasing dextrorphan plasma levels comprising co-administering bupropion and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion for nine consecutive days.

Some embodiments include a method of decreasing dextrorphan plasma levels comprising co-administering hydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without hydroxybupropion, or a prodrug thereof, for nine consecutive days.

Some embodiments include a method of decreasing dextrorphan plasma levels comprising co-administering erythrohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without erythrohydroxybupropion, or a prodrug thereof, for nine consecutive days.

Some embodiments include a method of decreasing dextrorphan plasma levels comprising co-administering threohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without threohydroxybupropion, or a prodrug thereof, for nine consecutive days.

Some embodiments include a method of decreasing dextrorphan plasma levels comprising co-administering bupropion and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion for nine consecutive days.

Some embodiments include a method of decreasing dextrorphan plasma levels comprising co-administering hydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without hydroxybupropion, or a prodrug thereof, for nine consecutive days.

Some embodiments include a method of decreasing dextrorphan plasma levels comprising co-administering erythrohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without erythrohydroxybupropion, or a prodrug thereof, for nine consecutive days.

Some embodiments include a method of decreasing dextrorphan plasma levels comprising co-administering threohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without threohydroxybupropion, or a prodrug thereof, for nine consecutive days.

Some embodiments include a method of decreasing dextrorphan plasma levels comprising co-administering bupropion and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion for nine consecutive days.

Some embodiments include a method of decreasing dextrorphan plasma levels comprising co-administering hydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without hydroxybupropion, or a prodrug thereof, for nine consecutive days.

Some embodiments include a method of decreasing dextrorphan plasma levels comprising co-administering erythrohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without erythrohydroxybupropion, or a prodrug thereof, for nine consecutive days.

Some embodiments include a method of decreasing dextrorphan plasma levels comprising co-administering threohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without threohydroxybupropion, or a prodrug thereof, for nine consecutive days.

Some embodiments include a method of decreasing dextrorphan plasma levels comprising co-administering bupropion and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without bupropion for ten consecutive days.

Some embodiments include a method of decreasing dextrorphan plasma levels comprising co-administering hydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without hydroxybupropion, or a prodrug thereof, for ten consecutive days.

Some embodiments include a method of decreasing dextrorphan plasma levels comprising co-administering erythrohydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without erythrohydroxybupropion, or a prodrug thereof, for ten consecutive days.

Some embodiments include a method of decreasing dextrorphan plasma levels comprising co-administering threohydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without threohydroxybupropion, or a prodrug thereof, for ten consecutive days.

Antidepressant compounds, such as bupropion, hydroxybupropion, erythrohydroxybupropion, threohydroxybupropion, or a metabolite or prodrug of any of these compounds, can be used to improve the therapeutic properties, such as in the treatment of neurological disorders, of dextromethorphan. Bupropion, hydroxybupropion, erythrohydroxybupropion, threohydroxybupropion, or a metabolite or prodrug of any of these compounds, regardless of stereochemistry, can be effective in inhibiting or reducing the metabolism of dextromethorphan in some human beings. This may be accomplished by co-administering bupropion, hydroxybupropion, erythrohydroxybupropion, threohydroxybupropion, or a metabolite or prodrug of any of these compounds, and dextromethorphan.

Some embodiments include a method of treating a neurological disorder comprising administering: 1) dextromethorphan, or 2) a combination of an antidepressant compound and dextromethorphan to a human being in need thereof, wherein the human being is an extensive metabolizer of dextromethorphan.

Some embodiments include a method of increasing dextromethorphan plasma levels in a human being in need of treatment with dextromethorphan, wherein the human being is an extensive metabolizer of dextromethorphan, comprising co-administering bupropion with dextromethorphan to the human being.

Some embodiments include a method of inhibiting the metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of increasing the metabolic lifetime of dextromethorphan, comprising administering bupropion to a human being in need of treatment with dextromethorphan, wherein the human being is an extensive metabolizer of dextromethorphan, and wherein dextromethorphan is present in the body of the human being at the same time as bupropion.

Some embodiments include a method of correcting extensive metabolism of dextromethorphan, comprising administering bupropion to a human being in need thereof.

Some embodiments include a method of improving the antitussive properties of dextromethorphan comprising administering bupropion in conjunction with administration of dextromethorphan to a human being in need of treatment for cough.

Some embodiments include a method of treating cough comprising administering a combination of bupropion or another active compound and dextromethorphan to a human being in need thereof.

Some embodiments include a method of treating a neurological disorder comprising administering 1) dextromethorphan, or 2) bupropion and dextromethorphan to a human being in need thereof, wherein the 1) dextromethorphan, or 2) bupropion and dextromethorphan are administered at least once a day for at least 8 days, at least 9 days, or at least 10 days.

Some embodiments include a method of treating a neurological disorder comprising administering about 150 mg/day to about 300 mg/day of bupropion and about 15 mg/day to about 60 mg/day of dextromethorphan to a human being in need thereof.

Some embodiments include a method of increasing dextromethorphan plasma levels in a human being in need of treatment with dextromethorphan, wherein the human being is an extensive metabolizer of dextromethorphan, comprising co-administering hydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering erythrohydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering threohydroxybupropion, or a prodrug thereof, with dextromethorphan to the human being.

Some embodiments include a method of inhibiting metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of inhibiting metabolism of dextromethorphan, comprising administering hydroxybupropion, or a prodrug thereof, to a human being, wherein the human being is an extensive metabolizer of dextromethorphan, and wherein dextromethorphan is present in the body of the human being at the same time as hydroxybupropion.

Some embodiments include a method of inhibiting metabolism of dextromethorphan, comprising administering erythrohydroxybupropion, or a prodrug thereof, to a human being, wherein the human being is an extensive metabolizer of dextromethorphan, and wherein dextromethorphan is present in the body of the human being at the same time as erythrohydroxybupropion.

Some embodiments include a method of inhibiting metabolism of dextromethorphan, comprising administering threohydroxybupropion, or a prodrug thereof, to a human being, wherein the human being is an extensive metabolizer of dextromethorphan, and wherein dextromethorphan is present in the body of the human being at the same time as threohydroxybupropion.

Some embodiments include a method of increasing the metabolic lifetime of dextromethorphan, comprising administering hydroxybupropion, or a prodrug thereof, to a human being in need of treatment with dextromethorphan, wherein the human being is an extensive metabolizer of dextromethorphan, and wherein dextromethorphan is present in the body of the human being at the same time as hydroxybupropion.

Some embodiments include a method of increasing the metabolic lifetime of dextromethorphan, comprising administering erythrohydroxybupropion, or a prodrug thereof, to a human being in need of treatment with dextromethorphan, wherein the human being is an extensive metabolizer of dextromethorphan, and wherein dextromethorphan is present in the body of the human being at the same time as erythrohydroxybupropion.

Some embodiments include a method of increasing dextromethorphan plasma levels comprising co-administering bupropion and dextromethorphan to a human being in need of treatment with dextromethorphan, wherein the bupropion is administered on the first day of at least two days of co-administration of bupropion with dextromethorphan, wherein an increase in the dextromethorphan plasma level occurs on the first day that bupropion and dextromethorphan are co-administered, as compared to the same amount of dextromethorphan administered without bupropion.

Some embodiments include a method of increasing dextromethorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of co-administration of hydroxybupropion, or a prodrug thereof, with dextromethorphan, wherein an increase in the dextromethorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of increasing dextromethorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of co-administration of erythrohydroxybupropion, or a prodrug thereof, with dextromethorphan, wherein an increase in the dextromethorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of increasing dextromethorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of co-administration of threohydroxybupropion, or a prodrug thereof, with dextromethorphan, wherein an increase in the dextromethorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of increasing dextromethorphan plasma levels comprising co-administering bupropion and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion for five consecutive days.

Some embodiments include a method of increasing dextromethorphan plasma levels comprising co-administering hydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without hydroxybupropion, or a prodrug thereof, for five consecutive days.

Some embodiments include a method of increasing dextromethorphan plasma levels comprising co-administering erythrohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without erythrohydroxybupropion, or a prodrug thereof, for five consecutive days.

Some embodiments include a method of increasing dextromethorphan plasma levels comprising co-administering threohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without threohydroxybupropion, or a prodrug thereof, for five consecutive days.

Some embodiments include a method of increasing dextromethorphan plasma levels comprising co-administering bupropion and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion for six consecutive days.

Some embodiments include a method of increasing dextromethorphan plasma levels comprising co-administering hydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without hydroxybupropion, or a prodrug thereof, for six consecutive days.

Some embodiments include a method of increasing dextromethorphan plasma levels comprising co-administering erythrohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without erythrohydroxybupropion, or a prodrug thereof, for six consecutive days.

Some embodiments include a method of increasing dextromethorphan plasma levels comprising co-administering threohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without threohydroxybupropion, or a prodrug thereof, for six consecutive days.

Some embodiments include a method of reducing a trough effect of dextromethorphan comprising, co-administering bupropion with dextromethorphan to a human patient in need of treatment with dextromethorphan, wherein dextromethorphan has a plasma level 12 hours after co-administering bupropion with dextromethorphan that is at least twice the plasma level that would be achieved by administering the same amount of dextromethorphan without bupropion.

Some embodiments include a method of reducing a trough effect of dextromethorphan comprising, co-administering hydroxybupropion, or a prodrug thereof, with dextromethorphan to a human patient in need of treatment with dextromethorphan, wherein dextromethorphan has a plasma level 12 hours after co-administering hydroxybupropion, or a prodrug thereof, with dextromethorphan that is at least twice the plasma level that would be achieved by administering the same amount of dextromethorphan without hydroxybupropion or a prodrug thereof.

Some embodiments include a method of reducing a trough effect of dextromethorphan comprising, co-administering erythrohydroxybupropion, or a prodrug thereof, with dextromethorphan to a human patient in need of treatment with dextromethorphan, wherein dextromethorphan has a plasma level 12 hours after co-administering erythrohydroxybupropion, or a prodrug thereof, with dextromethorphan that is at least twice the plasma level that would be achieved by administering the same amount of dextromethorphan without erythrohydroxybupropion or a prodrug thereof.

Some embodiments include a method of reducing a trough effect of dextromethorphan comprising, co-administering threohydroxybupropion, or a prodrug thereof, with dextromethorphan to a human patient in need of treatment with dextromethorphan, wherein dextromethorphan has a plasma level 12 hours after co-administering threohydroxybupropion, or a prodrug thereof, with dextromethorphan that is at least twice the plasma level that would be achieved by administering the same amount of dextromethorphan without threohydroxybupropion or a prodrug thereof.

Some embodiments include a method of reducing an adverse event associated with treatment by dextromethorphan, comprising co-administering bupropion and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering hydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering erythrohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by bupropion, comprising co-administering dextromethorphan and bupropion to a human patient in need of bupropion treatment, wherein the human patient is at risk of experiencing the adverse event as a result of being treated with bupropion.

Some embodiments include a method of correcting extensive metabolism of dextromethorphan, comprising administering hydroxybupropion, or a prodrug thereof, to a human being in need thereof.

Some embodiments include a method of correcting extensive metabolism of dextromethorphan, comprising administering erythrohydroxybupropion, or a prodrug thereof, to a human being in need thereof.

Some embodiments include a method of correcting extensive metabolism of dextromethorphan, comprising administering threohydroxybupropion, or a prodrug thereof, to a human being in need thereof.

Some embodiments include a method of improving antitussive properties of dextromethorphan comprising administering bupropion in conjunction with administration of dextromethorphan to a human being in need of treatment for cough.

Some embodiments include a method of improving antitussive properties of dextromethorphan comprising administering hydroxybupropion, or a prodrug thereof, in conjunction with administration of dextromethorphan to a human being in need of treatment for cough.

Some embodiments include a method of improving antitussive properties of dextromethorphan comprising administering erythrohydroxybupropion, or a prodrug thereof, in conjunction with administration of dextromethorphan to a human being in need of treatment for cough.

Some embodiments include a method of improving antitussive properties of dextromethorphan comprising administering threohydroxybupropion, or a prodrug thereof, in conjunction with administration of dextromethorphan to a human being in need of treatment for cough.

Some embodiments include a method of treating cough comprising administering a combination of hydroxybupropion, or a prodrug thereof, and dextromethorphan to a human being in need thereof.

Some embodiments include a method of treating cough comprising administering a combination of erythrohydroxybupropion, or a prodrug thereof, and dextromethorphan to a human being in need thereof.

Some embodiments include a method of treating cough comprising administering a combination of threohydroxybupropion, or a prodrug thereof, and dextromethorphan to a human being in need thereof.

Some embodiments include a method of treating a neurological disorder comprising administering bupropion and dextromethorphan to a human being in need thereof, wherein the bupropion and dextromethorphan are administered at least once a day for at least 8 days, at least 9 days, or at least 10 days.

Some embodiments include a method of treating a neurological disorder comprising administering hydroxybupropion, or a prodrug thereof, and dextromethorphan to a human being in need thereof, wherein the bupropion and dextromethorphan are administered at least once a day for at least 8 days, at least 9 days, or at least 10 days.

Some embodiments include a method of treating a neurological disorder comprising administering erythrohydroxybupropion, or a prodrug thereof, and dextromethorphan to a human being in need thereof, wherein the erythrohydroxybupropion and dextromethorphan are administered at least once a day for at least 8 days, at least 9 days, or at least 10 days.

Some embodiments include a method of treating a neurological disorder comprising administering threohydroxybupropion, or a prodrug thereof, and dextromethorphan to a human being in need thereof, wherein the threohydroxybupropion and dextromethorphan are administered at least once a day for at least 8 days, at least 9 days, or at least 10 days.

Some embodiments include a pharmaceutical composition, dosage form, or medicament comprising a therapeutically effective amount of dextromethorphan, a therapeutically effective amount of an antidepressant, such as bupropion, hydroxybupropion, erythrohydroxybupropion, threohydroxybupropion, or a metabolite or prodrug of any of these compounds, and a pharmaceutically acceptable excipient.

Some embodiments include a method of reducing a risk of seizure associated with use of bupropion to treat depression, comprising orally administering a dextromethorphan-bupropion combination twice a day, wherein the method is: 1) at least as effective in treating depression, and 2) reduces the risk of seizure to the human being, as compared to orally administering 150 mg of the bupropion alone twice a day to the human being for the same number of days.

Some embodiments include a method of improving the therapeutic effect of bupropion in treating depression, comprising orally co-administering a dextromethorphan with a bupropion, twice a day, to a human being suffering from depression, wherein the method is more effective than treating the depression of that human being by orally administering 150 mg of the bupropion alone twice a day to the human being for five weeks.

In some embodiments, the combination of the dextromethorphan and the bupropion is more effective than independently orally administering the same amount of the dextromethorphan or the bupropion alone.

Some embodiments include a method of improving the efficacy of bupropion in treating depression, comprising orally administering about 90 mg to about 125 mg of a bupropion in combination with about 0.3 mg/kg to about 1 mg/kg of a dextromethorphan, once or twice a day for at least 23 days, to a human being suffering from depression, wherein orally administering the bupropion in combination with the dextromethorphan is more effective in treating depression than orally administering the same dosage regimen of bupropion without dextromethorphan.

Some embodiments include a method of treating treatment-resistant depression comprising: selecting a human being suffering from depression who has previously been unsuccessfully treated with at least one antidepressant; and orally administering a dextromethorphan-bupropion combination treatment once or twice a day to the human being for at least about five weeks; wherein the dextromethorphan-bupropion combination treatment comprises about 40 mg to about 70 mg of a dextromethorphan and about 100 mg to about 140 mg of a bupropion.

Some embodiments include a method of rapidly relieving the symptoms of depression, comprising administering a combination of bupropion and dextromethorphan once daily or twice daily to a human being in need thereof, wherein the human being experiences a therapeutic effect within 2 weeks of the first day that the combination of bupropion and dextromethorphan is administered.

Some embodiments include a method of treating depression, comprising administering a combination of bupropion and dextromethorphan once daily or twice daily to a human being in need thereof, wherein the human being is of Asian descent.

Some embodiments include a method of treating nicotine addiction associated with smoking tobacco comprising administering a combination of a bupropion and a dextromethorphan daily for at least 21 consecutive days to a person suffering from nicotine addiction, wherein the person is an ad-lib tobacco smoker, wherein a total amount of 200 mg to 250 mg of bupropion and 80 mg to 140 mg of dextromethorphan are administered to the person daily, and wherein the method is more effective than administering the same amount of bupropion alone.

In some embodiments involving treating nicotine addiction, administration of the combination of the bupropion and the dextromethorphan results in at least 20% greater reduction in an intensity of the nicotine self-administration as compared to bupropion alone as measured by the reduction in the average number of cigarettes smoked per day.

In some embodiments involving treating nicotine addiction, administration of the combination of the bupropion and the dextromethorphan results in at least 10% greater reduction in expired carbon monoxide levels as compared to bupropion alone.

In some embodiments involving treating nicotine addiction, administering the combination of the bupropion and the dextromethorphan twice a day in 2 equal divided doses results in a greater reduction in intensity of nicotine self-administration at a particular timepoint, such as 1 week, 2 weeks, 3 weeks, 4 weeks, or another timepoint recited herein, than would have resulted from administering one of the 2 divided doses for the same amount of time, or than would have resulted from not administering the combination.

DETAILED DESCRIPTION

Figure 1:
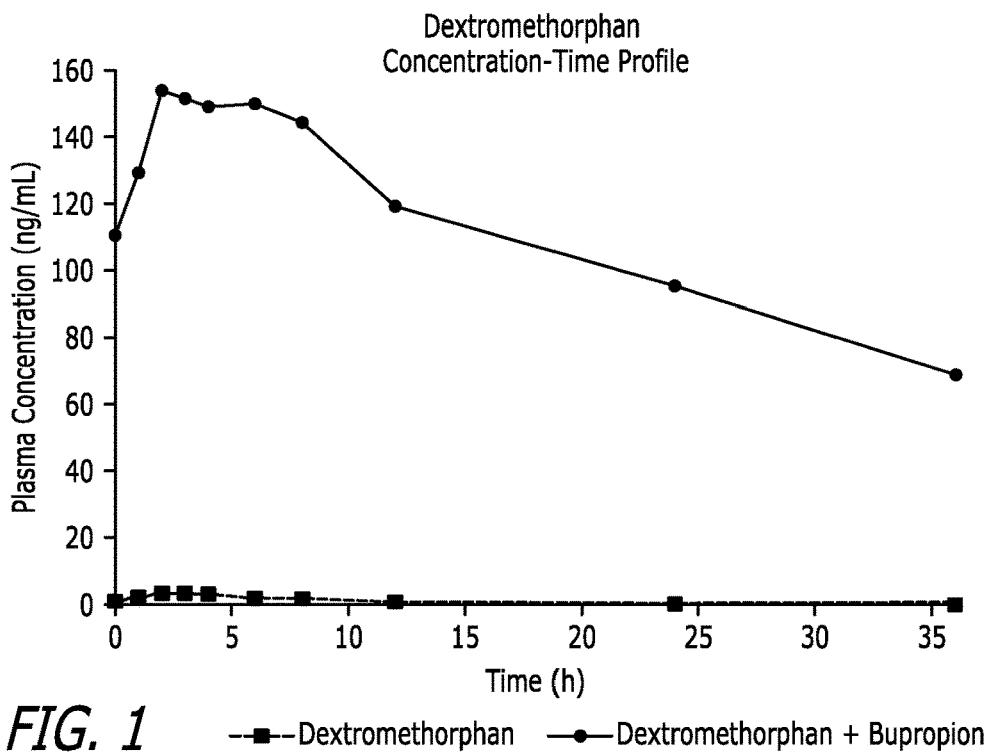
FIG. 1 is a plot of the mean plasma concentrations of dextromethorphan over time after dosing on Day 8 for subjects administered dextromethorphan alone or dextromethorphan and bupropion.

Some embodiments include a method of treating neurological disorders comprising administering a therapeutically effective amount of dextromethorphan and a therapeutically effective amount of an antidepressant, such as bupropion, hydroxybupropion, erythrohydroxybupropion, threohydroxybupropion, or a metabolite or prodrug of any of these compounds, to a person in need thereof.

Some embodiments include a method of enhancing the therapeutic properties of dextromethorphan in treating neurological disorders, comprising co-administering dextromethorphan and an antidepressant, such as bupropion, hydroxybupropion, erythrohydroxybupropion, threohydroxybupropion, or a metabolite or prodrug of any of these compounds.

Some embodiments include a method of increasing dextromethorphan plasma levels in a human being that is an extensive metabolizer of dextromethorphan, comprising co-administering an antidepressant compound, such as bupropion, and dextromethorphan to the human being.

Some embodiments include a method of inhibiting the metabolism of dextromethorphan, comprising administering an antidepressant compound, such as bupropion, to a human being, wherein the human being is an extensive metabolizer of dextromethorphan, and wherein dextromethorphan is present in the body of the human being at the same time as the antidepressant.

Some embodiments include a method of increasing the metabolic lifetime of dextromethorphan, including increasing the elimination half-life ($T_{1/2}$) of dextromethorphan. These embodiments may comprise administering an antidepressant compound, such as bupropion, to a human being, wherein the human being is an extensive metabolizer of dextromethorphan, and wherein dextromethorphan is present in the body of the human being at the same time as the antidepressant compound.

Some embodiments include a method of correcting extensive metabolism of dextromethorphan, comprising administering an antidepressant compound, such as bupropion, to a human being in need thereof, such as a human being in need of treatment for pain.

Some embodiments include a method of improving the therapeutic properties of dextromethorphan in treating neurological disorders comprising administering an antidepressant compound, such as bupropion, in conjunction with administration of dextromethorphan to a human being in need of treatment for a neurological disorder.

Some embodiments include a method of treating neurological disorders comprising administering a combination of an antidepressant compound, such as bupropion, and dextromethorphan to a human being in need thereof.

Co-administration of an antidepressant compound, such as bupropion, hydroxybupropion, threohydroxybupropion, erythrohydroxybupropion, or a prodrug of the antidepressant compound, with dextromethorphan may occur one or more times for a single day, or for 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 100, or more consecutive days. In some embodiments, co-administration is at least daily for at least two consecutive days.

In some embodiments, co-administration of an antidepressant compound, such as bupropion, hydroxybupropion, threohydroxybupropion, erythrohydroxybupropion, or a prodrug of the antidepressant compound, with dextromethorphan may occur once a day for 1, 2, 3, 4, 5, 6, or 7 days, prior to co-administration twice a day.

Dextromethorphan has the structure shown below.

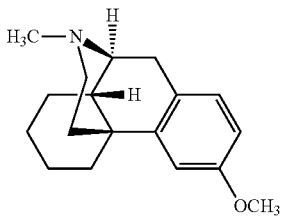

Dextromethorphan is used as a cough suppressant. According to the FDA's dextromethorphan product labeling requirement under the OTC Monograph [21CFR341.74], dextromethorphan should be dosed 6 times a day (every 4 hours), 4 times a day (every 6 hours), or 3 times a day (every 8 hours). The OTC Monograph [21CFR341.74] also states that "the dosage is equivalent to dextromethorphan hydrobromide . . . [o]ral dosage is 10 to 20 milligrams every 4 hours or 30 milligrams every 6 to 8 hours, not to exceed 120 milligrams in 24 hours, or as directed by a doctor."

Dextromethorphan is rapidly metabolized in the human liver. This rapid hepatic metabolism may limit systemic drug exposure in individuals who are extensive metabolizers. Human beings can be: 1) extensive metabolizers of dextromethorphan—those who rapidly metabolize dextromethorphan; 2) poor metabolizers of dextromethorphan—those who only poorly metabolize dextromethorphan; or 3) intermediate metabolizers of dextromethorphan—those whose metabolism of dextromethorphan is somewhere between that of an extensive metabolizer and a poor metabolizer. Extensive metabolizers can also be ultra-rapid metabolizers. Extensive metabolizers of dextromethorphan are a significant portion of the human population. Dextromethorphan can, for example, be metabolized to dextrorphan.

When given the same oral dose of dextromethorphan, plasma levels of dextromethorphan are significantly higher in poor metabolizers or intermediate metabolizers as compared to extensive metabolizers of dextromethorphan. The low plasma concentrations of dextromethorphan can limit its clinical utility as a single agent for extensive metabolizers, and possibly intermediate metabolizers, of dextromethorphan. Some therapeutically active compounds, including antidepressants such as bupropion, inhibit the metabolism of dextromethorphan, and raise the plasma concentration of dextromethorphan, and can thus improve its therapeutic efficacy. Similarly, antidepressants may allow dextromethorphan to be given less often, such as once a day instead of twice a day, once a day instead of three times a day, once a day instead of four times a day, twice a day instead of three times a day, or twice a day instead of four times a day, without loss of therapeutic efficacy.

Co-administration of an antidepressant such as bupropion, hydroxybupropion, erythrohydroxybupropion, threohydroxybupropion, or a metabolite or prodrug of any of these compounds, with dextromethorphan or dextrorphan may enhance the mechanisms of action, or pharmacological properties of dextromethorphan and dextrorphan. Mechanisms of action of dextromethorphan and dextrorphan can include sigma-1 agonist and NMDA antagonist properties, calcium channel blockade, muscarinic binding, serotonin transporter (5HTT) inhibition, and mu receptor potentiation.

Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to agonize, antagonize, or modulate a sigma-1 receptor, or an NMDA receptor; to block a calcium channel; to bind to a muscarinic receptor; to inhibit a serotonin transporter (5HTT); or to potentiate a mu receptor.

Pharmacological properties of dextromethorphan and dextrorphan can include NMDA high-affinity site, NMDR-2A, and functional NMDR-2B receptor antagonism, sigma-1 stimulation, putative mTOR activation (by sigma-1 stimulation, mu potentiation, beta adrenoreceptor stimulation, and 5HTT inhibition), putative AMPA receptor trafficking (by mTOR activation, PCP antagonism, sigma-1 stimulation, beta stimulation, mu potentiation, and 5HTT inhibition), and dendritogenesis, spinogenesis, synaptogenesis, and neuronal survival by NMDA antagonism and sigma-1 and mTOR signaling. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate an NMDA high-affinity site, NMDR-2A, a functional NMDR-2B receptor, sigma-1 receptor, a putative mTOR receptor (such as by stimulating sigma-1, potentiating a mu receptor, stimulating a beta adrenoreceptor, or inhibiting a 5HTT), or a putative AMPA receptor (such as by activating mTOR, antagonizing PCP activity, stimulating a sigma-1 receptor, stimulating a beta adrenergic receptor, potentiating a mu receptor, or inhibiting 5HTT). Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to cause, increase, decrease, or otherwise modulate dendritogenesis, spinogenesis, or synaptogenesis. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to cause, increase, decrease, or otherwise modulate neuronal survival by NMDA antagonism and/or sigma-1 and/or mTOR signaling.

Pharmacological properties of dextromethorphan and dextrorphan can include 5HTT and norepinephrine transporter inhibition, sigma-1 stimulation, NMDA and PCP antagonism, and possible serotonin 5HT1b/d receptor stimulation. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate the 5HTT and/or norepinephrine transporter, the sigma-1 receptor, NMDA and/or PCP receptor, and/or to stimulate the serotonin 5HT1b/d receptor.

Additional properties for dextromethorphan and dextrorphan can include possible presynaptic alpha-2 adrenoreceptor antagonism or postsynaptic alpha-2 stimulation, beta stimulation and possible muscarinic and mu antagonism. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate a presynaptic alpha-2 adrenoreceptor, postsynaptic alpha-2 receptor, beta adrenoreceptor, muscarinic receptor, or mu receptor. Dextromethorphan and dextrorphan may be glial cell modulators. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to modulate glial cells.

Pain or other neurological disorders may be treated by enhancing dextromethorphan plasma levels or increasing dextromethorphan bioavailability, for example by a method comprising administering a therapeutically effective amount of dextromethorphan and a therapeutically effective amount of an antidepressant compound, such as bupropion, hydroxybupropion, erythrohydroxybupropion, threohydroxybupropion, or a metabolite or prodrug of any of these compounds, to a person in need thereof.

Examples of neurological disorders that may be treated, or that may be treated with increased efficacy, by enhanced dextromethorphan levels, such as those achievable by a combination of dextromethorphan and an antidepressant such as bupropion, hydroxybupropion, erythrohydroxybupropion, threohydroxybupropion, or a metabolite or prodrug of any of these compounds, include, but are not limited to: affective disorders, psychiatric disorders, cerebral function disorders, movement disorders, dementias, motor neuron diseases, neurodegenerative diseases, seizure disorders, and headaches.

Affective disorders that may be treated by enhanced dextromethorphan levels or by a combination of dextromethorphan and an antidepressant such as bupropion, hydroxybupropion, erythrohydroxybupropion, threohydroxybupropion, or a metabolite or prodrug of any of these compounds, include, but are not limited to, depression, major depression, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Some patients, even after treatment with medications such as antidepressants, may have an inadequate or no response to the treatment. Treatment resistant depression (TRD), or treatment-refractory depression, is a condition generally associated with patients who have failed treatment with at least two antidepressants. Part of the diagnosis for TRD is for the patient to have had an inadequate response to treatment with the antidepressants after an adequate dose and adequate course, e.g., in the current depressive episode. TRD may be more difficult to treat due to the comorbidity of other medical or psychological illnesses, such as drug/alcohol abuse or eating disorders, or TRD being misdiagnosed. Some TRD patients have had an inadequate response to 1, 2, 3, or more adequate antidepressant treatment trials or have failed or had an inadequate response to 1, 2, 3, or more prior antidepressant treatments. In some embodiments, a patient being treated for treatment resistant depression has failed treatment with at least 1, 2, 3, 4, 5, 6, 7, 8, 9, 10, or more antidepressant therapies.

Measures of treatment effect that may be improved by treatment with enhanced bioavailability or plasma levels of dextromethorphan, or by a combination of dextromethorphan and an antidepressant, such as bupropion, hydroxybupropion, erythrohydroxybupropion, threohydroxybupropion, or a metabolite or prodrug of any of these compounds, include, but are not limited to: Montgomery-Asberg Depression Rating Scale (MADRS), Quality of Life Enjoyment and Satisfaction Questionnaire Short Form, Range of Impaired Functioning Tool, Sheehan Disability Scale, Patient Rated Inventory of Side Effects (PRISE), Columbia-Suicide Severity Rating Scale (C-SSRS), Quick Inventory of Depressive Symptomatology, Self-Report (QIDS-SR), Clinical Global Impression (CGI) scale, Massachusetts General Hospital Cognitive and Physical Functioning Questionnaire (CPFQ), 17-item Hamilton Rating Scale for Depression (HAM-D17), Massachusetts General Hospital Antidepressant Treatment Response Questionnaire (MGH ATRQ), 16-item Quick Inventory of Depressive Symptomatology-Self Report (QIDS-SR16), Sheehan Disability Scale (SDS), Clinical Global Impression of Severity of Illness (CGI-S), Clinical Global Impression of Change (CGI-C), EuroQOL 5 Dimension 5 Level (EQ-5D-5L), Patient Global Impression of Change (PGIC), 7-item Generalized Anxiety Disorder (GAD-7), Clinical Global Impressions-Improvement (CGI-I). Sheehan Disability Scale (SDS). 16-item Quick Inventory of Depressive Symptomatology-Self Report (QIDS-SR16), Hamilton Anxiety Scale (HAM-A), Massachusetts General Hospital Cognitive and Physical Functioning Questionnaire (CPFQ), CPFQ-Cognitive subscales (Items 4 to 7), Brief Psychiatric Rating Scale (BPRS), etc.; Digit Symbol Substitution Test (DSST), Rey Auditory Verbal Learning Task (RAVLT), Trail Making Test (TMT), Stroop Colour Naming Test (STROOP), Simple Reaction Time (SRT), Choice Reaction Time (CRT). etc. In some embodiments, treating a person with a combination of dextromethorphan and bupropion may improve (e.g. reduce) the person's score in one of the above assessments by at least about 10%, at least about 20%, at least about 30%, at least about 40%, at least about 50%, about 10-20%, about 20-30%, about 30-40%, about 40-50%, about 5-15%, about 15-25%, about 25-35%, about 35-45%, about 45-55%, about 50-60%, about 60-70%, about 70-80%, about 80-90%, about 90-100% as compared to baseline or placebo. In some embodiments, the improvement is compared to baseline. In some embodiments, the improvement is compared to placebo.

Administering a combination of bupropion and dextromethorphan may result in a rapid treatment effect, e.g., within about 1 week, within about 2 weeks, within about 3 weeks, or within about 4 weeks of beginning the treatment. For example, an improvement in any of the assessments described herein, including, but not limited to MADRS, Quality of Life Enjoyment and Satisfaction Questionnaire Short Form, Range of Impaired Functioning Tool, PRISE, C-SSRS, QIDS-SR), CGI, CPFQ, HAM-D17, MGH ATRQ, CGI-S, CGI-C, EQ-5D-5L, PGIC, GAD-7, CGI-I, SDS, QIDS-SR16, HAM-A, CPFQ, CPFQ-Cognitive subscales (Items 4 to 7), BPRS, DSST, RAVLT, TMT, STROOP, SRT, CRT, etc., may be observed within those time periods.

In some embodiments, an enhanced bioavailability of dextromethorphan, or a combination of dextromethorphan and an antidepressant such as bupropion, hydroxybupropion, erythrohydroxybupropion, threohydroxybupropion, or a metabolite or prodrug of any of these compounds, may have an onset of action within 30 minutes, 1 hour, 2 hours, 3 hours, 4 hours, 5 hours, 6 hours, 6-8 hours, 8-12 hours, 12 hours, a day, 1-7 days, 1 week, two weeks, three weeks, four weeks, six weeks, or eight weeks.

Patients who may benefit from the treatments described herein include pediatric patients, such as patients under about 18 years of age, about 0-5 years of age, about 5-10 years of age, about 10-12 years of age, or about 12-18 years of age; adult patients, such as patients having an age of about 18-70 years, about 18-65 years, about 18-30 years, about 10-20 years, about 20-30 years, about 30-40 years, about 40-50 years, about 50-60 years, about 60-70 years, about 70-80 years, about 80-90 years, about 30-50 years, about 50-65 years; elderly patients, such as patients over 65 years of age, about 65-75 years of age, about 75-90 years of age, or over 90 years of age; and about 41 years of age or older.

In some embodiments, the human being that is treated with a combination of dextromethorphan and bupropion, e.g., for a type of depression, is, or is selected for being, of Asian descent. In some embodiments, the human being that is treated with a combination of dextromethorphan and bupropion, e.g., for a type of depression, is, or is selected for being, of Japanese descent. In some embodiments, the human being that is treated with a combination of dextromethorphan and bupropion, e.g., for a type of depression, is, or is selected for being, of Korean descent. In some embodiments, the human being that is treated with a combination of dextromethorphan and bupropion, e.g., for a type of depression, is, or is selected for being, of Chinese descent. The assignment of an individual as having Asian, Chinese, Japanese, or Korean descent may be based upon self-reporting by the individual. In these Asian individuals, the combination of dextromethorphan and bupropion may be effective for treating depression where bupropion alone is not. This may be of particular importance because patients of Asian descent may suffer from more severe depression than those of other ethnic or cultural groups.

In some embodiments, the human being does not have, or is selected for not having, a depressive episode with psychotic or catatonic features.

In some embodiments, the human being does not have, or is selected for not having, a manic, hypomanic, or mixed episode, including bipolar disorder (Type 1 or Type 2) and substance-induced (e.g., antidepressant-induced) manic, or a hypomanic/mixed episode.

In some embodiments, the human being does not have, or is selected for not having schizophrenia, schizoaffective, or another psychotic disorder.

In some embodiments, the human being does not have, or is selected for not having, a panic disorder, with or without agoraphobia.

In some embodiments, the human being does not have, or is selected for not having obsessive-compulsive disorder.

In some embodiments, the human being does not have, or is selected for not having bulimia or anorexia nervosa.

In some embodiments, the human being does not have, or is selected for not having, a persistent neurocognitive disorder.

In some embodiments, the human being does not have, or is selected for not having, any anxiety disorder for the six months prior to treatment.

In some embodiments, the human being that is treated with a combination of dextromethorphan and bupropion, e.g., for a type of depression, has, or is selected for having, a diagnosis with major depressive disorder according to the Diagnostic and Statistical Manual of Mental Disorders, Fourth Edition, Text Revision (DSM-IV-TR), the Structured Clinical Interview for Diagnostic and Statistical Manual of Mental Disorders, Fifth Edition, Clinical Trials Version SCID-5-CT. In some embodiments, the human being currently meets the DSM-5 criteria for MDD without psychotic features, based on the SCID-5-CT In some embodiments, the human being that is treated with a combination of dextromethorphan and bupropion, e.g. for a type of depression, is suffering from, or is selected for suffering from, a major depressive episode that has lasted between about 8 weeks and about 24 months, about 1-6 months, about 6-12 months, about 1-2 years, at least about 1 week, at least about 2 weeks, at least about 3 weeks, at least about 4 weeks, at least about 6 weeks, at least about 2 months, at least about 3 months, at least about 4 months, at least about 6 months, at least about 9 months, at least about 1 year, at least about 18 months, at least about 2 years, about 1-12 weeks, about 3-6 months, about 6-9 months, about 9-12 months, about 12-18 months, about 18-24 months, about 2-4 years, about 4-6 years, about 6-10 years, about 10-20 years or longer.

In some embodiments, the human being that is treated with a combination of dextromethorphan and bupropion, e.g. for a type of depression, has, or is selected having, about 1-100, or more, lifetime depressive episodes, such as a major depressive episodes, including at least 1, at least about 2, at least about 3, at least about 4, at least about 5, at least about 10, at least about 15, at least about 20, at least about 30, at least about 40, at least about 50, at least about 60, at least about 70, at least about 80, at least about 90, at least about 100, about 1-5, about 5-10, about 10-20, about 20-30, about 30-40, about 40-50, about 50-60, about 60-70, about 70-80, about 80-90, about 90-100, or about 4-7 lifetime depressive episodes.

In some embodiments, the human being that is treated with a combination of dextromethorphan and bupropion, e.g., for a type of depression, has, or is selected for having, an inadequate response to one or more prior antidepressant therapies, e.g., 1, 2, 3, 4, 5 or more prior antidepressant therapies, including prior antidepressant therapies in the current depressive episode (e.g., the current major depressive episode).

In some embodiments, the human being that is treated with a combination of dextromethorphan and bupropion, e.g., for a type of depression, has had, or is selected for having had a background antidepressant therapy with, such as a selective serotonin reuptake inhibitor (SSRI), a serotonin norepinephrine reuptake inhibitor (SNRI), or bupropion, taken at an adequate dose for at least 8 weeks, and at a stable dose for at least 4 weeks prior to entering the double-blind treatment period. In some embodiments, the antidepressant therapy is continued in conjunction with treatment with the combination of bupropion and dextromethorphan.

In some embodiments, the human being that is treated with a combination of dextromethorphan and bupropion, e.g., for a type of depression, is, or is selected for being male. In some embodiments, the human being that is treated with a combination of dextromethorphan and bupropion, e.g., for a type of depression, is, or is selected for being female.

In some embodiments, the human being that is treated with a combination of dextromethorphan and bupropion, e.g. for a type of depression, has, or is selected for having, a body mass index of about 18-40 $kg/m^2$, about 18.5 $kg/m^2$, less than 18.5 $kg/m^2$, about 19 $kg/m^2$, about 19-24.9 $kg/m^2$, about 25 $kg/m^2$, about 25-29 $kg/m^2$, about 29 $kg/m^2$, more than 29 $kg/m^2$, about 18-22 $kg/m^2$, about 22-24 $kg/m^2$, about 24-26 $kg/m^2$, about 26-28 $kg/m^2$, about 28-30 $kg/m^2$, about 30-32 $kg/m^2$, about 32-34 $kg/m^2$, about 34-36 $kg/m^2$, about 36-38 $kg/m^2$, about 38-40 $kg/m^2$, about 18-26 $kg/m^2$, about 26-34 $kg/m^2$, or about 34-40 $kg/m^2$.

The MADRS is a clinician-rated scale. The MADRS is used to assess depressive symptomatology during the previous week. Subjects are rated on 10 items to assess feelings of guilt, sadness, lassitude, pessimism, inner tension, suicidality, reduced sleep or appetite, agitation, anxiety, weight loss, somatic symptoms, difficulty concentrating and lack of interest. Each item is scored on a 7-point scale. A score of 0 indicates the absence of symptoms, and a score of 6 indicates symptoms of maximum severity.

In some embodiments, the human being that is treated with a combination of dextromethorphan and bupropion, e.g. for a type of depression, has, or is selected for having, a MADRS score that is at least about 25, at least about 30, at least about 35, at least about 40, at least about 45, at least about 50, at least about 55, about 20-25, about 25-30, about 30-35, about 35-40, about 40-45, about 45-50, about 50-55, about 55-60, about 25-35, about 35-45, about 45-60, about 25-40, or about 40-60.

In some embodiments, treatment with the combination of dextromethorphan and bupropion results in the human being having a MADRS score that is reduced by at least about 10%, at least about 20%, at least about 30%, at least about 40%, at least about 50%, about 10-20%, about 20-30%, about 30-40%, about 40-50%, about 50-60%, about 60-80%, about 80-90%, or about 90-100% as compared to baseline or placebo. In some embodiments, the reduction is compared to baseline. In some embodiments, the reduction is compared to placebo.

In some embodiments, treatment with the combination of dextromethorphan and bupropion results in the human being having a MADRS score that is less than 34, about 20-34, about 7-19, about 0-6, about 30 or less, about 26 or less, about 25 or less, about 20 or less, about 17 or less, about 14 or less, about 12 or less, about 10 or less, about 8 or less, about 6 or less, about 5 or less, about 4 or less, about 3 or less, about 2 or less, about 1 or less, about 0, about 0.1-6, about 0.1-1, about 1-2, about 2-3, about 3-4, about 4-5, about 5-6, about 6-7, about 7-8, about 8-9, about 9-10, about 10-11, about 11-12, about 12-13, about 13-14, about 14-15, about 15-16, about 16-17, about 17-18, about 18-19, about 19-20, about 18-20, about 0.1-3, about 3-6, about 6-9, about 9-12, about 12-14, about 12-15, or about 15-20.

The subscale MADRS-6 is the sum of responses to six of the 10 MADRS items that are thought to represent the core symptoms of depression: reported sadness, apparent sadness, inner tension, lassitude, inability to feel, and pessimistic thoughts. MADRS items not included in the MADRS-6 score are reduced sleep, reduced appetite, concentration difficulties, and suicidal thoughts. Higher MADRS score indicates more severe depression, and each item yields a score of 0 to 6. The overall score ranges from 0 to 60. The questionnaire includes questions on the following symptoms 1. Apparent sadness 2. Reported sadness 3. Inner tension 4. Reduced sleep 5. Reduced appetite 6. Concentration difficulties 7. Lassitude 8. Inability to feel 9. Pessimistic thoughts 10. Suicidal thoughts. Usual cutoff points are: a) 0 to 6—normal/symptom absent; b) 7 to 19—mild depression; c) 20 to 34—moderate depression; and d)>34—severe depression.

In some embodiments, the human being that is treated with a combination of dextromethorphan and bupropion, e.g. for a type of depression, has, or is selected for having, a MADRS-6 score that is at least about 15, at least about 18, at least about 20, at least about 21, at least about 24, at least about 27, at least about 30, at least about 33, about 15-18, about 18-21, about 21-24, about 24-27, about 27-30, about 30-33, about 30-34, about 33-36, at least about 34, about 7-19, about 15-19, about 15-24, about 24-30, about 20-34, or about 30-36, prior to starting the treatment.

In some embodiments, treatment with the combination of dextromethorphan and bupropion results in the human being having a MADRS-6 score reduced by at least about 10%, at least about 20%, at least about 30%, at least about 40%, or at least about 50%, about 10-20%, about 20-30%, about 30-40%, about 40-50%, about 50-60%, about 60-80%, about 80-90%, or about 90-100% as compared to baseline or placebo. In some embodiments, the reduction is compared to baseline. In some embodiments, the reduction is compared to placebo.

In some embodiments, treatment with the combination of dextromethorphan and bupropion results in the human being having a MADRS-6 score that is about 17 or less, about 15 or less, about 10 or less, about 8 or less, about 6 or less, about 5 or less, about 4 or less, about 3 or less, about 2 or less, about 1 or less, about 0.1-6, about 0.1-1, about 1-2, about 2-3, about 3-4, about 4-5, about 5-6, about 6-7, about 7-8, about 8-9, about 9-12, about 12-15, about 0.1-3, about 3-6, about 6-8, about 6-9, or about 9-15.

In some embodiments, the human being that is treated with a combination of dextromethorphan and bupropion, e.g., for a type of depression, has, or is selected for having, a score for item 1 (Apparent sadness) on the MADRS that is 2, 4, or 6, prior to starting the treatment.

In some embodiments, treatment with the combination of dextromethorphan and bupropion results in the human being having a reduction of the score for item 1 on the MADRS that is at least about 10%, at least about 20%, at least about 30%, at least about 40%, or at least about 50% as compared to baseline or placebo. In some embodiments, the reduction is compared to baseline. In some embodiments, the reduction is compared to placebo.

In some embodiments, treatment with the combination of dextromethorphan and bupropion results in the human being having a score on item 1 of the MADRS that is about 2 or less.

Treatment effect may be assessed at any appropriate time, such as during weeks 1-2, weeks 1-3, weeks 1-4, weeks 1-6, weeks 4-6, weeks 6-8, weeks 8-12, weeks 12-16, at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time. In some embodiments, the treatment effect is assessed weekly using the MADRS.

The CGI-S scale is a clinician-rated scale used to rate the severity of the subject's current state of mental illness compared with a subject population with MDD. The subject is rated on a scale from 1 to 7, with 1 indicating a "normal state" and 7 indicating "among the most extremely ill subjects." The CGI-S may be administered by a person with extensive professional training and experience in assessing mental illness. Possible ratings are: 1) Normal, not at all ill; 2) Borderline mentally ill; 3) Mildly ill; 4) Moderately ill; 5) Markedly ill; 6) Severely ill; and 7) Among the most extremely ill patients.

In some embodiments, the human being that is treated with a combination of dextromethorphan and bupropion, e.g., for a type of depression, has, or is selected for having, a Clinical Global Impression-Severity (CGI-S) score that is at least about 3, at least about 4, at least about 5, at least about 6, about 7, about 3-7, about 4-7, about 3-4, about 4-5, about 5-6, or about 6-7.

In some embodiments, administering the combination of dextromethorphan and bupropion results in the human being having a reduction in the CGI-S score that is at least about 10%, at least about 20%, at least about 30%, at least about 40%, or at least about 50% as compared to baseline or placebo. In some embodiments, the reduction is compared to baseline. In some embodiments, the reduction is compared to placebo.

In some embodiments, administering the combination of dextromethorphan and bupropion results in the human being having a reduction in the CGI-S score that is at least about 1, at least about 2, at least about 3, at least about 4, at least about 5, about 0.1-6, about 0.1-1, about 1-2, about 2-3, about 3-4, about 4-5, about 5-6, about 0.1-3, or about 3-6. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-6, weeks 2-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The 16-item AIDS-SR-16, a patient-rated scale, is an abbreviated version of the 30-item Inventory of Depressive Symptomatology (IDS) and is designed to assess the severity of depressive symptoms. The AIDS-SR-16 assesses criterion symptom domains to diagnose a major depressive episode.

The QIDS-SR may be used to assess the subject's depressive symptomatology over the prior 7 days. Subjects report severity of symptoms on 10 items: sleep, feelings of sadness, appetite, weight change, concentration, self-regard, suicidality, general interest level, energy level, psychomotor retardation, and restlessness. Each item may be scored on a 4-point scale with a score of 0 reflecting no symptoms and a score of 3 reflecting symptoms of maximum severity.

Total QIDS scores range from 0 to 27, with scores of 5 or lower indicative of no depression, scores from 6 to 10 indicating mild depression, 11 to 15 indicating moderate depression, 16 to 20 reflecting severe depression, and total scores greater than 21 indicating very severe depression.

In some embodiments, the human being that is treated with a combination of dextromethorphan and bupropion, e.g., for a type of depression, has, or is selected for having, a QIDS-SR-16 score that is at least about 16, at least about 18, at least about 21, at least about 24, at least about 27, at least about 30, at least about 33, about 16-18, about 16-19, about 16-20, about 18-21, about 21-24, about 24-27, about 15-21, or about 21-27, prior to starting the treatment.

In some embodiments, administering the combination of dextromethorphan and bupropion results in the human being having a reduction in the QIDS-SR-16 score that is at least about 10%, at least about 20%, at least about 30%, at least about 40%, or at least about 50% as compared to baseline or placebo. In some embodiments, the reduction is compared to baseline. In some embodiments, the reduction is compared to placebo.

In some embodiments, treatment with the combination of dextromethorphan and bupropion results in the human being having a QIDS-SR-16 score that is about 6 or less, about 5 or less, about 4 or less, about 3 or less, about 2 or less, about 1 or less, about 0.1-6, about 0.1-5, about 0.1-1, about 1-2, about 2-3, about 3-4, about 4-5, about 5-6, about 0.1-3, or about 3-6. Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The CGI-I scale is a clinician-rated scale that is used to rate total improvement or worsening of mental illness regardless of whether the Investigator considers it to be a result of drug treatment or not. The subject is rated on a scale from 1 to 7, with 1 indicating that the subject is very much improved and 7 indicating that the subject is very much worse. The CGI-I may be administered by a person with extensive professional training and experience in assessing mental illness.

In some embodiments, treatment with the combination of dextromethorphan and bupropion results in the human being having a CGI-I score that is about 3 or less, about 2 or less, about 1, about 1-2, or about 2-3.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The VAMS is a patient-rated mood scale consisting of a 100-mm line with graphical, schematic, or pictorial representations of extremes of mood, e.g., happiness and sadness, at the two ends of the line, such as a sad face at one end and a happy face at the other end. Each end of the line may be further anchored by a word statement which describe the extremes of mood. Subjects are asked to rate their mood as a mark on the line. The distance on the line is measured and calculated as a numerical score from 0 to 100. Subjects may be asked to complete the VAMS daily.

In some embodiments, the human being that is treated with a combination of dextromethorphan and bupropion, e.g. for a type of depression, has, or is selected for having, a VAMS score that is at least about 40 mm, at least about 50 mm, at least about 60 mm, at least about 70 mm, at least about 80 mm, at least about 90 mm, about 40-50 mm, about 50-60 mm, about 60-70 mm, about 70-80 mm, about 80-90 mm, about 90-100 mm, about 40-60 mm, about 60-80 mm, or about 80-100 mm.

In some embodiments, administering the combination of dextromethorphan and bupropion results in the human being having a reduction in the VAMS score that is at least about 10%, at least about 20%, at least about 30%, at least about 40%, or at least about 50% as compared to baseline or placebo. In some embodiments, the reduction is compared to baseline. In some embodiments, the reduction is compared to placebo.

In some embodiments, treatment with the combination of dextromethorphan and bupropion results in the human being having a VAMS score that is less than about 50 mm, less than about 40 mm, less than about 30 mm, less than about 20 mm, less than about 10 mm, about 0-10 mm, about 10-20 mm, about 20-30 mm, about 30-40 mm, about 40-50 mm, about 0-25 mm, or about 25-50 mm.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The Columbia Suicide Severity Rating Scale (C-SSRS) is a clinician-rated instrument that reports the severity of both suicidal ideation and behavior. Suicidal ideation is classified on a 5-item scale: 1 (wish to be dead), 2 (nonspecific active suicidal thoughts), 3 (active suicidal ideation with any methods [not plan] without intent to act), 4 (active suicidal ideation with some intent to act, without specific plan), and 5 (active suicidal ideation with specific plan and intent). The C-SSRS also captures information about the intensity of ideation, specifically the frequency, duration, controllability, deterrents, and reasons for the most severe types of ideation. Suicidal behavior is classified on a 5-item scale: 0 (no suicidal behavior), 1 (preparatory acts or behavior), 2 (aborted attempt), 3 (interrupted attempt), and 4 (actual attempt). More than 1 classification can be selected provided they represent separate episodes. For actual attempts only, the actual or potential lethality is classified for the initial, most lethal, and most recent attempts.

The C-SSRS may be administered each time a person being treated sees a health professional. The C-SSRS may be completed for the subject's lifetime history of suicidal ideation and behavior, along with a recent recall period.

In some embodiments, administering the combination of dextromethorphan and bupropion results in the human being having a reduction in the Columbia-Suicide Severity Rating Scale (C-SSRS) score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The Sheehan Disability Scale (SDS) is a self-rated instrument used to measure the effect of the patient's symptoms on the following three items: work/school, social life, and family/home responsibilities. For each of the three items, scores range from 0 through 10. The number most representative of how much each area was disrupted by symptoms is marked along the line from 0 (not at all) to 10 (extremely). The three items or domains can be summarized to evaluate global functional impairment by adding the scores of each of the three items or domains, resulting in global SDS score ranges from 0 (unimpaired) to 30 (highly impaired).

In some embodiments, the human being that is treated with a combination of dextromethorphan and bupropion, e.g. for a type of depression, has, or is selected for having, a Sheehan Disability Scale (SDS) score that is: for each item SDS (0-10 scale) at least about 4, at least about 5, at least about 6, at least about 7, at least about 8, at least about 9; and for SDS total score at least about 5, at least 10, at least about 20, about 10-15, about 15-20, about 20-25, or about 25-30.

In some embodiments, administering the combination of dextromethorphan and bupropion results in the human being having a reduction in the SDS score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The Hamilton Rating Scale for Depression (HAM-D, HRSD, HDRS, or HAMD-17) is a clinician-rated, 17-item scale used to rate the subject's depressive state based on feelings of depression, guilt, suicidality, anxiety, agitation, level of insight, patterns of insomnia, loss of interest in work and other activities, weight loss, hypochondriasis, and degree of psychomotor retardation. It also can be used to identify genital, and somatic symptoms. Items are rated either on 0-2 scale or on 0-4 scale. A higher score is indicative of more severity. For example, HAM-D score level of depression of 10-13 is considered mild; 14-17 is considered mild to moderate; and >17 is considered moderate to severe.

In some embodiments, the human being that is treated with a combination of dextromethorphan and bupropion, e.g. for a type of depression, has, or is selected for having, a HAM-D score that is at least about 16, at least about 19, at least about 21, at least about 24, at least about 27, at least about 30, at least about 33, at least about 36, about 16-19, about 18-21, about 21-24, about 24-27, about 27-30, about 30-33, about 33-36, about 36-40, about 15-24, about 24-33, or about 33-40, or more than 40 prior to starting the treatment.

In some embodiments, administering the combination of dextromethorphan and bupropion results in the human being having a reduction in the HAM-D score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time. In some embodiments, the treatment effect is assessed weekly using the HAM-D.

Conversion from MADRS scores to HAM-D scores and vice versa may be accomplished using the table below.

| Total scores | | Change scores | | Percentage change scores | |
| --- | --- | --- | --- | --- | --- |
| MADRS | HAMD | MADRS | HAMD | MADRS | HAMD |
| | | | | −100 | −98 |
| | | | | −98 | −94 |
| | | | | −96 | −92 |
| 3 | 3 | −37 | −27 | −94 | −90 |
| 4 | 4 | −36 | −26 | −92 | −88 |
| 5 | 4 | −35 | −25 | −90 | −86 |
| 6 | 5 | −34 | −25 | −88 | −84 |
| 7 | 6 | −33 | −24 | −86 | −83 |
| 8 | 7 | −32 | −23 | −84 | −81 |
| 9 | 7 | −31 | −23 | −82 | −80 |
| 10 | 8 | −30 | −22 | −80 | −79 |
| 11 | 9 | −29 | −22 | −78 | −77 |
| 12 | 9 | −28 | −21 | −76 | −75 |
| 13 | 10 | −27 | −20 | −74 | −74 |
| 14 | 11 | −26 | −20 | −72 | −73 |
| 15 | 12 | −25 | −19 | −70 | −72 |
| 16 | 12 | −24 | −18 | −68 | −70 |
| 17 | 13 | −23 | −18 | −66 | −67 |
| 18 | 14 | −22 | −17 | −64 | −65 |
| 19 | 15 | −21 | −16 | −62 | −62 |
| 20 | 16 | −20 | −16 | −60 | −61 |
| 21 | 16 | −19 | −15 | −58 | −59 |
| 22 | 17 | −18 | −14 | −56 | −57 |
| 23 | 18 | −17 | −14 | −54 | −56 |
| 24 | 19 | −16 | −13 | −52 | −54 |
| 25 | 19 | −15 | −12 | −50 | −52 |
| 26 | 20 | −14 | −12 | −48 | −50 |
| 27 | 21 | −13 | −11 | −46 | −48 |
| 28 | 22 | −12 | −10 | −44 | −47 |
| 29 | 23 | −11 | −9 | −42 | −45 |
| 30 | 23 | −10 | −9 | −40 | −43 |
| 31 | 24 | −9 | −8 | −38 | −41 |
| 32 | 25 | −8 | −7 | −36 | −39 |
| 33 | 25 | −7 | −6 | −34 | −37 |
| 34 | 26 | −6 | −6 | −32 | −35 |
| 35 | 27 | −5 | −5 | −30 | −33 |
| 36 | 28 | −4 | −4 | −28 | −31 |
| 37 | 29 | −3 | −3 | −26 | −29 |
| 38 | 29 | −2 | −2 | −24 | −27 |

-continued

| Total scores | | Change scores | | Percentage change scores | |
|---|---|---|---|---|---|
| MADRS | HAMD | MADRS | HAMD | MADRS | HAMD |
| 39 | 30 | −1 | −1 | −22 | −25 |
| 40 | 31 | 0 | −1 | −20 | −23 |
| 41 | 32 | 1 | 0 | −18 | −21 |
| 42 | 33 | 2 | 1 | −16 | −19 |
| 43 | 34 | 3 | 2 | −14 | −17 |
| 44 | 35 | 4 | 2 | −12 | −15 |
| 45 | 35 | 5 | 3 | −10 | −13 |
| 46 | 36 | 6 | 4 | −8 | −11 |
| 47 | 37 | 7 | 4 | −6 | −9 |
| 48 | 37 | 8 | 5 | −4 | −7 |
| 49 | 38 | | | −2 | −5 |
| 50 | 38 | | | 0 | −3 |
| 51 | 39 | | | 2 | 0 |
| 52 | 40 | | | 4 | 1 |
| 53 | 40 | | | 6 | 2 |
| | | | | 8 | 4 |
| | | | | 10 | 5 |
| | | | | 12 | 7 |
| | | | | 14 | 9 |
| | | | | 16 | 10 |
| | | | | 18 | 11 |
| | | | | 20 | 13 |
| | | | | 22 | 15 |
| | | | | 24 | 17 |
| | | | | 26 | 18 |
| | | | | 28 | 19 |
| | | | | 30 | 20 |
| | | | | 32 | 21 |
| | | | | 34 | 22 |
| | | | | 36 | 24 |
| | | | | 38 | 26 |
| | | | | 40 | 28 |

Negative values mean improvement.

The Hamilton Anxiety Scale (HAM-A) is a clinician-administered scale which consists of 14 items, each rated on a five point scale ranging from 0 (not present) to 4 (very severe). The highest possible total score is 56, which represents the most severe form of anxiety; the lowest possible score is 0, which represents an absence of anxiety.

In some embodiments, the human being that is treated with a combination of dextromethorphan and bupropion, e.g. for a type of depression, has, or is selected for having, a Hamilton Anxiety Scale (HAM-A) score that is at least about 20, at least about 25, at least about 30, at least about 35, at least about 40, at least about 45, at least about 50, at least about 55, about 20-25, about 25-30, about 30-35, about 35-40, about 40-45, about 45-50, about 50-56, about 25-35, about 35-45, about 45-56, about 25-40, or about 40-56.

In some embodiments, administering the combination of dextromethorphan and bupropion results in the human being having a reduction in the HAM-A score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The Massachusetts General Hospital Cognitive and Physical Functioning Questionnaire (CPFQ) is a 7-item patient-rated scale used to measure cognitive and executive dysfunction in mood and anxiety disorders and was developed to assess clinically relevant cognitive and physical symptoms that could emerge or persist during long-term treatment for depression. Subjects grade the perceived quality of their physical and cognitive functioning. It is scored from 1-6 with increasing severity that individually evaluates 7 distinct items: motivation/enthusiasm, wakefulness/alertness, energy, focus/attention, recall, ability to find words, and sharpness/mental acuity. The physical dimension of the CPFQ assesses sleepiness and fatigue, and the cognitive dimension assesses apathy, inattention, forgetfulness, word-finding difficulties, and mental slowness. A higher score is indicative of more impairment.

In some embodiments, administering the combination of dextromethorphan and bupropion results in the human being having a reduction in the CPFQ score that is at least about 10%, at least about 20%, at least about 30%, at least about 40%, or at least about 50% as compared to baseline or placebo. In some embodiments, the reduction is compared to baseline. In some embodiments, the reduction is compared to placebo.

In some embodiments, administering the combination of dextromethorphan and bupropion results in the human being having a reduction in the CPFQ-Cognitive subscales (items 4-7) score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

The Brief Psychiatric Rating Scale (BPRS) is a clinician-administered scale developed to measure psychiatric symptoms such as depression, anxiety, hallucinations, and unusual behavior. Each symptom is rated from 1 (not present) to 7 (extremely severe). Zero is entered if the item is not assessed and will be excluded from the analysis. The scale should be administered by a clinician who is knowledgeable concerning psychotic disorders and able to interpret the constructs used in the assessment. Factor 1 (Reality Distortion) items are Suspiciousness, Hallucinatory Behavior and Unusual Thought Content.

In some embodiments, the human being that is treated with a combination of dextromethorphan and bupropion, e.g., for a type of depression, has, or is selected for having, a Brief Psychiatric Rating Scale (BPRS)-Factor 1 score that is starting score: at least about 3, at least about 4, at least about 5, at least about 6, about 7, about 3-7, about 4-7, about 4-5, about 5-6, or about 6-7.

In some embodiments, administering the combination of dextromethorphan and bupropion results in the human being having a reduction in the BPRS-Factor 1 score that is at least about 1, at least about 2, at least about 3, at least about 4, at least about 5, about 0.1-6, about 0.1-1, about 1-2, about 2-3, about 3-4, about 4-5, about 5-6, about 0.1-3, or about 3-6 as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

In some embodiments, the human being that is treated with a combination of dextromethorphan and bupropion, e.g. for a type of depression, has, or is selected for having, a Beck Depression Inventory (BDI) score that is at least about 20, at least about 25, at least about 30, at least about 35, at least about 40, at least about 45, at least about 50, at least about 55, at least about 60, about 20-25, about 25-30, about 30-35, about 35-40, about 40-45, about 45-50, about 50-55, about 55-60, about 60-63, about 25-35, about 35-45, about 45-55, about 55-63, about 25-40, or about 40-63.

The Beck Depression Inventory (BDI, BDI-1A, BDI-II) is a 21-question multiple-choice self-report inventory about how the subject has been feeling in the last week. Each question had a set of four possible responses, ranging in intensity. When the test is scored, a value of 0 to 3 is assigned for each answer and then the total score is compared to a key to determine the depression's severity. Higher total scores indicate more severe depressive symptoms. The standard cut-off scores were as follows: 0-9: indicates minimal depression; 10-18: indicates mild depression; 19-29: indicates moderate depression; and 30-63: indicates severe depression.

In some embodiments, administering the combination of dextromethorphan and bupropion results in the human being having a reduction in the BDI score that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

In some embodiments, the human being that is treated with a combination of dextromethorphan and bupropion, e.g., for a type of depression, has, or is selected for having, C Reactive Protein (CRP) levels that are at least 0.5 mg/L, at least 1 mg/L, at least 2 mg/L, or higher.

In some embodiments, administering the combination of dextromethorphan and bupropion results in the human being having an improvement in CRP level that is at least about 10%, at least about 20%, at least about 30%, at least about 40%, or at least about 50% as compared to baseline or placebo. In some embodiments, the reduction is compared to baseline. In some embodiments, the reduction is compared to placebo.

Treatment effect may be assessed at any appropriate time, such as during weeks 1-2, weeks 1-3, weeks 1-4, weeks 1-5, weeks 1-6, weeks 4-6, weeks 6-8, weeks 8-12, weeks 12-16, at the beginning or at the end of week 1, at the beginning or at the end of week 2, at the beginning or at the end of week 3, at the beginning or at the end of week 4, at the beginning or at the end of week 5, at the beginning or at the end of week 6, at the beginning or at the end of week 7, at the beginning or at the end of week 8, at the beginning or at the end of week 9, at the beginning or at the end of week 10, at the beginning or at the end of week 11, at the beginning or at the end of week 12, at the beginning or at the end of week 13, at the beginning or at the end of week 14, at the beginning or at the end of week 15, at the beginning or at the end of week 16, or at any other time.

Conversion between some of the scores in some of the assessments above may be done according to the tables below.

| Severity | IDS-C | IDS-SR | QIDS-C | QIDS-SR | HRSD 17 | HRSD21 | HRSD24 | MADRS | BDI |
|---|---|---|---|---|---|---|---|---|---|
| 0 | 0-3 | 0-3 | 0 | 0 | 0 | 0-1 | 0-1 | 0 | 0 |
| 0 | 4-5 | 4-5 | 1 | 1 | 1-2 | 2 | 2 | | |
| 0 | 6 | 6 | 2 | 2 | 3 | 3 | 3-4 | | |
| 0 | 7-8 | 7-8 | 3 | 3 | 4 | 4 | 5 | | |
| 0 | 9-10 | 9-11 | 4 | 4 | 5-6 | 5-6 | 6-7 | | |
| 0 | 11 | 12-13 | 5 | 5 | 7 | 7-8 | 8-9 | 6 | 9 |
| 1 | 12-15 | 14-16 | 6 | 6 | 8 | 9 | 10-11 | 7 | 10 |
| 1 | 16-17 | 17-18 | 7 | 7 | 9-10 | 10 | 12 | | |
| 1 | 18-20 | 19-21 | 8 | 8 | 11 | 11-12 | 13-14 | | |
| 1 | 21-22 | 22-23 | 9 | 9 | 12 | 13 | 15-16 | | |
| 1 | 23 | 24-25 | 10 | 10 | 13 | 14-15 | 17-18 | 19 | 18 |
| 2 | 24-27 | 26-28 | 11 | 11 | 14-15 | 16 | 19 | 20 | 19 |
| 2 | 28-29 | 29-30 | 12 | 12 | 16 | 17 | 20-21 | | |

-continued

| Severity | IDS-C | IDS-SR | QIDS-C | QIDS-SR | HRSD 17 | HRSD21 | HRSD24 | MADRS | BDI |
|---|---|---|---|---|---|---|---|---|---|
| 2 | 30-32 | 31-33 | 13 | 13 | 17 | 18-19 | 22-23 | | |
| 2 | 33-35 | 34-36 | 14 | 14 | 18-19 | 20-21 | 24-25 | | |
| 2 | 36 | 37-38 | 15 | 15 | 18-19 | 22 | 26 | 34 | 29 |
| 3 | 37-39 | 39-40 | 16 | 16 | 20 | 23 | 27-28 | 35 | 30 |
| 3 | 40-41 | 41-43 | 17 | 17 | 21-22 | 24-25 | 29-30 | | |
| 3 | 42-43 | 44-45 | 18 | 18 | 23 | 26 | 31-32 | | |
| 3 | 44-45 | 46-47 | 19 | 19 | 24 | 27 | 33 | | |
| 3 | 46 | 48 | 20 | 20 | 25 | 28 | 34 | | |
| 4 | 47-51 | 49-53 | 21 | 21 | 26-27 | 29-31 | 35-38 | | |
| 4 | 52-53 | 54-55 | 22 | 22 | 28 | 32 | 39 | | |
| 4 | 54-56 | 56-58 | 23 | 23 | 29 | 33-34 | 40-41 | | |
| 4 | 57-59 | 59-61 | 24 | 24 | 30-31 | 35-36 | 42-44 | | |
| 4 | 60-62 | 62-24 | 25 | 25 | 32 | 37-38 | 45-46 | | |
| 4 | 63-65 | 65-67 | 26 | 26 | 33-35 | 39-41 | 47-49 | | |
| 4 | 66-84 | 68-84 | 27 | 27 | 36-52 | 42-64 | 50-75 | 60 | 63 |

[1] Severity of Depression. 0 = None, 1 = Mild, 2 = Moderate, 3 = Severe, 4 = Very Severe.

| Severity | IDS-SR | QIDS-SR | HRSD 17 | HRSD21 | HRSD24 |
|---|---|---|---|---|---|
| 0 | 0-3 | 0 | 0 | 0-1 | 0-1 |
| 0 | 4-5 | 1 | 1-2 | 2 | 2 |
| 0 | 6 | 2 | 3 | 3 | 3-4 |
| 0 | 7-8 | 3 | 4 | 4 | 5 |
| 0 | 9-11 | 4 | 5-6 | 5-6 | 6-7 |
| 0 | 12-13 | 5 | 7 | 7-8 | 8-9 |
| 1 | 14-16 | 6 | 8 | 9 | 10-11 |
| 1 | 17-18 | 7 | 9-10 | 10 | 12 |
| 1 | 19-21 | 8 | 11 | 11-12 | 13-14 |
| 1 | 22-23 | 9 | 12 | 13 | 15-16 |
| 1 | 24-25 | 10 | 13 | 14-15 | 17-18 |
| 2 | 26-28 | 11 | 14-15 | 16 | 19 |
| 2 | 29-30 | 12 | 16 | 17 | 20-21 |
| 2 | 31-33 | 13 | 17 | 18-19 | 22-23 |
| 2 | 34-36 | 14 | 18-19 | 20-21 | 24-25 |
| 2 | 37-38 | 15 | 18-19 | 22 | 26 |
| 3 | 39-40 | 16 | 20 | 23 | 27-28 |
| 3 | 41-43 | 17 | 21-22 | 24-25 | 29-30 |
| 3 | 44-45 | 18 | 23 | 26 | 31-32 |
| 3 | 46-47 | 19 | 24 | 27 | 33 |
| 3 | 48 | 20 | 25 | 28 | 34 |
| 4 | 49-53 | 21 | 26-27 | 29-31 | 35-38 |
| 4 | 54-55 | 22 | 28 | 32 | 39 |
| 4 | 56-58 | 23 | 29 | 33-34 | 40-41 |
| 4 | 59-61 | 24 | 30-31 | 35-36 | 42-44 |
| 4 | 62-24 | 25 | 32 | 37-38 | 45-46 |
| 4 | 65-67 | 26 | 33-35 | 39-41 | 47-49 |
| 4 | 68-84 | 27 | 36-52 | 42-64 | 50-75 |

Severity of Depression. 0 = None, 1 = Mild, 2 = Moderate, 3 = Severe, 4 = Very Severe.

| QIDS-SR16 | IDS-SR30 | HAM-D24 | HAM-D21 | HAM-D17 |
|---|---|---|---|---|
| 0 | 0-3 | 0-1 | 0-1 | 0 |
| 1 | 4-5 | 2 | 2 | 1-2 |
| 2 | 6 | 3-4 | 3 | 3 |
| 3 | 7-8 | 5 | 4 | 4 |
| 4 | 9-11 | 6-7 | 5-6 | 5-6 |
| 5 | 12-13 | 8-9 | 7-8 | 7 |
| 6 | 14-16 | 10-11 | 9 | 8 |
| 7 | 17-18 | 12 | 10 | 9-10 |
| 8 | 19-21 | 13-14 | 11-12 | 11 |
| 9 | 22-23 | 15-16 | 13 | 12 |
| 10 | 24-25 | 17-18 | 14-15 | 13 |
| 11 | 26-28 | 19 | 16 | 14-15 |
| 12 | 29-30 | 20-21 | 17 | 16 |
| 13 | 31-33 | 22-23 | 18-19 | 17 |
| 14 | 34-36 | 24-25 | 20-21 | 18-19 |
| 15 | 37-38 | 26 | 22 | 18-19 |
| 16 | 39-40 | 27-28 | 23 | 20 |
| 17 | 41-43 | 29-30 | 24-25 | 21-22 |
| 18 | 44-45 | 31-32 | 26 | 23 |
| 19 | 46-47 | 33 | 27 | 24 |
| 20 | 48 | 34 | 28 | 25 |
| 21 | 49-53 | 35-38 | 29-31 | 26-27 |
| 22 | 54-55 | 39 | 32 | 28 |
| 23 | 56-58 | 40-41 | 33-34 | 29 |
| 24 | 59-61 | 42-44 | 35-36 | 30-31 |
| 25 | 62-24 | 45-46 | 37-38 | 32 |
| 26 | 65-67 | 47-49 | 39-41 | 33-35 |
| 27 | 68-84 | 50-75 | 42-64 | 36-52 |

| IDS-SR30 | QIDS-SR16 | HAM-D24 | HAM-D21 | HAM-D17 |
|---|---|---|---|---|
| 0-2 | 0 | 0 | 0 | 0 |
| 3 | 0 | 1 | 1 | 1 |
| 4-5 | 1 | 2-3 | 2 | 2 |
| 6 | 2 | 4 | 3 | 3 |
| 7 | 3 | 5 | 4 | 3 |
| 8 | 3 | 5 | 4 | 4 |
| 9 | 4 | 6 | 5 | 5 |
| 10 | 4 | 7 | 6 | 5 |
| 11 | 4 | 7 | 6 | 6 |
| 12 | 5 | 8 | 7 | 6 |
| 13 | 5 | 9 | 7 | 7 |
| 14 | 6 | 9 | 8 | 7 |
| 15 | 6 | 10 | 9 | 8 |
| 16 | 6 | 11 | 9 | 9 |
| 17 | 7 | 12 | 10 | 9 |
| 18 | 7 | 12 | 10 | 10 |
| 19 | 8 | 13 | 11 | 10 |
| 20 | 8 | 14 | 12 | 11 |
| 21 | 8 | 15 | 12 | 11 |
| 22 | 9 | 15 | 13 | 12 |
| 23 | 9 | 16 | 13 | 12 |
| 24 | 10 | 17 | 14 | 13 |
| 25 | 10 | 17 | 15 | 13 |
| 26 | 11 | 18 | 15 | 14 |
| 27 | 11 | 19 | 16 | 14 |
| 28 | 11 | 20 | 16 | 15 |
| 29 | 12 | 20 | 17 | 15 |
| 30 | 12 | 21 | 17 | 16 |
| 31 | 13 | 22 | 18 | 16 |
| 32 | 13 | 22 | 19 | 17 |
| 33 | 13 | 23 | 19 | 17 |
| 34 | 14 | 24 | 20 | 18 |
| 35 | 14 | 25 | 20 | 19 |
| 36 | 14 | 25 | 21 | 19 |
| 37-38 | 15 | 26 | 22 | 20 |
| 39-40 | 16 | 27-28 | 23 | 20 |
| 41 | 17 | 29 | 24 | 21 |

-continued

| IDS-SR30 | QIDS-SR16 | HAM-D24 | HAM-D21 | HAM-D17 |
|---|---|---|---|---|
| 42-43 | 17 | 30 | 25 | 22 |
| 44-45 | 18 | 31-32 | 26 | 23 |
| 46-47 | 19 | 33 | 27 | 24 |
| 48 | 20 | 34 | 28 | 25 |
| 49-50 | 21 | 35 | 29 | 26 |
| 51-52 | 21 | 36-37 | 30 | 26 |
| 53 | 21 | 38 | 31 | 27 |
| 54-55 | 22 | 39 | 32 | 28 |
| 56-57 | 23 | 40 | 33 | 29 |
| 58 | 23 | 41 | 34 | 29 |
| 59 | 24 | 42-43 | 35 | 30 |
| 60-61 | 24 | 44 | 36 | 31 |
| 62 | 25 | 45 | 37 | 32 |
| 63-64 | 25 | 46 | 38 | 33 |
| 65 | 26 | 47 | 39 | 33 |
| 66 | 26 | 48 | 40 | 34 |
| 67 | 26 | 49 | 41 | 35 |
| 68 | 27 | 50 | 42 | 35 |
| 69-70 | 27 | 51 | 43 | 36 |
| 71 | 27 | 52 | 44 | 37 |
| 72 | 27 | 53-54 | 45 | 38 |
| 73-74 | 27 | 55 | 46 | 39 |
| 75-76 | 27 | 56 | 47-48 | 40 |
| 77-78 | 27 | 57-58 | 49-50 | 42-43 |
| 79-82 | 27 | 59-62 | 51-54 | 44-48 |
| 83-84 | 27 | 63-75 | 55-64 | 49-52 |

In some embodiments, the combination of dextromethorphan and bupropion is a novel and oral NMDA receptor antagonist with multimodal activity for the treatment of central nervous system (CNS) disorders. The dextromethorphan is a non-competitive N-methyl-D-aspartate (NMDA) receptor antagonist, also known as a glutamate receptor modulator, which is a novel mechanism of action that works differently than currently available therapies for depression.

The dextromethorphan is also a sigma-1 receptor agonist, nicotinic acetylcholine receptor antagonist, and inhibitor of the serotonin and norepinephrine transporters. The bupropion can increase the bioavailability of dextromethorphan, and is a norepinephrine and dopamine reuptake inhibitor, and a nicotinic acetylcholine receptor antagonist. Both dextromethorphan and bupropion are nicotinic acetylcholine receptor antagonists, a mechanism that is relevant to nicotine dependence. Thus, the combination of dextromethorphan and bupropion provides a potentially new mechanism of action for smoking cessation treatment.

In some embodiments, the combination of dextromethorphan and bupropion may be used to treat nicotine addiction. In some embodiments, the combination of dextromethorphan and bupropion may be administered once daily or twice daily to a human being. In some embodiments, the combination of dextromethorphan and bupropion may be administered twice daily to a human being. In some embodiments, the combination of dextromethorphan and bupropion may be administered once daily or twice daily to a human being for at least 1 week, at least 2 weeks, at least 3 weeks, at least 4 weeks, at least 5 weeks, at least 6 weeks, at least 1 month, at least 2 months, at least 3 months, at least 4 months, at least 5 months, at least 6-months, about 6-12 months, about 1 year, about 2 years or longer. In some embodiments, the combination of dextromethorphan and bupropion may be administered twice daily to a human being for at least 1 week, at least 2 weeks, at least 3 weeks, or longer.

In some embodiments, the smoker may be, or may be selected for being, an ad-lib smoker. In some embodiments, the smoker may, or may be selected for, smoking 10 or more cigarettes daily on average, such as about 10, about 10-15, about 10-17, about 10-20, about 11, about 12, about 13, about 14, about 15, about 16, about 17, about 18, about 19, about 20, about 20-25, about 25-30, about 30-40, about 40-50 cigarettes, or more, before administration of the combination of dextromethorphan and bupropion.

In some embodiments, the combination of dextromethorphan and bupropion may be used to treat nicotine addiction, and the combination contains about 30-100 mg, about 30-40 mg, about 40-50 mg, about 50-60 mg, about 60-70 mg, about 70-80 mg, about 80-90 mg, about 90-100 mg, about 35 mg, about 35 mg, about 55 mg, about 65 mg, about 75 mg, about 85 mg, or about 95 mg of dextromethorphan in a free base form or a salt form. In some embodiments, the dextromethorphan is in an HBr salt form.

In some embodiments, the combination of dextromethorphan and bupropion may be used to treat nicotine addiction, wherein the combination contains about 100-200 mg, about 100-150 mg, about 150-200 mg, about 100-110 mg, about 110-120 mg, about 120-130 mg, about 130-140 mg, about 140-150 mg, about 150-160 mg, about 160-170 mg, about 170-180 mg, about 180-190 mg, about 190-200 mg, about 105 mg, about 115 mg, about 125 mg, about 135 mg, about 145 mg, about 150 mg, about 155-165 mg, about 165-175 mg, about 175-185 mg, or about 185-195 mg of bupropion in a free base form or a salt form. In some embodiments, the bupropion is in an HCl salt form.

In some embodiments, administration of the combination of dextromethorphan and bupropion to human beings results in the reduction of smoking intensity as measured using the number of cigarettes smoked per day, assessed via daily smoking diaries.

The treatment with the combination of dextromethorphan and bupropion to human beings results in at least 5%, at least 10%, at least 15%, at least 20%, at least 25%, about 5-10%, about 10-15%, about 15-20%, about 20-25%, about 25-30%, 10-20%, about 20-30%, about 30-40%, about 40-50%, about 50-60%, about 60-80%, about 80-100%, about 20%, about 25% greater, about 30%, or about 50% reduction in the average number of cigarettes smoked per day as compared to bupropion alone over a period of time, such as 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 6 months, or longer.

The treatment with the combination of dextromethorphan and bupropion to human beings results in average reduction of at least 1, at least 2, at least 3, at least 4, at least 5, at least 6, at least 7, at least 8, at least 9, at least 10, at least 15, at least 20, about 8-9, about 8-10, about 10-15, about 15-20, about 25, or more cigarettes per day.

The treatment with the combination of dextromethorphan and bupropion to human beings results in a greater proportion of smokers, such as at least 30%, at least 35%, at least 40%, at least 45%, at least 50%, at least 55%, at least 60%, at least 65%, at least 70%, about 35%, about 50%, about 60%, about 60-80%, about 80-90%, about 90-100%, who experience a more than 50% reduction in expired carbon monoxide levels, a biochemical marker of smoking intensity, as compared to those treated with bupropion alone.

The treatment with the combination of dextromethorphan and bupropion to human beings results in at least 1, or about 1-2 cigarettes fewer on the day of administration and at least 1, at least 2, about 1-2, or about 2-3 cigarettes fewer on the following day as compared to those who missed one or both doses of the combination of dextromethorphan and bupropion.

The treatment of smoking cessation with the combination of dextromethorphan and bupropion to human beings results in the magnitude of improvement over bupropion alone that is similar to the improvement over placebo reported for the approved smoking cessation treatment varenicline in studies with a similar design.

In some embodiments, an enhanced bioavailability of dextromethorphan, or a combination of dextromethorphan and an antidepressant such as bupropion, hydroxybupropion, erythrohydroxybupropion, threohydroxybupropion, or a metabolite or prodrug of any of these compounds, may be used as an adjunctive therapy for treatment of any condition recited herein, including TRD. For example, the adjunctive therapy could be used in combination with another antidepressant, such as bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, ketamine, etc., or a metabolite or prodrug of any of these compounds, or a pharmaceutically acceptable salt of any of these compounds.

In some embodiments, TRD may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds and may result in a reduction of depressive symptoms of at least about 5%, at least about 10%, at least about 20%, at least about 30%, at least about 40%, at least about 50%, at least about 60%, at least about 70%, at least about 80%, at least about 90%, up to about 100%, or any other reduction in a range bounded by any of these values.

Psychiatric disorders that may be treated by enhanced plasma levels of dextromethorphan such as those achieved by a combination of dextromethorphan and an antidepressant such as bupropion, hydroxybupropion, erythrohydroxybupropion, threohydroxybupropion, or a metabolite or prodrug of any of these compounds, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

In some embodiments, agitation in Alzheimer's disease may be treated by enhanced plasma levels of dextromethorphan or by a combination of dextromethorphan and an antidepressant such as bupropion, hydroxybupropion, erythrohydroxybupropion, threohydroxybupropion, or a metabolite or prodrug of any of these compounds and may result in a reduction of agitation-related symptoms of at least about 5%, at least about 10%, at least about 20%, at least about 30%, at least about 40%, at least about 50%, at least about 60%, at least about 70%, at least about 80%, at least about 90%, up to about 100%, or any other reduction in a range bounded by any of these values.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Measures of treatment effect that may be improved by treatment with enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, Neuropsychiatric Inventory-Clinician (NPI-C) rating scale, overall and all domains; Neuropsychiatric Inventory-Clinician (NPI-C) rating scale Agitation domain; Cohen-Mansfield Agitation Inventory (CMAI); Cornell Scale for Depression in Dementia (CSDD); Neuropsychiatric Inventory (NPI Agitation/Aggression Domain); Cocomitant Medications (Frequency of using concomitant medications); Alzheimer's Disease Cooperative Study-Activities of Daily Living Inventory (ADCS-ADL); Neuropsychiatric Inventory (NPI) Individual Domains and NPI Total Scores (range 0-144), including NPI-C Apathy domain, NPI Agitation/Aggression Caregiver Distress, Modified Alzheimer's Disease Cooperative Study-Clinical Global Impression of Change Agitation (mADCS-CGIC Agitation), Patient Global Impression of Change (PGIC) (rated by caregiver), Dementia Quality of Life (DEMQOL), Quality of Life-Alzheimer's disease measure (QoL-AD), Zarit Burden Scale, Resource Utilization in Dementia (RUD), Alzheimer's Disease Assessment Scale-Cognitive Subscale (ADAS-Cog), Mini-mental State Examination (MMSE), Caregiver Strain Index (CSI), Individual Domain of the Neuropsychiatric Inventory (NPI), Total Neuropsychiatric Inventory (NPI) Score, Neuropsychiatric Inventory (Agitation/Aggression Domain of NPI), Neuropsychiatric Inventory (Caregiver Distress for NPI Domains), etc.

Substance addiction abuse that may be treated by enhanced bioavailability or plasma levels of dextromethorphan or by a combination of dextromethorphan and an antidepressant such as bupropion, hydroxybupropion, erythrohydroxybupropion, threohydroxybupropion, or a metabolite or prodrug of any of these compounds, includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supra nuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, migraine, tension, and cluster headaches.

Other neurological disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, a combination of dextromethorphan and an antidepressant such as bupropion, hydroxybupropion, erythrohydroxybupropion, threohydroxybupropion, or a metabolite or prodrug of any of these compounds, may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, a combination of dextromethorphan and an antidepressant such as bupropion, hydroxybupropion, erythrohydroxybupropion, threohydroxybupropion, or a metabolite or prodrug of any of these compounds may be used to treat treatment refractory depression.

In some embodiments, a combination of dextromethorphan and an antidepressant such as bupropion, hydroxybupropion, erythrohydroxybupropion, threohydroxybupropion, or a metabolite or prodrug of any of these compounds may be used to treat allodynia.

In some embodiments, a combination of dextromethorphan and an antidepressant such as bupropion, hydroxybupropion, erythrohydroxybupropion, threohydroxybupropion, or a metabolite or prodrug of any of these compounds may be used to treat treatment refractory hyperalgesia.

In some embodiments, a combination of dextromethorphan and an antidepressant such as bupropion, hydroxybupropion, erythrohydroxybupropion, threohydroxybupropion, or a metabolite or prodrug of any of these compounds may be used to treat dermatitis.

Pain relieving properties of dextromethorphan may be enhanced by a method comprising co-administering dextromethorphan and an antidepressant, such as bupropion, hydroxybupropion, erythrohydroxybupropion, threohydroxybupropion, or a metabolite or prodrug of any of these compounds, with dextromethorphan.

Pain relieving properties of bupropion may be enhanced by a method comprising co-administering dextromethorphan with bupropion, hydroxybupropion, erythrohydroxybupropion, threohydroxybupropion, or a metabolite or prodrug of any of these compounds.

In some embodiments, ketamine or another NMDA receptor antagonist may be administered with an antidepressant, such as bupropion, hydroxybupropion, erythrohydroxybupropion, threohydroxybupropion, or a metabolite or prodrug of any of these compounds.

In some embodiments, dextromethorphan and quinidine may be co-administered with an antidepressant, such as bupropion, hydroxybupropion, erythrohydroxybupropion, threohydroxybupropion, or a metabolite or prodrug of any of these compounds.

These methods may be used to treat, or provide relief to, any type of pain including, but not limited to, musculoskeletal pain, neuropathic pain, cancer-related pain, acute pain, nociceptive pain, inflammatory pain, arthritis pain, complex regional pain syndrome, etc.

In some embodiments, co-administering dextromethorphan with bupropion, hydroxybupropion, erythrohydroxybupropion, threohydroxybupropion, or a metabolite or prodrug of any of these compounds may be used to treat or reduce inflammation or inflammatory conditions, such as Crohn's disease, including pain associated with inflammation.

In some embodiments, co-administering dextromethorphan with bupropion, hydroxybupropion, erythrohydroxybupropion, threohydroxybupropion, or a metabolite or prodrug of any of these compounds may be used to treat psoriasis, cancer, viral infection, or as an adjuvant treatment for multiple myeloma.

Examples of musculoskeletal pain include low back pain (i.e., lumbosacral pain), primary dysmenorrhea, and arthritic pain, such as pain associated with rheumatoid arthritis, juvenile rheumatoid arthritis, osteoarthritis, axial spondyloarthritis including ankylosing spondylitis, pain associated with vertebral crush fractures, fibrous dysplasia, osteogenesis imperfecta, Paget's disease of bone, transient osteoporosis, and transient osteoporosis of the hip, etc.

In some embodiments, a combination of dextromethorphan and an antidepressant, such as bupropion, may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, a combination of dextromethorphan and an antidepressant, such as bupropion, may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, a combination of dextromethorphan and an antidepressant, such as bupropion, is used to treat chronic musculoskeletal pain.

In some embodiments, a combination of dextromethorphan and an antidepressant, such as bupropion, may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, a combination of dextromethorphan and an antidepressant, such as bupropion, may be administered orally to relieve neuropathic pain.

Examples of neuropathic pain include diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemo-therapy associated neuropathy, etc.

In some embodiments, a combination of dextromethorphan and an antidepressant, such as bupropion, may be administered to relieve fibromyalgia.

The term "treating", or "treatment" includes the diagnosis, cure, mitigation, treatment, or prevention of disease in man or other animals, or any activity that otherwise affects the structure or any function of the body of man or other animals.

Any antidepressant may be used in combination with dextromethorphan to improve the therapeutic properties of dextromethorphan. Dextromethorphan and the antidepressant compound may be administered in separate compositions or dosage forms or may be administered in a single composition or dosage form comprising both.

A quinidine may be co-administered with dextromethorphan to provide enhanced plasma levels of dextromethorphan. For a combination of a quinidine and a dextromethorphan (including deuterium-modified dextromethorphan, e.g. d6-dextromethorphan, and non-deuterium modified dextromethorphan), a daily dose of about 1-1,000 mg, 1-10 mg, 10 mg, about 5 mg, about 4.5, about 1-3 mg, about 2-4 mg, about 3-5 mg, about 4-6 mg, about 5-7 mg, about 6-8 mg, about 7-9 mg, about 8-10 mg, about 9-11 mg, about 10-12 mg, about 4.5-5 mg, 20 mg, 30 mg, 30-100 mg, about 40 mg, about 50 mg, about 60 mg, about 70 mg, about 80 mg, about 90 mg, about 10-30 mg, about 30-50 mg, about 50-70 mg, about 10-90 mg of the quinidine, or any dose in a range bounded by any of these values.

Antidepressant compounds that can be co-administered with dextromethorphan include, but are not limited to, bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, ketamine, etc., or a metabolite or prodrug of any of these compounds, or a pharmaceutically acceptable salt of any of these compounds.

For a combination of a ketamine and a dextromethorphan (including deuterium-modified dextromethorphan, e.g. d6-dextromethorphan, and non-deuterium modified dextromethorphan), a daily dose of about 0.01-0.2 mg, about 0.2-0.4 mg, about 0.4-0.6 mg, about 0.6-0.8 mg, about 0.8-1 mg, about 1-1.2 mg, about 1.2-1.4 mg, about 1.4-1.6 mg, about 1.6-1.8 mg, about 1.8-2 mg, about 2-2.2 mg, about 2.2-2.4 mg, about 2.4-2.6 mg, about 2.6-2.8 mg, about 2.8-3 mg, about 3-3.2 mg, about 3.2-3.4 mg, about 3.4-3.6 mg, about 3.6-3.8 mg, about 3.8-4 mg, about 3.9-4.1 mg, about 4-4.2 mg, about 0.2-0.4 mg, about 0.2-0.6 mg, about 0.2-0.8 mg, about 0.2-1 mg, about 0.2-1.2 mg, about 0.2-1.4 mg, about 0.2-1.6 mg, about 0.2-1.8 mg, about 0.2-2.0 mg, 0.2-2.5 mg, about 0.2-3.0 mg, about 0.2-3.5 mg, about 0.2-4.0 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 10-500 mg, about 50-400 mg, about 50-300 mg, about 100-250 mg, about 1-10 mg, about 10-200 mg, about 10-150 mg, about 10-100 mg, about 10-180 mg, about 10-160 mg, about 10-140 mg, about 10-120 mg, about 10-100 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220, about 220-240, about 240-250 mg, about 250-260 mg, about 260-280 mg, about 280-300 mg, about 300-350 mg, about 350-400 mg, about 25 mg, about 50 mg, about 100 mg, about 250 mg, of the ketamine, or any dose in a range bounded by any of these values, may be administered.

For a combination of a tesofensine and a dextromethorphan (including deuterium-modified dextromethorphan, e.g. d6-dextromethorphan, and non-deuterium modified dextromethorphan), a daily dose of about 0.1-0.2 mg, about 0.1-0.3 mg, about 0.1-0.4 mg, about 0.1-0.5 mg, about 0.1-0.6 mg, about 0.1-0.7 mg, about 0.1-0.8 mg, about 0.1-0.9 mg, about 0.1-0.1 mg, about 0.1-0.12 mg, 0.01-0.2 mg, 0.1-0.3 mg, about 0.2-0.4 mg, about 0.3-0.5 mg, about 0.4-0.6 mg, about 0.5-0.7 mg, about 0.6-0.8 mg, about 0.7-0.9 mg, about 0.8-1 mg, about 0.9-1.1 mg, of the tesofensine, or any dose in a range bounded by any of these values, may be administered.

For a combination of a brasofensine and a dextromethorphan (including deuterium-modified dextromethorphan, e.g. d6-dextromethorphan, and non-deuterium modified dextromethorphan), a daily dose of about 0.01-0.2 mg, about 0.2-0.4 mg, about 0.4-0.6 mg, about 0.6-0.8 mg, about 0.8-1 mg, about 1-1.2 mg, about 1.2-1.4 mg, about 1.4-1.6 mg, about 1.6-1.8 mg, about 1.8-2 mg, about 2-2.2 mg, about 2.2-2.4 mg, about 2.4-2.6 mg, about 2.6-2.8 mg, about 2.8-3 mg, about 3-3.2 mg, about 3.2-3.4 mg, about 3.4-3.6 mg, about 3.6-3.8 mg, about 3.8-4 mg, about 3.9-4.1 mg, about 4-4.2 mg, about 0.2-0.4 mg, about 0.2-0.6 mg, about 0.2-0.8 mg, about 0.2-1 mg, about 0.2-1.2 mg, about 0.2-1.4 mg, about 0.2-1.6 mg, about 0.2-1.8 mg, about 0.2-2.0 mg, 0.2-2.5 mg, about 0.2-3.0 mg, about 0.2-3.5 mg, about 0.2-4.0 mg, of the brasofensine, or any dose in a range bounded by any of these values, may be administered.

For a combination of a clomipramine and a dextromethorphan (including deuterium-modified dextromethorphan, e.g. d6-dextromethorphan, and non-deuterium modified dextromethorphan), a daily dose of about 10-500 mg, about 50-400 mg, about 50-300 mg, about 100-250 mg, about 1-10 mg, about 10-200 mg, about 10-150 mg, about 10-100 mg, about 10-180 mg, about 10-160 mg, about 10-140 mg, about 10-120 mg, about 10-100 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-350 mg, about 350-400 mg, about 25 mg, about 50 mg, about 100 mg, about 250 mg, of the clomipramine, or any dose in a range bounded by any of these values, may be administered.

For a combination of a doxepin and a dextromethorphan (including deuterium-modified dextromethorphan, e.g. d6-dextromethorphan, and non-deuterium modified dextromethorphan), a daily dose of about 1-500 mg, about 1-10 mg, about 1-40 mg, about 1-30 mg, about 1-20 mg, about 1-18 mg, about 1-16 mg, about 1-14 mg, about 1-12 mg, about 1-10 mg, about 10-150 mg, about 10-125 mg, about 10-100 mg, about 10-75 mg, about 10-70 mg, about 10-60 mg, about 10-50 mg, about 10-40 mg, about 10-30 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 25 mg, about 50 mg, about 75 mg, about 100 mg, about 150 mg, about 250 mg, about 300 mg, of the doxepin, or any dose in a range bounded by any of these values, may be administered.

For a combination of a fluoxetine and a dextromethorphan (including deuterium-modified dextromethorphan, e.g. d6-dextromethorphan, and non-deuterium modified dextromethorphan), a daily dose of a daily dose of about 1-10 mg, about 5-15 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 10 mg, about 20 mg, about 60 mg, about 100 mg, about 150 mg, of the fluoxetine, or any dose in a range bounded by any of these values, may be administered.

For a combination of a mianserin and a dextromethorphan (including deuterium-modified dextromethorphan, e.g. d6-dextromethorphan, and non-deuterium modified dextromethorphan), a daily dose of about 1-300 mg, about 1-90 mg, about 1-60 mg, about 1-30 mg, about 1-25 mg, about 1-20 mg, about 1-15 mg, about 1-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 30 mg, about 60 mg, about 90 mg, about 120 mg, about 150 mg, of the mianserin, or any dose in a range bounded by any of these values, may be administered.

For a combination of a imipramine and a dextromethorphan (including deuterium-modified dextromethorphan, e.g. d6-dextromethorphan, and non-deuterium modified dextromethorphan), a daily dose of about 1-10 mg, about 5-150 mg, about 5-125 mg, about 5-100 mg, about 5-75 mg, about 5-60 mg, about 5-50 mg, about 5-40 mg, about 5-30 mg, about 5-25 mg, about 5-20 mg, about 5-15 mg, about 10-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 25 mg, about 50 mg, about 75 mg, about 100 mg, about 150 mg, about 250 mg, about 300 mg, of the imipramine, or any dose in a range bounded by any of these values, may be administered.

For a combination of a 2-chloroimipramine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the about 2-chloroimipramine, or any dose in a range bounded by any of these values, may be administered.

For a combination of an amitriptyline and a dextromethorphan (including deuterium-modified dextromethorphan, e.g. d6-dextromethorphan, and non-deuterium modified dextromethorphan), a daily dose of about 1-10 mg, about 5-100 mg, about 5-70 mg, about 5-60 mg, about 5-50 mg, about 5-40 mg, about 5-35 mg, about 5-30 mg, about 5-25 mg, about 5-20 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the amitriptyline, or any dose in a range bounded by any of these values, may be administered.

For a combination of an amoxapine and a dextromethorphan (including deuterium-modified dextromethorphan, e.g. d6-dextromethorphan, and non-deuterium modified dextromethorphan), a daily dose of about 1-10 mg, about 10-20 mg, about 10-300 mg, about 10-250 mg, about 10-200 mg, about 10-150 mg, about 10-120 mg, about 10-100 mg, about 10-80 mg, about 10-60 mg, about 10-40 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 500-600 mg, about 600-700 mg, about 700-800 mg, about 25 mg, about 50 mg, about 75 mg, about 100 mg, about 150 mg, about 250 mg, about 300 mg, about 400 mg, of the amoxapine, or any dose in a range bounded by any of these values, may be administered.

For a combination of a desipramine and a dextromethorphan (including deuterium-modified dextromethorphan, e.g. d6-dextromethorphan, and non-deuterium modified dextromethorphan), a daily dose of about 1-10 mg, about 1-15 mg, about 10-20 mg, about 10-25 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 20-30 mg, about 20-40 mg, about 30-40 mg, about 40-50 mg, about 40-60 mg, about 50-60 mg, about 60-70 mg, about 70-80 mg, about 80-90 mg, about 90-100 mg, about 90-110 mg, about 100-120 mg, about 120-140 mg, about 140-160 mg, about 160-180 mg, about 180-200 mg, about 180-220 mg, about 200-220 mg, about 220-240 mg, about 240-250 mg, about 250-260 mg, about 260-280 mg, about 280-300 mg, about 280-320 mg, about 300-350 mg, about 350-400 mg, about 100-200 mg, about 25-100 mg, about 25 mg, about 50 mg, about 100 mg, about 200 mg, about 250 mg, of the desipramine, or any dose in a range bounded by any of these values, may be administered.

For a combination of a protriptyline and a dextromethorphan (including deuterium-modified dextromethorphan, e.g. d6-dextromethorphan, and non-deuterium modified dextromethorphan), a daily dose of about 5-100 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 15-60 mg, about 1-5 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 20 mg, about 30 mg, about 60 mg, about 100 mg, about 150 mg, of the protriptyline, or any dose in a range bounded by any of these values, may be administered.

For a combination of a trimipramine and a dextromethorphan (including deuterium-modified dextromethorphan, e.g. d6-dextromethorphan, and non-deuterium modified dextromethorphan), a daily dose of about 20-300 mg, about 1-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 100-200 mg, about 120-140 mg, about 140-160 mg, about 160-180 mg, about 180-200 mg, about 180-220 mg, about 200-220 mg, about 220-240 mg, about 240-250 mg, about 250-260 mg, about 260-280 mg, about 280-300 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the trimipramine, or any dose in a range bounded by any of these values, may be administered.

For a combination of a nortriptyline and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-15 mg, about 15-20 mg, about 20-25 mg, about 20-30 mg, about 25-30 mg, about 30-35 mg, about 30-50 mg, about 35-40 mg, about 40-45 mg, about 45-50 mg, about 50-150 mg, about 50-55 mg, about 55-60 mg, about 60-65 mg, about 65-70 mg, about 70-80 mg, about 80-90 mg, about 80-120 mg, about 90-100 mg, about 100-120 mg, about 120-140 mg, about 140-160 mg, about 160-180 mg, about 180-200 mg, about 10 mg, about 20 mg, about 30 mg, about 60 mg, about 100 mg, about 150 mg, of the nortriptyline, or any dose in a range bounded by any of these values, may be administered.

For a combination of a maprotiline and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-15 mg, about 10-250 mg, about 10-75 mg, about 10-50 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 60-90 mg, about 65-70 mg, about 70-75 mg, about 75-80 mg, about 80-85 mg, about 80-120 mg, about 85-90 mg, about 90-100 mg, about 100-120 mg, about 100-150 mg, about 120-125 mg, about 125-140 mg, about 140-150 mg, about 150-160 mg, about 160-180 mg, about 180-200 mg, about 200-225 mg, about 210-240 mg, about 200-250 mg, about 10 mg, about 25 mg, about 30 mg, about 50 mg, about 75 mg, about 100 mg, about 150 mg, about 225 mg, of the maprotiline, or any dose in a range bounded by any of these values, may be administered.

For a combination of a phenelzine and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-90 mg, about 10-15 mg, about 15-20 mg, about 20-25 mg, about 25-30 mg, about 30-35 mg, about 35-40 mg, about 40-45 mg, about 40-50 mg, about 45-50 mg, about 50-55 mg, about 50-70 mg, about 50-200 mg, about 55-60 mg, about 60-65 mg, about 60-90 mg, about 65-70 mg, about 70-80 mg, about 80-90 mg, 80-120 mg, about 90-100 mg, about 100-120 mg, about 100-150 mg, about 120-140 mg, about 140-160 mg, about 160-180 mg, about 180-200 mg, about 10 mg, about 15 mg, about 30 mg, about 60 mg, about 100 mg, about 150 mg, of the phenelzine, or any dose in a range bounded by any of these values, may be administered.

For a combination of a isocarboxazid and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 5-10 mg, about 5-15 mg, about 10-15 mg, about 10-60 mg, about 15-20 mg, about 20-25 mg, about 25-30 mg, about 30-35 mg, about 30-50 mg, about 35-40 mg, about 40-45 mg, about 45-50 mg, about 50-55 mg, about 50-70 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 30 mg, about 60 mg, about 100 mg, about 150 mg, of the isocarboxazid, or any dose in a range bounded by any of these values, may be administered.

For a combination of a tranylcypromine and a dextromethorphan (including deuterium-modified dextromethorphan, e.g. d6-dextromethorphan, and non-deuterium modified dextromethorphan), a daily dose of about 1-5 mg, about 1-30 mg, about 1-25 mg, about 1-20 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 30 mg, about 60 mg, about 100 mg, about 150 mg, of the tranylcypromine, or any dose in a range bounded by any of these values, may be administered.

For a combination of a paroxetine and a dextromethorphan (including deuterium-modified dextromethorphan, e.g. d6-dextromethorphan, and non-deuterium modified dextromethorphan), a daily dose of about 1-5 mg, about 1-50 mg, about 1-20 mg, about 1-15 mg, about 1-10 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-30 mg, about 2-40 mg, about 2-50 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 60 mg, about 100 mg, about 150 mg, of the paroxetine, or any dose in a range bounded by any of these values, may be administered.

For a combination of a trazodone and a dextromethorphan (including deuterium-modified dextromethorphan, e.g. d6-dextromethorphan, and non-deuterium modified dextromethorphan), a daily dose of about 1-10 mg, about 10-20 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 10-250 mg, about 10-300 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 25 mg, about 50 mg, about 75 mg, about 100 mg, about 150 mg, about 250 mg, about 300 mg, about 400 mg, about 600 mg, of the trazodone, or any dose in a range bounded by any of these values, may be administered.

For a combination of a citalopram and a dextromethorphan (including deuterium-modified dextromethorphan, e.g. d6-dextromethorphan, and non-deuterium modified dextromethorphan), a daily dose of about 1-5 mg, about 1-20 mg, about 1-15 mg, about 1-10 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-25 mg, about 2-30 mg, about 2-35 mg, about 2-40 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 150 mg, of the citalopram, or any dose in a range bounded by any of these values, may be administered.

For a combination of a sertraline and a dextromethorphan (including deuterium-modified dextromethorphan, e.g. d6-dextromethorphan, and non-deuterium modified dextromethorphan), a daily dose of about 1-5 mg, about 1-50 mg, about 1-45 mg, about 1-40 mg, about 1-30 mg, about 1-20 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-75 mg, about 75-80 mg, about 80-85 mg, about 85-90 mg, about 90-100 mg, about 100-120 mg, about 120-125 mg, about 125-140 mg, about 140-150 mg, about 150-160 mg, about 160-180 mg, about 180-200 mg, about 200-300 mg, about 10 mg, about 25 mg, about 30 mg, about 50 mg, about 75 mg, about 100 mg, about 150 mg, about 200 mg, about 225 mg, of sertraline, or any dose in a range bounded by any of these values, may be administered.

For a combination of an aryloxy indanamine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the aryloxy indanamine, or any dose in a range bounded by any of these values, may be administered.

For a combination of a benactyzine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the benactyzine, or any dose in a range bounded by any of these values, may be administered.

For a combination of a escitalopram and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-12 mg, about 2-14 mg, about 2-15 mg, about 2-20 mg, about 5-10 mg, about 5-15 mg, about 10-15 mg, about 10-30 mg, about 15-20 mg, about 15-30 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-200 mg, about 5 mg, about 10 mg, about 15 mg, about 20 mg, about 25 mg, about 30 mg, about 35 mg, about 40 mg, about 50 mg, of the escitalopram, or any dose in a range bounded by any of these values, may be administered.

For a combination of a fluvoxamine and a dextromethorphan (including deuterium-modified dextromethorphan, e.g. d6-dextromethorphan, and non-deuterium modified dextromethorphan), a daily dose of 50-300 mg, 1-10 mg, about 10-20 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 10-250 mg, about 10-300 mg, about 20-30 mg, about 30-40 mg, about 40-50 mg, about 50-60 mg, about 60-70 mg, about 70-80 mg, about 80-90 mg, about 90-100 mg, about 90-110 mg, about 100-120 mg, about 120-140 mg, about 140-160 mg, about 160-180 mg, about 180-200 mg, about 180-220 mg, about 200-220 mg, about 220-240, about 240-250 mg, about 240-260 mg, about 250-260 mg, about 260-280 mg, about 280-300 mg, about 280-320 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the fluvoxamine, or any dose in a range bounded by any of these values, may be administered.

For a combination of a venlafaxine and a dextromethorphan (including deuterium-modified dextromethorphan, e.g. d6-dextromethorphan, and non-deuterium modified dextromethorphan), a daily dose of about 1-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 120-180 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 25 mg, about 50 mg, about 75 mg, about 100 mg, about 150 mg, about 225, about 250 mg, about 375 mg, about 400 mg, about 600 mg, of the venlafaxine, or any dose in a range bounded by any of these values, may be administered.

For a combination of a desvenlafaxine and a dextromethorphan (including deuterium-modified dextromethorphan, e.g. d6-dextromethorphan, and non-deuterium modified dextromethorphan), a daily dose of about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-30 mg, about 2-35 mg, about 2-40 mg, about 2-45 mg, about 2-50 mg, about 2-75 mg, about 2-100 mg, about 1-5 mg, about 5-10 mg, about 10-15 mg, about 15-20 mg, about 20-25 mg, about 20-30 mg, about 25-30 mg, about 30-35 mg, about 35-40 mg, about 40-45 mg, about 40-60 mg, about 45-50 mg, about 50-55 mg, about 55-60 mg, about 60-65 mg, about 65-70 mg, about 70-80 mg, about 80-90 mg, about 80-120 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 150 mg, of the desvenlafaxine, or any dose in a range bounded by any of these values, may be administered.

For a combination of a duloxetine and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-60 mg, about 2-90 mg, about 2-120 mg, about 5-10 mg, about 10-15 mg, about 15-20 mg, about 20-25 mg, about 20-40 mg, about 25-30 mg, about 30-35 mg, about 30-50 mg, about 35-40 mg, about 40-45 mg, about 45-50 mg, about 50-55 mg, about 50-70 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 120 mg, of the duloxetine, or any dose in a range bounded by any of these values, may be administered.

For a combination of a mirtazapine and a dextromethorphan (including deuterium-modified dextromethorphan, e.g. d6-dextromethorphan, and non-deuterium modified dextromethorphan), a daily dose of about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-25 mg, about 2-30 mg, about 2-35 mg, about 2-40 mg, about 2-45 mg, about 1-5 mg, about 5-10 mg, about 5-100 mg, about 10-15 mg, about 10-50 mg, about 15-20 mg, about 15-45 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 45 mg, about 60 mg, about 75 mg, of the mirtazapine, or any dose in a range bounded by any of these values, may be administered.

For a combination of a nefazodone and a dextromethorphan (including deuterium-modified dextromethorphan, e.g. d6-dextromethorphan, and non-deuterium modified dextromethorphan), a daily dose of about 1-10 mg, about 10-20 mg, about 20-40 mg, about 20-50 mg, about 20-60 mg, about 20-70 mg, about 20-80 mg, about 20-90 mg, about 20-100 mg, about 20-120 mg, about 20-140 mg, about 20-160 mg, about 20-180 mg, about 20-200 mg, about 20-250 mg, about 20-300 mg, about 20-450 mg, about 20-600 mg, about 20-25 mg, about 25-30 mg, about 30-40 mg, about 40-50 mg, about 50-60 mg, about 60-70 mg, about 70-80 mg, about 80-90 mg, about 80-120 mg, about 90-100 mg, about 100-120 mg, about 120-140 mg, about 140-150 mg, about 150-160 mg, about 160-180 mg, about 160-240 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-1000 mg, about 1000-1500 mg, about 25 mg, about 50 mg, about 75 mg, about 100 mg, about 150 mg, about 250 mg, about 300 mg, about 400 mg, about 600 mg, of the nefazodone, or any dose in a range bounded by any of these values, may be administered.

For a combination of a selegiline and a dextromethorphan (including deuterium-modified dextromethorphan, e.g. d6-dextromethorphan, and non-deuterium modified dextromethorphan), a daily dose of about 0.5-2 mg, about 2-5 mg, about 1-10 mg, about 1-9 mg, about 1-8 mg, about 1-7 mg, about 1-6 mg, about 1-5 mg, about 1-3 mg, about 3-5 mg, about 5-10 mg, about 5-15 mg, about 10-15 mg, about 15-25 mg, about 25-30 mg, about 30-35 mg, about 35-40 mg, about 40-45 mg, about 45-50 mg, about 5 mg, about 10 mg, about 15 mg, about 20 mg, about 30 mg, about 40 mg, of the selegiline, or any dose in a range bounded by any of these values, may be administered.

For a combination of a sibutramine and a dextromethorphan (including deuterium-modified dextromethorphan, e.g. d6-dextromethorphan, and non-deuterium modified dextromethorphan), a daily dose of about 1-5 mg, about 1-15 mg, about 1-10 mg, about 1-8 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 5 mg, about 10 mg, about 15 mg, about 20 mg, about 30 mg, about 40 mg, about 60 mg, about 100 mg, about 120 mg, of the sibutramine, or any dose in a range bounded by any of these values, may be administered.

For a combination of a rasagiline and a dextromethorphan (including deuterium-modified dextromethorphan, e.g. d6-dextromethorphan, and non-deuterium modified dextromethorphan), a daily dose of about 0.1-0.3 mg, about 0.3-0.5 mg, about 0.3-0.7 mg, about 0.5-0.7 mg, about 0.5-1.5 mg, about 0.7-0.9 mg, about 0.9-1.0 mg, about 1.0-1.5 mg, about 1.5-2.0 mg, about 2.0-3.0 mg, about 0.1 mg, about 0.25 mg, about 0.5 mg, about 0.75 mg, about 1 mg, about 2 mg, of the rasagiline, or any dose in a range bounded by any of these values, may be administered.

For a combination of a milnacipran and a dextromethorphan (including deuterium-modified dextromethorphan, e.g. d6-dextromethorphan, and non-deuterium modified dextromethorphan), a daily dose of about 1-7.5 mg, about 7.5-12.5 mg, about 5-20 mg, about 5-100 mg, about 5-90 mg, about 5-80 mg, about 5-70 mg, about 5-60 mg, about 5-50 mg, about 5-40 mg, about 12.5-15 mg, about 15-20 mg, about 20-30 mg, about 20-25 mg, about 25-30 mg, about 30-35 mg, about 35-40 mg, about 40-45 mg, about 45-50 mg, about 50-55 mg, about 40-60 mg, about 55-60 mg, about 60-65 mg, about 65-70 mg, about 70-80 mg, about 80-90 mg, about 90-100 mg, about 80-120 mg, about 100-120 mg, about 120-140 mg, about 140-160 mg, about 160-180 mg, about 180-200 mg, about 180-220 mg, about 200-300 mg, about 300-400 mg, about 7.5 mg, about 12.5 mg, about 25 mg, about 50 mg, about 75 mg, about 60 mg, about 100 mg, about 200 mg, of the milnacipran, or any dose in a range bounded by any of these values, may be administered.

For a combination of a moclobemide and a dextromethorphan (including deuterium-modified dextromethorphan, e.g. d6-dextromethorphan, and non-deuterium modified dextromethorphan), a daily dose of about 1-10 mg, about 10-20 mg, about 20-25 mg, about 20-450 mg, about 20-300 mg, about 20-250 mg, about 20-200 mg, about 20-150 mg, about 20-100 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-320 mg, about 280-300 mg, about 300-320 mg, about 320-350 mg, about 350-400 mg, about 430-470 mg, about 400-450 mg, about 450-500 mg, about 500-550 mg, about 550-600 mg, about 600-650 mg, about 650-700 mg, about 25 mg, about 50 mg, about 75 mg, about 100 mg, about 150 mg, about 250 mg, about 300 mg, about 400 mg, about 600 mg, of the moclobemide, or any dose in a range bounded by any of these values, may be administered.

For a combination of a nialamide and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the nialamide, or any dose in a range bounded by any of these values, may be administered.

For a combination of a iproniazid and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iproniazid, or any dose in a range bounded by any of these values, may be administered.

For a combination of a iproclozide and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iproclozide, or any dose in a range bounded by any of these values, may be administered.

For a combination of a toloxatone and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the toloxatone, or any dose in a range bounded by any of these values, may be administered.

For a combination of a butriptyline and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the butriptyline, or any dose in a range bounded by any of these values, may be administered.

For a combination of a dosulepin and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dosulepin, or any dose in a range bounded by any of these values, may be administered.

For a combination of a dibenzepin and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dibenzepin, or any dose in a range bounded by any of these values, may be administered.

For a combination of a iprindole and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iprindole, or any dose in a range bounded by any of these values, may be administered.

For a combination of a lofepramine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the lofepramine, or any dose in a range bounded by any of these values, may be administered.

For a combination of a opipramol and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the opipramol, or any dose in a range bounded by any of these values, may be administered.

For a combination of a norfluoxetine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the norfluoxetine, or any dose in a range bounded by any of these values, may be administered.

For a combination of a dapoxetine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dapoxetine, or any dose in a range bounded by any of these values, may be administered.

Bupropion has the structure shown below (bupropion hydrochloride form shown).

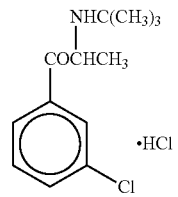

Combining bupropion with dextromethorphan may provide greater efficacy, such as greater pain relief, than would otherwise be achieved by administering either component alone. In extensive metabolizers, dextromethorphan can be rapidly and extensively metabolized, yielding low systemic exposure even at high doses. Bupropion, besides possessing anti-depressant and analgesic properties, is an inhibitor of dextromethorphan metabolism. Bupropion is a dopamine and norepinephrine reuptake inhibitor. It can also be a nicotinic acetylcholine receptor antagonist, and it can modulate cytokines associated with inflammatory diseases. Bupropion can affect levels of tumor necrosis factor-alpha and interferon-gamma. Metabolites of bupropion, which include hydroxybupropion, threohydroxybupropion (also known as threohydrobupropion or threodihydrobupropion), and erythrohydroxybupropion (also known as erythrohydrobupropion or erythrodihydrobupropion), are also inhibitors of dextromethorphan metabolism. Thus, bupropion, including a form of bupropion that is rapidly converted in the body (such as a salt, hydrate, solvate, polymorph, etc.), is a prodrug of hydroxybupropion, threohydroxybupropion, and erythrohydroxybupropion. Prodrugs of bupropion can include N-methylbupropion and N-benzylbupropion.

As explained above, this inhibition may augment dextromethorphan plasma levels, resulting in additive or synergistic efficacy such as relief of neurological disorders including pain, depression, smoking cessation, etc. Thus, while inhibition of dextromethorphan metabolism is only one of many potential benefits of the combination, co-administration of dextromethorphan with bupropion may thereby enhance the efficacy of bupropion for many individuals. Co-administration of dextromethorphan with bupropion may enhance the analgesic properties of bupropion for many individuals. Co-administration of dextromethorphan with bupropion may also enhance the anti-depressant properties of bupropion for many individuals, including faster onset of action.

Another potential benefit of co-administration of dextromethorphan and bupropion is that it may be useful to reduce the potential for an adverse event, such as somnolence, associated with treatment by dextromethorphan. This may be useful, for example, in human patients at risk of experiencing the adverse event as a result of being treated with dextromethorphan.

Another potential benefit of co-administration of dextromethorphan and bupropion is that it may be useful to reduce the potential for an adverse event, such as seizure, associated with treatment by bupropion, hydroxybupropion, erythrohydroxybupropion, threohydroxybupropion, or a metabolite or prodrug of any of these compounds. This may be useful, for example, in human patients at risk of experiencing the adverse event as a result of being treated with bupropion, hydroxybupropion, erythrohydroxybupropion, threohydroxybupropion, or a metabolite or prodrug of any of these compounds.

With respect to dextromethorphan, bupropion, hydroxybupropion, erythrohydroxybupropion, threohydroxybupropion, or a metabolite or prodrug of any of these compounds, co-administration may reduce a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and/or tongue protrusion.

Gastrointestinal adverse events include, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

Co-administering dextromethorphan and an antidepressant, such as bupropion, hydroxybupropion, erythrohydroxybupropion, threohydroxybupropion, or a metabolite or prodrug of any of these compounds, does not necessarily require that the two compounds be administered in the same dosage form. For example, the two compounds may be administered in a single dosage form, or they may be administered in two separate dosage forms. Additionally, the two compounds may be administered at the same time, but this is not required. The compounds can be given at different times as long as both are in a human body at the same time for at least a portion of the time that treatment by co-administration is being carried out.

Side effects of bupropion, hydroxybupropion, erythrohydroxybupropion, threohydroxybupropion, and/or dextromethorphan may be reduced by administering bupropion, hydroxybupropion, erythrohydroxybupropion, or threohydroxybupropion, with dextromethorphan. Examples of side effects that may be reduced include abnormal sensation of rotation and movement, agitation, arm weakness, bloating, blurred vision, burning sensation in the eyes, buzzing sound(s) in the ear(s), changes in vital signs (including, but not limited to, heart rate, respiratory rate, body temperature, and blood pressure), cold sensation, constipation, difficulty concentrating, difficulty sleeping, difficulty in falling asleep, difficulty urinating, difficulty with bowel movement, discomfort in the ear, discomfort in the eye, discomfort in the stomach, dizziness, dry lips, dry mouth, dry throat, dysmenorrhea, fatigue, feeling feverish, feeling heavy headed, feeling more agitated than usual, feeling more tired than usual, feeling tired, hand tremors, hand weakness, headache, heartburn, hot flashes, increased blood pressure, increased skin sensitivity, increased skin sensitivity at head and face, involuntary muscle contraction, involuntary muscle contractions all over the body, knee pain, leg weakness, lightheadedness, loose stool, loss of appetite, low back pain, menstrual disorder, metallic taste, more saliva than usual, mucosal dryness, nasal congestion, nausea, runny nose, sensation of light pressure sensation in the eyes, shivers when stretching or yawning, skin sensitivity, skin sensitivity in arm, face, and/or head, sleep difficulties, soft stools, stomach ache, stomach discomfort, sweaty hands and/or feet, throat irritation, throat pain, tinnitus, tremors, and/or weakness. Any of these side effects may also be referred to, or grouped, according to a corresponding, equivalent, or otherwise relevant term found in the Medical Dictionary for Regulatory Activities (MedRA).

In some embodiments, co-administration of a combination of bupropion, hydroxybupropion, erythrohydroxybupropion, threohydroxybupropion, or a metabolite or prodrug of any of these compounds, and dextromethorphan results in both bupropion, hydroxybupropion, erythrohydroxybupropion, threohydroxybupropion, or a metabolite or prodrug of any of these compounds, and dextromethorphan contributing to the pain relieving properties of the combination. For example, the combination may have improved pain relieving properties as compared to bupropion, hydroxybupropion, erythrohydroxybupropion, threohydroxybupropion, or a metabolite or prodrug of any of these compounds, alone or compared to dextromethorphan alone, including potentially faster onset of action.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to bupropion, hydroxybupropion, erythrohydroxybupropion, threohydroxybupropion, or a metabolite or prodrug of any of these compounds, alone.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to as compared to dextromethorphan alone.

Unless otherwise indicated, any reference to a compound herein, such as dextromethorphan, bupropion, hydroxybupropion, erythrohydroxybupropion, threohydroxybupropion, by structure, name, or any other means, includes pharmaceutically acceptable salts; alternate solid forms, such as polymorphs, solvates, hydrates, etc.; tautomers; deuterium-modified compounds, such as deuterium modified dextromethorphan; or any chemical species that may rapidly convert to a compound described herein under conditions in which the compounds are used as described herein.

In some embodiments, an excess of one stereoisomer of bupropion, hydroxybupropion, erythrohydroxybupropion, threohydroxybupropion, or a metabolite or prodrug of any of these compounds may be administered. In other embodiments, an excess of the S-enantiomer (such as at least 60%, at least 70%, at least 75%, at least 80%, at least 85%, at least 90%, at least 95%, at least 99% or enantiomerically pure S-enantiomer) or an excess of the R-enantiomer (such as at least 60%, at least 70%, at least 75%, at least 80%, at least 85%, at least 90%, at least 95%, at least 99% or enantiomerically pure R-enantiomer) of bupropion, hydroxybupropion, erythrohydroxybupropion, threohydroxybupropion, or a metabolite or prodrug of any of these compounds may be administered.

Examples of deuterium-enriched bupropion, and/or enantiopure deuterium-enriched bupropion include, but are not limited to, those shown below.

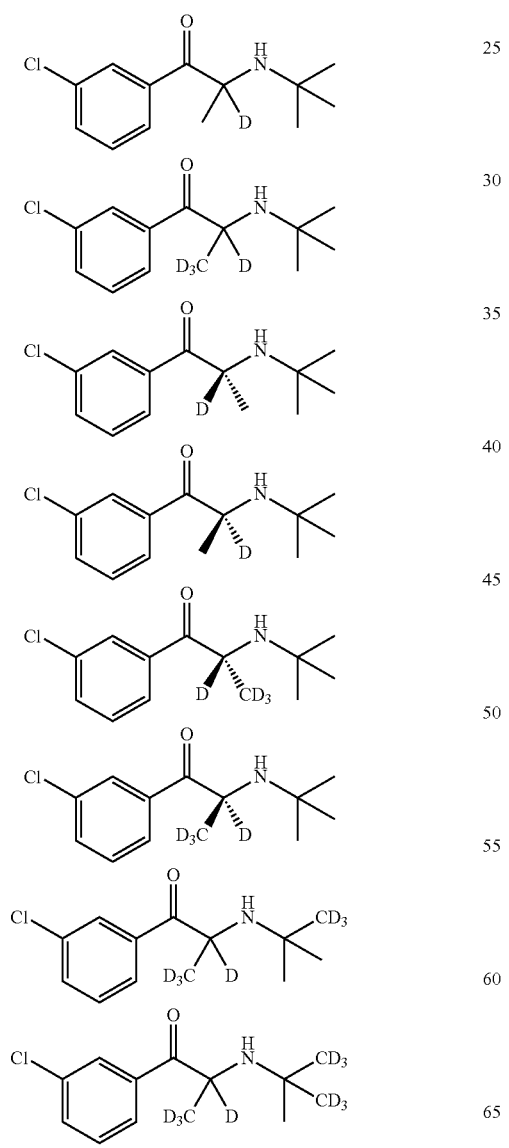

-continued

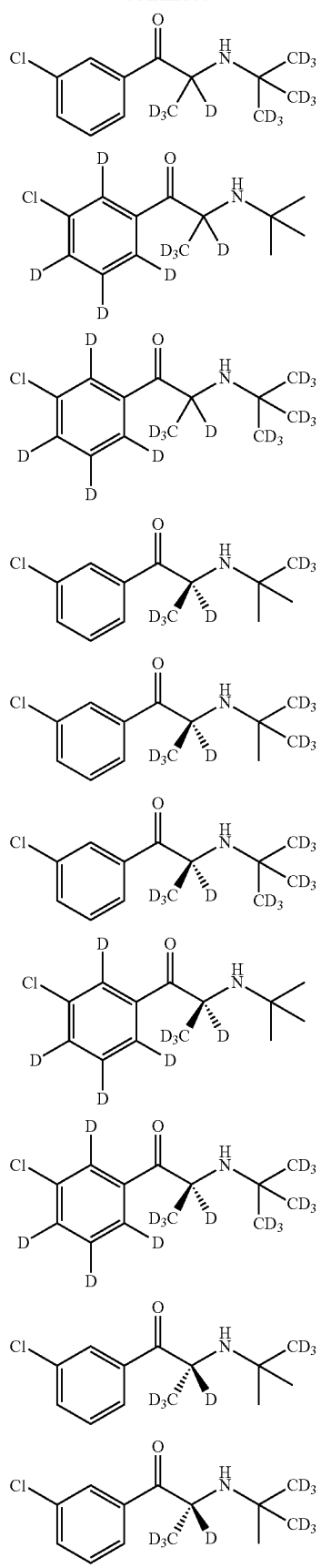

-continued

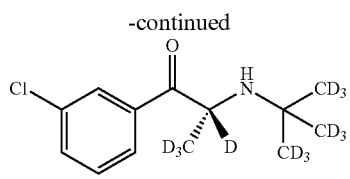

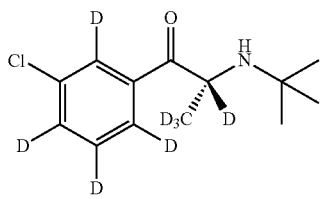

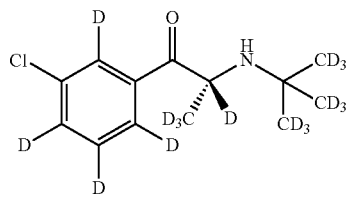

In some embodiments, both dextromethorphan and bupropion, hydroxybupropion, erythrohydroxybupropion, threohydroxybupropion, a metabolite, or prodrug of any of these compounds are formulated to be immediate release, and in other embodiments both bupropion, hydroxybupropion, erythrohydroxybupropion, threohydroxybupropion, a metabolite or prodrug of any of these compounds are formulated to be sustained release.

Examples of deuterium modified dextromethorphan include, but are not limited to, those shown below.

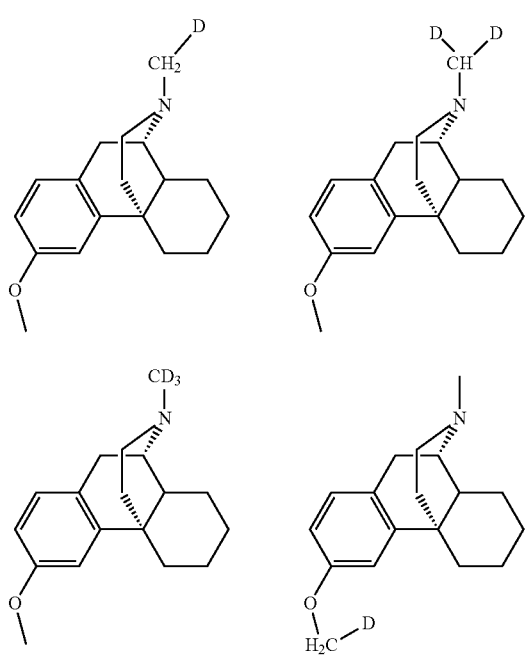

-continued

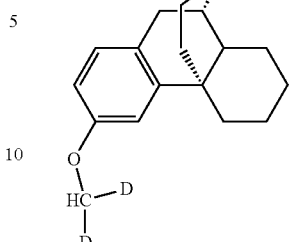

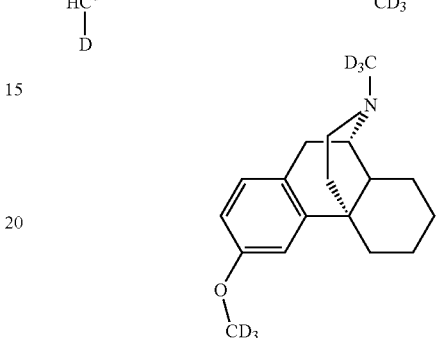

d6-dextromethorphan

A dosage form or a composition may be a blend or mixture of dextromethorphan and a compound that inhibits the metabolism of dextromethorphan, such as bupropion, hydroxybupropion, erythrohydroxybupropion, threohydroxybupropion, or a metabolite or prodrug of any of these compounds, either alone or within a vehicle. For example, dextromethorphan and bupropion may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, dextromethorphan and bupropion may be substantially uniformly dispersed within a composition or dosage form. Alternatively, dextromethorphan and bupropion may be in separate domains or phases within a composition or dosage form. For example, one drug may be in a coating and another drug may be in a core within the coating. For example, one drug may be formulated for sustained release and another drug may be formulated for immediate release.

Some embodiments include administration of a tablet that contains bupropion in a form that provides sustained release and dextromethorphan in a form that provides immediate release. While there are many ways that sustained release of bupropion may be achieved, in some embodiments, bupropion is combined with hydroxypropyl methylcellulose. For example, particles of bupropion hydrochloride could be blended with microcrystalline cellulose and hydroxypropyl methylcellulose (e.g., METHOCEL®) to form an admixture of blended powders. This could then be combined with immediate release dextromethorphan in a single tablet.

Dextromethorphan and/or an antidepressant, such as bupropion, hydroxybupropion, threohydroxybupropion and erythrohydroxybupropion, or a non-bupropion antidepressant (all of which are referred to collectively herein as "therapeutic compounds" for convenience) may be combined with a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a human patient in a variety of forms adapted to the chosen route of administration, e.g., orally, or parenterally. Parenteral administration in this respect includes administration by the following routes: intravenous, intramuscular, subcutaneous, intraocular, intrasynovial, transepithelial including transdermal, ophthalmic, sublingual, and buccal; topically including ophthalmic, dermal, ocular, rectal and nasal inhalation via insufflation, aerosol and rectal systemic.

The ratio of dextromethorphan to bupropion may vary. In some embodiments, the weight ratio of dextromethorphan to bupropion may be about 0.1 to about 10, about 0.1 to about 2, about 0.2 to about 1, about 0.1 to about 0.5, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values. A ratio of 0.1 indicates that the weight of dextromethorphan is 1/10 that of bupropion. A ratio of 10 indicates that the weight of dextromethorphan is 10 times that of bupropion.

The amount of dextromethorphan in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of dextromethorphan.

Some liquid dosage forms may contain about 10 mg to about 500 mg, about 30 mg to about 350 mg, about 50 mg to about 200 mg, about 50 mg to about 70 mg, about 20 mg to about 50 mg, about 30 mg to about 60 mg, about 40 mg to about 50 mg, about 40 mg to about 55 mg, about 40 mg to about 42 mg, about 42 mg to about 44 mg, about 44 mg to about 46 mg, about 46 mg to about 48 mg, about 48 mg to about 50 mg, about 80 mg to about 100 mg, about 110 mg to about 130 mg, about 170 mg to about 190 mg, about 45 mg, about 60 mg, about 90 mg, about 120 mg, or about 180 mg of dextromethorphan, or any amount of dextromethorphan in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of dextromethorphan.

Some solid dosage forms may contain about 10 mg to about 500 mg, about 30 mg to about 350 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 50 mg to about 200 mg, about 50 mg to about 70 mg, about 80 mg to about 100 mg, about 110 mg to about 130 mg, about 170 mg to about 190 mg, about 60 mg, about 90 mg, about 120 mg, or about 180 mg of dextromethorphan, or any amount of dextromethorphan in a range bounded by, or between, any of these values.

In some embodiments, the amount of dextromethorphan may range from about 0.1 mg/kg to about 20 mg/kg, about 0.75 mg/kg to about 7.5 mg/kg, about 0.1 mg/kg to about 5 mg/kg, about 0.1 mg/kg to about 3 mg/kg, about 0.3 mg/kg to about 0.9 mg/kg, about 0.3 mg/kg to about 1 mg/kg, about 0.6 mg/kg to about 0.8 mg/kg, about 0.7 mg/kg to about 0.8 mg/kg, about 0.75 mg/kg, about 0.4 mg/kg to about 1.5 mg/kg, about 1 mg/kg to about 2 mg/kg, about 10 mg/kg to about 20 mg/kg, about 12 mg/kg to about 17 mg/kg, about 15 mg/kg to about 20 mg/kg, about 1 mg/kg, about 1 mg/kg to about 10 mg/kg, or any value bounded by or in between these ranges based on the body weight of the patient.

The amount of bupropion, hydroxybupropion, erythrohydroxybupropion, threohydroxybupropion, or a metabolite or prodrug of any of these compounds, in a therapeutic composition may vary. If increasing the plasma level of dextromethorphan is desired, bupropion, hydroxybupropion, erythrohydroxybupropion, threohydroxybupropion, or a metabolite or prodrug of any of these compounds, should be administered in an amount that increases the plasma level of dextromethorphan. For example, bupropion, hydroxybupropion, erythrohydroxybupropion, threohydroxybupropion, or a metabolite or prodrug of any of these compounds, may be administered in an amount that results in a plasma concentration of dextromethorphan in the human being, on day 8, day 9, or day 10, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times, the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may be administered to a human being in an amount that results in a 12 hour area under the curve from the time of dosing ($AUC_{0-12}$), or average plasma concentration in the human being for the 12 hours following dosing ($C_{avg}$) of dextromethorphan, on day 8, day 9, or day 10, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may be administered to a human being in an amount that results in a maximum plasma concentration ($C_{max}$) of dextromethorphan in the human being, on day 8, day 9, or day 10, that is at least about 2 times, at least about 5 times, at least about 10 times, at least about 15 times, at least about 20 times, at least about 30 times, or at least about 40 times the plasma concentration of the same amount of dextromethorphan administered without bupropion, hydroxybupropion, erythrohydroxybupropion, threohydroxybupropion, or a metabolite or prodrug of any of these compounds.

For co-administration of bupropion, hydroxybupropion, threohydroxybupropion, erythrohydroxybupropion, or a metabolite or prodrug of any of these compounds, an increase in the dextromethorphan plasma level can occur on the first day that bupropion, hydroxybupropion, threohydroxybupropion, erythrohydroxybupropion, or a metabolite or prodrug of any of these compounds, is administered, as compared to the same amount of dextromethorphan administered without bupropion, hydroxybupropion, threohydroxybupropion, erythrohydroxybupropion, or a metabolite or prodrug of any of these compounds. For example, the dextromethorphan plasma level on the first day that bupropion, hydroxybupropion, threohydroxybupropion, erythrohydroxybupropion, or a metabolite or prodrug of any of these compounds, is administered may be at least about 1.5 times, at least about at least 2 times, at least about 2.5 times, at least about 3 times, at least about 4 times, at least about 5 times, at least about 6 times at least about 7 times, at least about 8 times, at least about 9 times, or at least about 10 times the level that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan AUC on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least twice the AUC that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $AUC_{0-12}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 15 ng·hr/mL, at least about 17 ng·hr/mL, at least about 19 ng·hr/mL, at least about 20 ng·hr/mL, at least about 22 ng·hr/mL, at least about 23 ng·hr/mL, at least about 24 ng·hr/mL, at least about 25 ng·hr/mL, at least about 26 ng·hr/mL, at least about 27 ng·hr/mL, at least about 28 ng·hr/mL, at least about 29 ng·hr/mL, at least about 30 ng·hr/mL, at least about 31 ng·hr/mL, at least about 32 ng·hr/mL, at least about 33 ng·hr/mL, at least about 34 ng·hr/mL, at least about 35 ng·hr/mL, at least about 36 ng·hr/mL, at least about 37 ng·hr/mL, at least about 38 ng·hr/mL, at least about 39 ng·hr/mL, at least about 40 ng·hr/mL, at least about 41 ng·hr/mL, at least about 42 ng·hr/mL, at least about 43 ng·hr/mL, at least about 44 ng·hr/mL, at least about 45 ng·hr/mL, at least about 46 ng·hr/mL, at least about 47 ng·hr/mL, at least about 48 ng·hr/mL, at least about 49 ng·hr/mL, at least about 50 ng·hr/mL, at least about 51 ng·hr/mL, at least about 52 ng·hr/mL, at least about 53 ng·hr/mL, at least about 54 ng·hr/mL, at least about 55 ng·hr/mL, at least about 56 ng·hr/mL, at least about or 56.7 ng·hr/mL, and may be up to 10,000 ng·hr/mL.

In some embodiments, the dextromethorphan $AUC_{0-12}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $AUC_{0-12}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $AUC_{0-12}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $C_{max}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least twice the $C_{max}$ that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $C_{max}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.0 ng/mL, at least about 1.5 ng/mL, at least about 2.0 ng/mL, at least about 2.5 ng/mL, at least about 3.0 ng/mL, at least about 3.1 ng/mL, at least about 3.2 ng/mL, at least about 3.3 ng/mL, at least about 3.4 ng/mL, at least about 3.5 ng/mL, at least about 3.6 ng/mL, at least about 3.7 ng/mL, at least about 3.8 ng/mL, at least about 3.9 ng/mL, at least about 4.0 ng/mL, at least about 4.1 ng/mL, at least about 4.2 ng/mL, at least about 4.3 ng/mL, at least about 4.4 ng/mL, at least about 4.5 ng/mL, at least about 4.6 ng/mL, at least about 4.7 ng/mL, at least about 4.8 ng/mL, at least about 4.9 ng/mL, at least about 5.0 ng/mL, at least about 5.1 ng/mL, at least about 5.2 ng/mL, at least about 5.3 ng/mL, at least about 5.4 ng/mL, at least about 5.5 ng/mL, at least about 5.6 ng/mL, at least about 5.7 ng/mL, at least about 5.8 ng/mL, at least about 5.9 ng/mL, at least about 6.0 ng/mL, at least about 6.1 ng/mL, at least about 6.2 ng/mL, at least about 6.3 ng/mL, at least about 6.4 ng/mL, at least about 6.5 ng/mL, at least about 6.6 ng/mL, at least about 6.7 ng/mL, at least about 6.8 ng/mL, at least about 6.9 ng/mL, at least about 7.0 ng/mL, at least about 7.1 ng/mL, at least about 7.2 ng/mL, at least about 7.3 ng/mL, at least about 7.4 ng/mL, at least about 7.5 ng/mL, at least about 7.6 ng/mL, at least about 7.7 ng/mL, at least about 7.8 ng/mL, at least about 7.9 ng/mL, at least about 8.0 ng/mL, at least about 8.1 ng/mL, at least about 8.2 ng/mL, at least about 8.3 ng/mL, at least about 8.4 ng/mL, at least about 8.5 ng/mL, at least about 8.6 ng/mL, or at least about 8.7 ng/mL, and, in some embodiments, may be up to about 1000 ng·hr/mL.

In some embodiments, the dextromethorphan $C_{max}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, the dextromethorphan $C_{max}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, the dextromethorphan $C_{max}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, bupropion, hydroxybupropion, threohydroxybupropion, erythrohydroxybupropion, or a metabolite or prodrug of any of these compounds, is administered in an amount that results in a $C_{avg}$ of dextromethorphan, over the period between two separate and consecutive administrations of dextromethorphan, that is at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. For example, if dextromethorphan is administered at 8 am and at 8 pm on day 1, and no dextromethorphan is administered after 8 am and before 8 pm on day 1, the period between two separate and consecutive administrations of dextromethorphan is from immediately after 8 am to immediately before 8 pm on day 1.

In some embodiments, the dextromethorphan $C_{avg}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 8, the $C_{avg}$ can be for 12 hours after the first dose of dextromethorphan.

In some embodiments, the dextromethorphan $C_{avg}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 9, the $C_{avg}$ can be for 12 hours after the first dose of dextromethorphan.

In some embodiments, the dextromethorphan $C_{avg}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 10, the $C_{avg}$ can be for 12 hours after the first dose of dextromethorphan.

The dextromethorphan fluctuation index values FI (%) can be determined by equation:

$$FI(\%) = \frac{(C_{max} - C_{min})}{C_{avg}} \times 100.$$

In some embodiments, the dextromethorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for eight days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for nine days without plasma level enhancement, such as by co-administration of dextromethorphan with bupropion, hydroxybupropion, threohydroxybupropion, erythrohydroxybupropion, or a metabolite or prodrug of any of these compounds.

In some embodiments, the dextromethorphan FI (%) on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for ten days without plasma level enhancement, such as by co-administration of dextromethorphan with bupropion, hydroxybupropion, threohydroxybupropion, erythrohydroxybupropion, or a metabolite or prodrug of any of these compounds.

In some embodiments, the dextromethorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextrorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for eight days without plasma level enhancement, such as by co-administration of dextromethorphan with bupropion, hydroxybupropion, threohydroxybupropion, erythrohydroxybupropion, or a metabolite or prodrug of any of these compounds.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for nine days without plasma level enhancement, such as by co-administration of dextromethorphan with bupropion, hydroxybupropion, threohydroxybupropion, erythrohydroxybupropion, or a metabolite or prodrug of any of these compounds.

In some embodiments, the dextrorphan FI (%) on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for ten days without plasma level enhancement, such as by co-administration of dextromethorphan with bupropion, hydroxybupropion, threohydroxybupropion, erythrohydroxybupropion, or a metabolite or prodrug of any of these compounds.

In some embodiments, the dextrorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextromethorphan trough level (e.g. plasma level 12 hours after administration; also referred herein as "$C_{min}$") on the first day that bupropion, hydroxybupropion, threohydroxybupropion, erythrohydroxybupropion, or a metabolite or prodrug of any of these compounds, is administered may be at least twice the trough level that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $C_{min}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 0.8 ng/mL, at least about 0.9 ng/mL, at least about 1.0 ng/mL, at least about 1.1 ng/mL, at least about 1.2 ng/mL, at least about 1.3 ng/mL, at least about 1.4 ng/mL, at least about 1.5 ng/mL, at least about 1.6 ng/mL, at least about 1.7 ng/mL, at least about 1.8 ng/mL, at least about 1.9 ng/mL, at least about 2.0 ng/mL, at least about 2.1 ng/mL, at least about 2.2 ng/mL, at least about 2.3 ng/mL, at least about 2.4 ng/mL, at least about 2.5 ng/mL, or at least about 2.5 ng/mL, and may be up to about 100 ng/mL.

In some embodiments, the dextromethorphan $C_{min}$ on the fifth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, or at least about 80.9 ng/mL, and may be up to about 10,000 ng/m L.

In some embodiments, the dextromethorphan $C_{min}$ on the sixth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, or at least about 102.2 ng/mL, and may be up to about 10,000 ng/mL.

In some embodiments, the dextromethorphan $C_{min}$ on the seventh day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, or at least about 110.6 ng/mL, and may be up to about 10,000 ng/mL.

In some embodiments, the dextromethorphan $C_{min}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, the dextromethorphan $C_{min}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, the dextromethorphan $C_{min}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, bupropion, hydroxybupropion, threohydroxybupropion, erythrohydroxybupropion, or a metabolite or prodrug of any of these compounds, is administered on the first day of at least two days of treatment with dextromethorphan, wherein a decrease in the dextrorphan plasma level occurs on the first day that bupropion, hydroxybupropion, threohydroxybupropion, erythrohydroxybupropion, or a metabolite or prodrug of any of these compounds, and dextromethorphan are co-administered, as compared to the same amount of dextromethorphan administered without bupropion, hydroxybupropion, threohydroxybupropion, erythrohydroxybupropion, or a metabolite or prodrug of any of these compounds. For example, the dextrorphan plasma level on the first day may be reduced by at least 5% as compared to the dextrorphan plasma level that would be achieved by administering the same amount of dextromethorphan without bupropion.

In some embodiments, bupropion, hydroxybupropion, threohydroxybupropion, erythrohydroxybupropion, or a metabolite or prodrug of any of these compounds, are co-administered with dextromethorphan for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for five consecutive days. For example, the dextromethorphan plasma level on the fifth day (for example at 0 hours, 1 hour, 3 hours, 6 hours, or 12 hours after administration) may be at least 5 times, at least 10 times, at least 20 times, at least 40 times, at least 50 times, at least 60 times, at least 65 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for five consecutive days.

In some embodiments, bupropion, hydroxybupropion, threohydroxybupropion, erythrohydroxybupropion, or a metabolite or prodrug of any of these compounds, and dextromethorphan, are co-administered for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for six consecutive days. For example, the dextromethorphan plasma level on the sixth day (for example at 0 hours, 1 hour, 3 hours, 6 hours, or 12 hours after administration) may be at least 5 times, at least 10 times, at least 20 times, at least 30 times, at least 50 times, at least 60 times, at least 70 times, at least 75 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for six consecutive days.

In some embodiments, bupropion, hydroxybupropion, threohydroxybupropion, erythrohydroxybupropion, or a metabolite or prodrug of any of these compounds, and dextromethorphan, are co-administered for at least seven consecutive days, to a human being in need of treatment with dextromethorphan, wherein, on the seventh day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for seven consecutive days. For example, the dextromethorphan plasma level on the seventh day (for example at 0 hours, 1 hour, 3 hours, 6 hours, or 12 hours after administration) may be at least 5 times, at least 10 times, at least 20 times, at least 30 times, at least 50 times, at least 70 times, at least 80 times, at least 90 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for seven consecutive days.

In some embodiments, bupropion, hydroxybupropion, threohydroxybupropion, erythrohydroxybupropion, or a metabolite or prodrug of any of these compounds, and dextromethorphan, are co-administered for at least eight consecutive days, wherein, on the eighth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion, hydroxybupropion, threohydroxybupropion, erythrohydroxybupropion, or a metabolite or prodrug of any of these compounds, and dextromethorphan are co-administered for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for eight consecutive days. For example, the dextrorphan plasma level on the eighth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion, hydroxybupropion, threohydroxybupropion, erythrohydroxybupropion, or a metabolite or prodrug of any of these compounds, and dextromethorphan, are co-administered for at least nine consecutive days, wherein, on the ninth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for nine consecutive days.

In some embodiments, bupropion, hydroxybupropion, threohydroxybupropion, erythrohydroxybupropion, or a metabolite or prodrug of any of these compounds, and dextromethorphan are co-administered for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for nine consecutive days. For example, the dextrorphan plasma level on the ninth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for nine consecutive days.

In some embodiments, bupropion, hydroxybupropion, threohydroxybupropion, erythrohydroxybupropion, or a metabolite or prodrug of any of these compounds, and dextromethorphan, are co-administered for at least ten consecutive days, wherein, on the tenth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for ten consecutive days.

In some embodiments, bupropion, hydroxybupropion, threohydroxybupropion, erythrohydroxybupropion, or a metabolite or prodrug of any of these compounds, and dextromethorphan are co-administered for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for ten consecutive days. For example, the dextrorphan plasma level on the tenth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for ten consecutive days.

In some embodiments, bupropion may be administered to a human being in an amount that results in an $AUC_{0-12}$ of bupropion in the human being, on day 8, that is at least about 100 ng·hr/mL, at least about 200 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1,000 ng·hr/mL, at least about 1,200 ng·hr/mL, at least 1,600 ng·hr/mL, or up to about 15,000 ng·hr/mL.

In some embodiments, bupropion may be administered to a human being in an amount that results in a $C_{avg}$ of bupropion in the human being, on day 8, that is at least about 10 ng/mL, at least about 20 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least 120 ng/mL, or up to about 1,500 ng/mL.

In some embodiments, bupropion may be administered to a human being in an amount that results in a $C_{max}$ of bupropion in the human being, on day 8, that is at least about 10 ng/mL, at least about 20 ng/mL, at least about 50 ng/mL, at least about 90 ng/mL, at least about 100 ng/mL, at least about 110 ng/mL, at least about 120 ng/mL, at least about 130 ng/mL, at least about 140 ng/mL, at least 200 ng/mL, or up to about 1,500 ng/mL.

Some liquid compositions may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of bupropion, or any amount of bupropion in a range bounded by, or between, any of these values.

Some liquid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 100 mg to about 110 mg, about 105 mg to about 200 mg, about 110 mg to about 140 mg, about 180 mg to about 220 mg, about 280 mg to about 320 mg, about 105 mg, about 200 mg, about 150 mg, or about 300 mg of bupropion, e.g. bupropion chloride, or any amount of bupropion in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of bupropion, or any amount of bupropion in a range bounded by, or between, any of these values.

Some solid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 100 mg to about 120 mg, about 105 mg to about 200 mg, about 90 mg to about 120 mg, about 100 mg to about 110 mg, about 110 mg to about 140 mg, about 50 mg to about 150 mg, about 180 mg to about 220 mg, about 280 mg to about 320 mg, about 105 mg, about 200 mg, about 150 mg, or about 300 mg of bupropion, e.g. bupropion chloride, or any amount of bupropion in a range bounded by, or between, any of these values.

In some embodiments, bupropion is administered at a dose that results in a bupropion plasma level of about 0.1 µM to about 10 µM, about 0.1 µM to about 5 µM, about 0.2 µM to about 3 µM, about 0.1 µM to about 1 µM, about 0.2 µM to about 2 µM, about 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, hydroxybupropion, or a prodrug of hydroxybupropion, is administered at a dose that results in a hydroxybupropion plasma level of about 0.1 µM to about 10 µM, about 0.1 µM to about 5 µM, about 0.2 µM to about 3 µM, about 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, hydroxybupropion, or a prodrug of hydroxybupropion, may be administered to a human being in an amount that results in an $AUC_{0-12}$ of hydroxybupropion in the human being, on day 8, that is at least about 3,000 ng·hr/mL, at least about 7,000 ng·hr/mL, at least about 10,000 ng·hr/mL, at least about 15,000 ng·hr/mL, at least about 20,000 ng·hr/mL, at least about 30,000 ng·hr/mL, up to about 50,000 ng·hr/mL, up to about 150,000 ng·hr/mL, or any AUC in a range bounded by, or between, any of these values.

In some embodiments, bupropion, hydroxybupropion, or a prodrug of hydroxybupropion, may be administered to a human being in an amount that results in a $C_{max}$ of hydroxybupropion in the human being, on day 8, that is at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{max}$ in a range bounded by, or between, any of these values.

In some embodiments, bupropion, hydroxybupropion, or a prodrug of hydroxybupropion, may be administered to a human being in an amount that results in a $C_{avg}$ of hydroxybupropion in the human being, on day 8, that is at least about 200 ng/mL, at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{avg}$ in a range bounded by, or between, any of these values.

In some embodiments, bupropion, threohydroxybupropion, or a prodrug of threohydroxybupropion, is administered at a dose that results in a threohydroxybupropion plasma level of about 0.1 µM to about 10 µM, about 0.1 µM to about 5 µM, about 0.2 µM to about 3 µM, about 0.1 µM to about 1 µM, about 0.2 µM to about 2 µM, about 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, threohydroxybupropion, or a prodrug of threohydroxybupropion, may be administered to a human being in an amount that results in an $AUC_{0-12}$ of threohydroxybupropion in the human being, on day 8, that is at least about 1,000 ng·hr/mL, at least about 2,000 ng·hr/mL, at least about 4,000 ng·hr/mL, at least about 5,000 ng·hr/mL, at least about 8,000 ng·hr/mL, up to about 10,000 ng·hr/mL, up to about 40,000 ng·hr/mL, or any AUC in a range bounded by, or between, any of these values.

In some embodiments, bupropion, threohydroxybupropion, or a prodrug of threohydroxybupropion, may be administered to a human being in an amount that results in a $C_{max}$ of threohydroxybupropion in the human being, on day 8, that is at least about 100 ng/mL, at least about 200 ng/mL, at least about 400 ng/mL, at least about 500 ng/mL, at least about 600 ng/mL, at least about 800 ng/mL, up to about 2,000 ng/mL, up to about 10,000 ng/mL, or any $C_{max}$ in a range bounded by, or between, any of these values.

In some embodiments, bupropion, threohydroxybupropion, or a prodrug of threohydroxybupropion, may be administered to a human being in an amount that results in a $C_{avg}$ of threohydroxybupropion in the human being, on day 8, that is at least about 100 ng/mL, at least about 300 ng/mL, at least about 400 ng/mL, at least about 600 ng/mL, at least about 800 ng/mL, up to about 2,000 ng/mL, up to about 10,000 ng/mL, or any $C_{avg}$ in a range bounded by, or between, any of these values.

In some embodiments, bupropion, erythrohydroxybupropion, or a prodrug of erythrohydroxybupropion, is administered at a dose that results in an erythrohydroxybupropion plasma level of about 0.1 µM to about 10 µM, about 0.1 µM to about 5 µM, about 0.2 µM to about 3 µM, about 0.1 µM to about 1 µM, about 0.2 µM to about 2 µM, about 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, erythrohydroxybupropion, or a prodrug of erythrohydroxybupropion, may be administered to a human being in an amount that results in an $AUC_{0-12}$ of erythrohydroxybupropion in the human being, on day 8, that is at least about 200 ng·hr/mL, at least about 400 ng·hr/mL, at least about 700 ng·hr/mL, at least about 1,000 ng·hr/mL, at least about 1,500 ng·hr/mL, at least about 3,000 ng·hr/mL, up to about 5,000 ng·hr/mL, up to about 30,000 ng·hr/mL, or any plasma level in a range bounded by, or between, any of these values.

In some embodiments, bupropion, erythrohydroxybupropion, or a prodrug of erythrohydroxybupropion, may be administered to a human being in an amount that results in a $C_{max}$ of erythrohydroxybupropion in the human being, on day 8, that is at least about 30 ng/mL, at least about 60 ng/mL, at least about 90 ng/mL, at least about 100 ng/mL, at least about 150 ng/mL, at least about 200 ng/mL, at least about 300 ng/mL, up to about 1,000 ng/mL, or any $C_{max}$ in a range bounded by, or between, any of these values.

In some embodiments, bupropion, erythrohydroxybupropion, or a prodrug of erythrohydroxybupropion, may be administered to a human being in an amount that results in a $C_{avg}$ of erythrohydroxybupropion in the human being, on day 8, that is at least about 20 ng/mL, at least about 30 ng/mL, at least about 50 ng/mL, at least about 80 ng/mL, at least about 90 ng/mL, at least about 100 ng/mL, at least about 150 ng/mL, at least about 200 ng/mL, at least about 300 ng/mL, up to about 1,000 ng/mL, up to about 5,000 ng/mL, or any $C_{avg}$ in a range bounded by, or between, any of these values.

For compositions comprising both dextromethorphan and bupropion, some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), about 40% (w/v) to about 50% (w/v) of dextromethorphan and bupropion combined, or any amount in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), about 80% (w/w) to about 90% (w/w) of dextromethorphan and bupropion combined, or any amount in a range bounded by, or between, any of these values.

In some embodiments, the weight ratio of dextromethorphan to bupropion in a single composition or dosage form may be about 0.1 to about 2, about 0.2 to about 1, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values.

A therapeutically effective amount of a therapeutic compound may vary depending upon the circumstances. For example, a daily dose of dextromethorphan may in some instances range from about 0.1 mg to about 1000 mg, about 40 mg to about 1000 mg, about 20 mg to about 600 mg, about 60 mg to about 700 mg, about 100 mg to about 400 mg, about 15 mg to about 20 mg, about 20 mg to about 25 mg, about 25 mg to about 30 mg, about 30 mg to about 35 mg, about 35 mg to about 40 mg, about 40 mg to about 45 mg, about 45 mg to about 50 mg, about 50 mg to about 55 mg, about 55 mg to about 60 mg, about 20 mg to about 60 mg, about 60 mg to about 100 mg, about 100 mg to about 200 mg, about 100 mg to about 140 mg, about 160 mg to about 200 mg, about 200 mg to about 300 mg, about 220 mg to about 260 mg, about 300 mg to about 400 mg, about 340 mg to about 380 mg, about 400 mg to about 500 mg, about 500 mg to about 600 mg, about 15 mg, about 30 mg, about 60 mg, about 120 mg, about 180 mg, about 240 mg, about 360 mg, or any daily dose in a range bounded by, or between, any of these values. Dextromethorphan may be administered once daily; or twice daily or every 12 hours, three times daily, four times daily, or six times daily in an amount that is about half, one third, one quarter, or one sixth, respectively, of the daily dose.

A daily dose of bupropion, may in some instances range from about 10 mg to about 1000 mg, about 50 mg to about 600 mg, about 100 mg to about 2000 mg, about 50 mg to about 100 mg, about 70 mg to about 95 mg, about 100 mg to about 200 mg, about 105 mg to about 200 mg, about 100 mg to about 150 mg, about 150 mg to about 300 mg, about 150 mg to about 200 mg, about 200 mg to about 250 mg, about 250 mg to about 300 mg, about 200 mg about 300 mg, about 300 mg to about 400 mg, about 400 mg to about 500 mg, about 400 mg to about 600 mg, about 360 mg to about 440 mg, about 560 mg to about 640 mg, or about 500 mg to about 600 mg, about 100 mg, about 150 mg, about 200 mg, about 300 mg, about 400 mg, about 600 mg, or any daily dose in a range bounded by, or between, any of these values. Bupropion may be administered once daily; or twice daily or every 12 hours, or three times daily in an amount that is about half or one third, respectively, of the daily dose.

In some embodiments: 1) about 50 mg/day to about 100 mg/day, about 100 mg/day to about 150 mg/day, about 150 mg/day to about 300 mg/day, about 150 mg/day to about 200 mg/day, about 200 mg/day to about 250 mg/day, about 250 mg/day to about 300 mg/day of bupropion, or about 300 mg/day to about 500 mg/day of bupropion; and/or 2) about 15 mg/day to about 60 mg/day, about 15 mg/day to about 30 mg/day, about 30 mg/day to about 45 mg/day, about 45 mg/day to about 60 mg/day, about 60 mg/day to about 100 mg/day, about 80 mg/day to about 110 mg/day, about 100 mg/day to about 150 mg/day, or about 100 mg/day to about 300 mg/day of dextromethorphan, are administered to a human being in need thereof.

In some embodiments, about 150 mg/day of bupropion and about 30 mg/day of dextromethorphan, about 150 mg/day of bupropion and about 60 mg/day of dextromethorphan, about 150 mg/day of bupropion and about 90 mg/day of dextromethorphan, about 150 mg/day of bupropion and about 120 mg/day of dextromethorphan, about 200 mg/day of bupropion and about 30 mg/day of dextromethorphan, about 200 mg/day of bupropion and about 60 mg/day of dextromethorphan, about 200 mg/day of bupropion and about 90 mg/day of dextromethorphan, about 200 mg/day of bupropion and about 120 mg/day of dextromethorphan, about 300 mg/day of bupropion and about 30 mg/day of dextromethorphan, about 300 mg/day of bupropion and about 60 mg/day of dextromethorphan, about 300 mg/day of bupropion and about 90 mg/day of dextromethorphan, or about 300 mg/day of bupropion and about 120 mg/day of dextromethorphan is administered to the human being.

In some embodiments, about 100 mg/day of bupropion and about 15 mg/day of dextromethorphan is administered to the human being for 1, 2, or 3 days, followed by about 200 mg/day of bupropion and about 30 mg/day of dextromethorphan. In some embodiments, about 100 mg/day of bupropion and about 30 mg/day of dextromethorphan is administered to the human being for 1, 2, or 3 days, followed by about 200 mg/day of bupropion and about 60 mg/day of dextromethorphan.

In some embodiments, about 75 mg/day of bupropion and about 15 mg/day of dextromethorphan is administered to the human being for 1, 2, or 3 days, followed by about 150 mg/day of bupropion and about 30 mg/day of dextromethorphan. In some embodiments, about 75 mg/day of bupropion and about 30 mg/day of dextromethorphan is administered to the human being for 1, 2, or 3 days, followed by about 150 mg/day of bupropion and about 60 mg/day of dextromethorphan.

An antidepressant compound, such as bupropion, may be administered for as long as needed to treat a neurological condition, such as pain, depression, or cough. In some embodiments, an antidepressant compound, such as bupropion, and dextromethorphan are administered at least once a day, such as once daily or twice daily, for at least 1 day, at least 3 days, at least 5 days, at least 7 days, at least 8 days, at least 9 days, or at least 10 days, at least 14 days, at least 21 days, at least 28 days, at least 30 days, at least 35 days, at least 42 days, at least 60 days, at least 90 days, at least 180 days, at least 365 days, or longer.

In some embodiments, co-administration of dextromethorphan with bupropion, hydroxybupropion, erythrohydroxybupropion, threohydroxybupropion, or a prodrug of any of these compounds, may occur once a day for about 1, 2, 3, 4, 5, 6, 7, 8, 9, 10, 11, 12, 13, 14, 15, or more days prior to co-administering dextromethorphan with bupropion, hydroxybupropion, erythrohydroxybupropion, threohydroxybupropion, or a prodrug of any of these compounds twice a day.

Therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

Tablets, troches, pills, capsules, and the like may also contain one or more of the following: a binder such as gum tragacanth, acacia, corn starch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as a coating, for example, tablets, pills, or capsules may be coated with shellac, sugar, or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially nontoxic in the amounts employed.

Some compositions or dosage forms may be a liquid or may comprise a solid phase dispersed in a liquid.

Therapeutic compounds may be formulated for parental or intraperitoneal administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

In some embodiments, the human being or the patient is, or is selected for being, Black or African American.

In some embodiments, the human being or the patient is, or is selected for being, white.

In some embodiments, the human being or the patient is, or is selected for being, Asian.

In some embodiments, the human being or the patient is, or is selected for being, Native Hawaiian or other Pacific Islander.

In some embodiments, the human being or the patient is, or is selected for being, Hispanic or Latino.

In some embodiments, the human being or the patient is, or is selected for being, Native American or Alaska Native.

In some embodiments, the human being or the patient is not, or is selected for not being, Hispanic or Latino.

Specifically Contemplated Embodiments

The following are examples of embodiments that are specifically contemplated by the inventor:

Embodiment 1. A method of treating pain or a neurological disorder comprising delivering an enhanced plasma level or bioavailability of dextromethorphan or administering a therapeutically effective amount of a combination of dextromethorphan and an antidepressant compound, to a person in need thereof.

Embodiment 2. A method of treating pain comprising administering a combination of an antidepressant compound and dextromethorphan to a human being in need thereof.

Embodiment 3. A method of enhancing the pain relieving properties of dextromethorphan, comprising co-administering dextromethorphan and an antidepressant compound.

Embodiment 4. A method of increasing dextromethorphan plasma levels in a human being that is an extensive metabolizer of dextromethorphan, comprising co-administering an antidepressant compound to the human being receiving a treatment that includes administration of dextromethorphan.

Embodiment 5. A method of inhibiting the metabolism of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 6. A method of increasing the metabolic lifetime of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 7. A method of correcting extensive metabolism of dextromethorphan, comprising administering an antidepressant compound to a human being in need thereof.

Embodiment 8. A method of improving pain relieving properties of dextromethorphan comprising administering an antidepressant compound in conjunction with administration of dextromethorphan to a human being in need of treatment for pain.

Embodiment 9. A method of improving antitussive properties of dextromethorphan comprising administering an antidepressant compound in conjunction with administration of dextromethorphan to a human being in need of treatment for cough.

Embodiment 10. A method of treating cough comprising administering a combination of an antidepressant compound and dextromethorphan to a human being in need thereof.

Embodiment 11. A method of improving a therapeutic property of dextromethorphan comprising administering an antidepressant compound in conjunction with administration of dextromethorphan to a human being in need of treatment for a neurological disorder.

Embodiment 12. A method of treating a neurological disorder comprising administering a combination of an antidepressant compound and dextromethorphan to a human being in need thereof.

Embodiment 13. A method of treating a neurological disorder comprising administering an antidepressant compound and dextromethorphan to a human being in need thereof, wherein the human being is an extensive metabolizer of dextromethorphan.

Embodiment 14. The method of any preceding embodiment, such as embodiment 1, 2, 3, 4, 5, 6, 7, 8, 9, 10, 11, 12, or 13, wherein the dextromethorphan and the antidepressant compound are administered in separate dosage forms.

Embodiment 15. A pharmaceutical composition comprising a therapeutically effective amount of dextromethorphan, a therapeutically effective amount of an antidepressant compound, and a pharmaceutically acceptable excipient.

Embodiment 16. An oral dosage form comprising at least 20 mg of dextromethorphan and an effective amount of an antidepressant compound to inhibit the metabolism of dextromethorphan in a human being that is an extensive metabolizer of dextromethorphan.

Embodiment 17. The oral dosage form of embodiment 16, wherein about 30 mg to about 350 mg of dextromethorphan is present in the dosage form.

Embodiment 18. The oral dosage form of embodiment 16 or 17, wherein about 100 mg to about 400 mg of bupropion is present in the dosage form.

Embodiment 19. The oral dosage form of any of embodiments 16, 17, or 18, comprising an amount of bupropion that results in a bupropion plasma level of about 0.1 µM to about 10 µM when the oral dosage form is administered to a human being.

Embodiment 20. The oral dosage form of embodiment 19, comprising an amount of bupropion that results in a bupropion plasma level of about 0.1 µM to about 2 µM when the oral dosage form is administered to a human being.

Embodiment 21. The method of any preceding embodiment, such as embodiment 1, 2, 3, 4, 5, 6, 7, 8, 9, 10, 11, 12, or 13, wherein bupropion is administered at a dose that results in a bupropion plasma level of about 0.1 µM to about 10 µM.

Embodiment 22. The method of any preceding embodiment, such as embodiment 21, wherein bupropion is administered at a dose that results in a bupropion plasma level of about 0.3 µM to about 1 µM.

Embodiment 23. The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is bupropion or a metabolite thereof.

Embodiment 24. The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is bupropion.

Embodiment 25. The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, ketamine, or a pharmaceutically acceptable salt thereof Embodiment 26. The method of any preceding embodiment, such as embodiment 1, 2, 3, 4, 5, 6, 7, 8, 11, 12, 13, 14, 21, 22, 23, 24, or 25, wherein dextromethorphan is administered to the human being for the treatment of cough.

Embodiment 27. A method of treating a neurological disorder comprising administering about 150 mg/day to about 300 mg/day of bupropion and about 30 mg/day to about 120 mg/day of dextromethorphan to a human being in need thereof.

Embodiment 28. A method of treating a neurological disorder comprising administering bupropion and dextromethorphan to a human being in need thereof, wherein the bupropion and dextromethorphan are administered at least once a day for at least 8 days, at least 9 days, or at least 10 days.

Embodiment 29. The method of any preceding embodiment, such as embodiment 1, 2, 3, 4, 5, 6, 7, 8, 9, 10, 11, 12, 13, 14, 21, 22, 23, 24, 25, 26, or 27, wherein bupropion is administered to the human being at least daily for at least 8 days, at least 9 days, or at least 10 days.

Embodiment 30. The method of any preceding embodiment, such as embodiment 1, 2, 3, 4, 5, 6, 7, 8, 9, 10, 11, 12, 13, 14, 21, 22, 23, 24, 25, 26, 27, or 28, wherein dextromethorphan is administered to the human being at least daily for at least 8 days, at least 9 days, or at least 10 days.

Embodiment 31. The method of any preceding embodiment, such as embodiment 28, 29, or 30, wherein bupropion is administered in an amount that results in a plasma concentration of dextromethorphan in the human being, on day 8, that is at least 10 times the plasma concentration of the same amount of dextromethorphan administered without bupropion.

Embodiment 32. The method of any preceding embodiment, such as embodiment 28, 29, 30, or 31, wherein bupropion is administered in an amount that results in an $AUC_{0-12}$ of hydroxybupropion, on day 8, that is at least about 3000 ng·hr/mL.

Embodiment 33. The method of any preceding embodiment, such as embodiment 28, 29, 30, 31, or 32, wherein bupropion is administered in an amount that results in an $AUC_{0-12}$ of erythrohydroxybupropion, on day 8, that is at least about 400 ng·hr/mL.

Embodiment 34. The method of any preceding embodiment, such as embodiment 28, 29, 30, 31, 32, or 33, wherein bupropion is administered in an amount that results in an $AUC_{0-12}$ of threohydroxybupropion, on day 8, that is at least about 2000 ng·hr/mL.

Embodiment 35. The method, composition, or dosage form of any preceding embodiment, such as embodiment 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, or 34, wherein the weight ratio of dextromethorphan to bupropion is about 0.1 to about 0.5.

Embodiment 36. The method of any preceding embodiment, such as embodiment 27, 28, 29, 30, 31, 32, 33, 34, or 35, wherein the human being is an extensive metabolizer of dextromethorphan.

Embodiment 37. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 30 mg/day of dextromethorphan is administered to the human being.

Embodiment 38. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 60 mg/day of dextromethorphan is administered to the human being.

Embodiment 39. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 30 mg/day of dextromethorphan is administered to the human being.

Embodiment 40. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 15 mg/day of dextromethorphan is administered to the human being for about 1 to about 3 days, followed by about 200 mg/day of bupropion and about 30 mg/day of dextromethorphan.

Embodiment 41. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 60 mg/day of dextromethorphan is administered to the human being.

Embodiment 42. The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 30 mg/day of dextromethorphan is administered to the human being for about 1 to about 3 days, followed by about 200 mg/day of bupropion and about 60 mg/day of dextromethorphan.

Embodiment 43. The method of any preceding embodiment, such as embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, or 42, wherein dextromethorphan is administered to the human being for the treatment of pain.

Embodiment 44. The method of any preceding embodiment, such as embodiment 43, wherein the pain comprises postoperative pain, cancer pain, arthritic pain, lumbosacral pain, musculoskeletal pain, central multiple sclerosis pain, nociceptive pain, or neuropathic pain.

Embodiment 45. The method of any preceding embodiment, such as embodiment 43, wherein the pain comprises musculoskeletal pain, neuropathic pain, cancer-related pain, acute pain, or nociceptive pain.

Embodiment 46. The method of any preceding embodiment, such as embodiment 43, wherein the pain comprises postoperative pain.

Embodiment 47. The method of any preceding embodiment, such as embodiment 43, wherein the pain comprises cancer pain.

Embodiment 48. The method of any preceding embodiment, such as embodiment 43, wherein the pain comprises arthritic pain.

Embodiment 49. The method of any preceding embodiment, such as embodiment 43, wherein the pain comprises lumbosacral pain.

Embodiment 50. The method of any preceding embodiment, such as embodiment 43, wherein the pain comprises musculoskeletal pain.

Embodiment 51. The method of any preceding embodiment, such as embodiment 43, wherein the pain comprises neuropathic pain.

Embodiment 52. The method of any preceding embodiment, such as embodiment 43, wherein the pain comprises nociceptive pain.

Embodiment 53. The method of any preceding embodiment, such as embodiment 43, wherein the pain comprises chronic musculoskeletal pain.

Embodiment 54. The method of any preceding embodiment, such as embodiment 43, wherein the pain is associated with rheumatoid arthritis.

Embodiment 55. The method of any preceding embodiment, such as embodiment 43, wherein the pain is associated with juvenile rheumatoid arthritis.

Embodiment 56. The method of any preceding embodiment, such as embodiment 43, wherein the pain is associated with osteoarthritis.

Embodiment 57. The method of any preceding embodiment, such as embodiment 43, wherein the pain is associated with an axial spondyloarthritis.

Embodiment 58. The method of any preceding embodiment, such as embodiment 43, wherein the pain is associated with ankylosing spondylitis.

Embodiment 59. The method of any preceding embodiment, such as embodiment 43, wherein the pain is associated with diabetic peripheral neuropathy.

Embodiment 60. The method of any preceding embodiment, such as embodiment 43, wherein the pain is associated with post-herpetic neuralgia.

Embodiment 61. The method of any preceding embodiment, such as embodiment 43, wherein the pain is associated with trigeminal neuralgia.

Embodiment 62. The method of any preceding embodiment, such as embodiment 43, wherein the pain is associated with monoradiculopathies.

Embodiment 63. The method of any preceding embodiment, such as embodiment 43, wherein the pain is associated with phantom limb pain.

Embodiment 64. The method of any preceding embodiment, such as embodiment 43, wherein the pain is associated with central pain.

Embodiment 65. The method of any preceding embodiment, such as embodiment 43, wherein the pain comprises cancer-related pain.

Embodiment 66. The method of any preceding embodiment, such as embodiment 43, wherein the pain is associated with lumbar nerve root compression.

Embodiment 67. The method of any preceding embodiment, such as embodiment 43, wherein the pain is associated with spinal cord injury.

Embodiment 68. The method of any preceding embodiment, such as embodiment 43, wherein the pain is associated with post-stroke pain.

Embodiment 69. The method of any preceding embodiment, such as embodiment 43, wherein the pain is associated with central multiple sclerosis pain.

Embodiment 70. The method of any preceding embodiment, such as embodiment 43, wherein the pain is associated with HIV-associated neuropathy.

Embodiment 71. The method of any preceding embodiment, such as embodiment 43, wherein the pain is associated with radio-therapy associated neuropathy.

Embodiment 72. The method of any preceding embodiment, such as embodiment 43, wherein the pain is associated with chemo-therapy associated neuropathy.

Embodiment 73. The method of any preceding embodiment, such as embodiment 43, wherein the pain comprises dental pain.

Embodiment 74. The method of any preceding embodiment, such as embodiment 43, wherein the pain is associated with primary dysmenorrhea.

Embodiment 75. The method of any preceding embodiment, such as embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, wherein 90 mg/day of dextromethorphan is administered to the human being.

Embodiment 76. The method of any preceding embodiment, such as embodiment 75, wherein 45 mg of dextromethorphan is administered twice a day to the human being.

Embodiment 77. The method of any preceding embodiment, such as embodiment 75 or 76, wherein 150 mg/day of bupropion is administered to the human being.

Embodiment 78. The method of any preceding embodiment, such as embodiment 75 or 76, wherein 180 mg/day of bupropion is administered to the human being.

Embodiment 79. The method of any preceding embodiment, such as embodiment 75 or 76, wherein 200 mg/day of bupropion is administered to the human being.

Embodiment 80. The method of any preceding embodiment, such as embodiment 75 or 76, wherein 300 mg/day of bupropion is administered to the human being.

Embodiment 81. A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in an $AUC_{0-12}$ of dextromethorphan that is at least about 40 ng·hr/mL.

Embodiment 82. The method of any preceding embodiment, such as embodiment 81, wherein the $AUC_{0-12}$ of dextromethorphan is at least about 50 ng·hr/mL.

Embodiment 83. The method of any preceding embodiment, such as embodiment 81 or 82, wherein the human being is in need of treatment with dextromethorphan.

Embodiment 84. The method of any preceding embodiment, such as embodiment 81, 82, or 83, wherein the human being is an extensive metabolizer of dextromethorphan.

Embodiment 85. The method of any preceding embodiment, such as embodiment 81, 82, 83, or 84, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 86. The method of any preceding embodiment, such as embodiment 85, wherein the $AUC_{0-12}$ of dextromethorphan on Day 8, Day 9, or Day 10 is at least about 100 ng·hr/mL.

Embodiment 87. The method of any preceding embodiment, such as embodiment 85 or 86, wherein the $AUC_{0-12}$ of dextromethorphan on Day 8, Day 9, or Day 10 is at least about 400 ng·hr/mL.

Embodiment 88. The method of any preceding embodiment, such as embodiment 85, 86, or 87, wherein the $AUC_{0-12}$ of dextromethorphan on Day 8, Day 9, or Day 10 is at least about 800 ng·hr/mL.

Embodiment 89. The method of any preceding embodiment, such as embodiment 85, 86, 87, or 88, wherein the $AUC_{0-12}$ of dextromethorphan on Day 8, Day 9, or Day 10 is at least about 1500 ng·hr/mL.

Embodiment 90. The method of any preceding embodiment, such as embodiment 85, 86, 87, 88, or 89, wherein the $AUC_{0-24}$ of dextromethorphan on Day 8, Day 9, or Day 10 is at least about 100 ng·hr/mL.

Embodiment 91. The method of any preceding embodiment, such as embodiment 85, 86, 87, 88, 89, or 90, wherein the $AUC_{0-24}$ of dextromethorphan on Day 8, Day 9, or Day 10 is at least about 1500 ng·hr/mL.

Embodiment 92. The method of any preceding embodiment, such as embodiment 85, 86, 87, 88, 89, 90, or 91, wherein the $AUC_{0-24}$ of dextromethorphan on Day 8, Day 9, or Day 10 is at least about 2900 ng·hr/mL.

Embodiment 93. The method of any preceding embodiment, such as embodiment 85, 86, 87, 88, 89, 90, 91, or 92, wherein the $AUC_{0-inf}$ of dextromethorphan on Day 8, Day 9, or Day 10 is at least about 100 ng·hr/mL.

Embodiment 94. The method of any preceding embodiment, such as embodiment 85, 86, 87, 88, 89, 90, 91, 92, or 93, wherein the $AUC_{0-inf}$ of dextromethorphan on Day 8, Day 9, or Day 10 is at least about 1500 ng·hr/mL.

Embodiment 95. The method of any preceding embodiment, such as embodiment 85, 86, 87, 88, 89, 90, 91, 92, 93, or 94, wherein the $AUC_{0-inf}$ of dextromethorphan on Day 8, Day 9, or Day 10 is at least about 3500 ng·hr/mL.

Embodiment 96. The method of any preceding embodiment, such as embodiment 85, 86, 87, 88, 89, 90, 91, 92, 93, 94, or 95, wherein the $AUC_{0-inf}$ of dextromethorphan on Day 8, Day 9, or Day 10 is at least about 5000 ng·hr/mL.

Embodiment 97. A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in a $C_{max}$ of dextromethorphan that is at least about 6 ng/mL.

Embodiment 98. The method of any preceding embodiment, such as embodiment 97, wherein the human being is in need of treatment with dextromethorphan.

Embodiment 99. The method of any preceding embodiment, such as embodiment 97 or 98, wherein the human being is an extensive metabolizer of dextromethorphan.

Embodiment 100. The method of any preceding embodiment, such as embodiment 97, 98, or 99, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 101. The method of any preceding embodiment, such as embodiment 100, wherein the $C_{max}$ of dextromethorphan on Day 8, Day 9, or Day 10 is at least about 20 ng/mL.

Embodiment 102. The method of any preceding embodiment, such as embodiment 100 or 101, wherein the $C_{max}$ of dextromethorphan on Day 8, Day 9, or Day 10 is at least about 60 ng/mL.

Embodiment 103. The method of any preceding embodiment, such as embodiment 100, 101, or 102, wherein the $C_{max}$ of dextromethorphan on Day 8, Day 9, or Day 10 is at least about 120 ng/mL.

Embodiment 104. A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in a $C_{avg}$ of dextromethorphan over a 12 hour period, after one administration, that is at least about 5 ng/mL.

Embodiment 105. The method of any preceding embodiment, such as embodiment 104, wherein the human being is in need of treatment with dextromethorphan.

Embodiment 106. The method of any preceding embodiment, such as embodiment 104 or 105, wherein the human being is an extensive metabolizer of dextromethorphan.

Embodiment 107. The method of any preceding embodiment, such as embodiment 104, 105, or 106, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 108. The method of any preceding embodiment, such as embodiment 107, wherein the $C_{avg}$ of dextromethorphan on Day 8, Day 9, or Day 10 is at least about 20 ng/mL.

Embodiment 109. The method of any preceding embodiment, such as embodiment 107 or 108, wherein the $C_{avg}$ of dextromethorphan on Day 8, Day 9, or Day 10 is at least about 70 ng/mL.

Embodiment 110. The method of any preceding embodiment, such as embodiment 107, 108, or 109, wherein the $C_{avg}$ of dextromethorphan on Day 8, Day 9, or Day 10 is at least about 120 ng/mL.

Embodiment 111. A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in an $AUC_{0-12}$ of dextromethorphan that is at least about 40 ng·hr/mL.

Embodiment 112. The method of any preceding embodiment, such as embodiment 111, wherein the $AUC_{0-12}$ of dextromethorphan is at least about 50 ng·hr/mL.

Embodiment 113. The method of any preceding embodiment, such as embodiment 111 or 112, wherein the human being is in need of treatment with dextromethorphan.

Embodiment 114. The method of any preceding embodiment, such as embodiment 111, 112, or 113, wherein the human being is an extensive metabolizer of dextromethorphan.

Embodiment 115. The method of any preceding embodiment, such as embodiment 111, 112, 113, or 114, wherein the bupropion or a prodrug thereof is co-administered with dextromethorphan at least daily for at least two consecutive days.

Embodiment 116. The method of any preceding embodiment, such as embodiment 115, wherein the bupropion or a prodrug thereof and dextromethorphan are administered to the human being at least daily for at least 8 days, at least 9 days, or at least 10 days.

Embodiment 117. The method of any preceding embodiment, such as embodiment 116, wherein the $AUC_{0-12}$ of dextromethorphan on Day 8, Day 9, or Day 10 is at least about 100 ng·hr/mL.

Embodiment 118. The method of any preceding embodiment, such as embodiment 116, wherein the $AUC_{0-12}$ of dextromethorphan on Day 8, Day 9, or Day 10 is at least about 800 ng·hr/mL.

Embodiment 119. The method of any preceding embodiment, such as embodiment 116, wherein the $AUC_{0-12}$ of dextromethorphan on Day 8, Day 9, or Day 10 is at least about 1500 ng·hr/mL.

Embodiment 120. The method of any preceding embodiment, such as embodiment 116, wherein the $AUC_{0-24}$ of dextromethorphan on Day 8, Day 9, or Day 10 is at least about 100 ng·hr/mL.

Embodiment 121. The method of any preceding embodiment, such as embodiment 116, wherein the $AUC_{0-24}$ of dextromethorphan on Day 8, Day 9, or Day 10 is at least about 1500 ng·hr/mL.

Embodiment 122. The method of any preceding embodiment, such as embodiment 116, wherein the $AUC_{0-inf}$ of dextromethorphan on Day 8, Day 9, or Day 10 is at least about 100 ng·hr/mL.

Embodiment 123. The method of any preceding embodiment, such as embodiment 116, wherein the $AUC_{0-inf}$ of dextromethorphan on Day 8, Day 9, or Day 10 is at least about 3500 ng·hr/mL.

Embodiment 124. The method of any preceding embodiment, such as embodiment 116, wherein the $AUC_{0-inf}$ of dextromethorphan on Day 8, Day 9, or Day 10 is at least about 5000 ng·hr/mL.

Embodiment 125. A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in a $C_{max}$ of dextromethorphan that is at least about 6 ng/mL.

Embodiment 126. The method of any preceding embodiment, such as embodiment 125, wherein the human being is in need of treatment with dextromethorphan.

Embodiment 127. The method of any preceding embodiment, such as embodiment 125 or 126, wherein the human being is an extensive metabolizer of dextromethorphan.

Embodiment 128. The method of any preceding embodiment, such as embodiment 126, 127, or 128, wherein the bupropion or a prodrug thereof is co-administered with dextromethorphan at least daily for at least two consecutive days.

Embodiment 129. The method of any preceding embodiment, such as embodiment 128, wherein the bupropion or a prodrug thereof and dextromethorphan are administered to the human being at least daily for at least 8 days, at least 9 days, or at least 10 days.

Embodiment 130. The method of any preceding embodiment, such as embodiment 129, wherein the $C_{max}$ of dextromethorphan on Day 8, Day 9, or Day 10 is at least about 10 ng/mL.

Embodiment 131. The method of any preceding embodiment, such as embodiment 129, wherein the $C_{max}$ of dextromethorphan on Day 8, Day 9, or Day 10 is at least about 60 ng/mL.

Embodiment 132. The method of any preceding embodiment, such as embodiment 129, wherein the $C_{max}$ of dextromethorphan on Day 8, Day 9, or Day 10 is at least about 120 ng/mL.

Embodiment 133. A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in a $C_{avg}$ of dextromethorphan, over the period between two separate and consecutive administrations of dextromethorphan, that is at least about 5 ng/mL.

Embodiment 134. The method of any preceding embodiment, such as embodiment 134, wherein the bupropion or a prodrug thereof is administered in an amount that results in a $C_{avg}$ of dextromethorphan, over the period between two separate and consecutive administrations of dextromethorphan, that is at least about 60 ng/mL.

Embodiment 135. The method of any preceding embodiment, such as embodiment 134, wherein the human being is in need of treatment with dextromethorphan.

Embodiment 136. The method of any preceding embodiment, such as embodiment 134 or 135, wherein the human being is an extensive metabolizer of dextromethorphan.

Embodiment 137. The method of any preceding embodiment, such as embodiment 134, 135, or 136, wherein the bupropion or a prodrug thereof is co-administered with dextromethorphan at least daily for at least two consecutive days.

Embodiment 138. The method of any preceding embodiment, such as embodiment 137, wherein the bupropion or a prodrug thereof and dextromethorphan are administered to the human being at least daily for at least 8 days, at least 9 days, or at least 10 days.

Embodiment 139. The method of any preceding embodiment, such as embodiment 138, wherein the $C_{avg}$ of dextromethorphan on Day 8, Day 9, or Day 10 is at least about 8 ng/mL, wherein the $C_{avg}$ is for the period between two separate and consecutive administrations of dextromethorphan, or if dextromethorphan is administered only once on Day 8, Day 9, or Day 10, the $C_{avg}$ is for 12 hours after the first dose of dextromethorphan on Day 8, Day 9, or Day 10.

Embodiment 140. The method of any preceding embodiment, such as embodiment 138, wherein the Cavg of dextromethorphan on Day 8, Day 9, or Day 10 is at least about 120 ng/mL, wherein the $C_{avg}$ is for the period between two separate and consecutive administrations of dextromethorphan, or if dextromethorphan is administered only once on Day 8, Day 9, or Day 10, the $C_{avg}$ for 12 hours after the first dose of dextromethorphan on Day 8, Day 9, or Day 10.

Embodiment 141. A method of improving the efficacy of bupropion in treating depression, comprising: orally administering about 90 mg to about 125 mg of a bupropion in combination with about 0.3 mg/kg to about 1 mg/kg of a dextromethorphan, once or twice a day for at least 23 days, to a human being suffering from depression, wherein orally administering the bupropion in combination with the dextromethorphan is more effective in treating depression than orally administering the same dosage regimen of bupropion without dextromethorphan.

Embodiment 142. The method of embodiment 141, wherein about 0.6 mg/kg to about 0.8 mg/kg of the dextromethorphan is orally administered once or twice a day.

Embodiment 143. The method of embodiment 141, wherein about 45 mg of the dextromethorphan is orally administered once or twice a day.

Embodiment 144. The method of embodiment 141, wherein about 100 mg to about 120 mg of the bupropion is orally administered once or twice a day.

Embodiment 145. The method of embodiment 142, wherein about 105 mg of the bupropion is orally administered once or twice a day.

Embodiment 146. The method of embodiment 141, wherein the dextromethorphan and the bupropion are orally administered for at least 35 days.

Embodiment 147. The method of embodiment 141, wherein the human being is suffering from treatment-resistant depression.

Embodiment 148. The method of embodiment 141, wherein the dextromethorphan is orally administered in a dosage form that provides immediate release of the dextromethorphan.

Embodiment 149. The method of embodiment 143, wherein the dextromethorphan is orally administered in a dosage form that provides immediate release of the dextromethorphan.

Embodiment 150. The method of embodiment 141, wherein the bupropion is orally administered in a dosage form that provides sustained release of the bupropion.

Embodiment 151. The method of embodiment 145, wherein the bupropion is orally administered in a dosage form that provides sustained release of the bupropion.

Embodiment 152. The method of embodiment 150, wherein about 105 mg of the bupropion is orally administered once or twice a day in a dosage form that provides sustained release of the bupropion.

Embodiment 153. The method of embodiment 152, wherein the bupropion and the dextromethorphan are orally administered together in a single dosage form that is orally administered once or twice a day.

Embodiment 154. The method of embodiment 153, wherein the dextromethorphan and the bupropion are orally administered for at least 5 weeks.

Embodiment 155. The method of embodiment 141, wherein the human being is suffering from major depressive disorder.

Embodiment 156. The method of embodiment 154, wherein the bupropion comprises an enantiomeric excess of an R-enantiomer.

Embodiment 157. The method of embodiment 154, wherein the bupropion comprises an enantiomeric excess of an S-enantiomer.

Embodiment 158. The method of embodiment 141, wherein the dextromethorphan comprises a deuterium-modified dextromethorphan.

Embodiment 159. The method of embodiment 141, wherein the human being is currently suffering from depression and has previously been unsuccessfully treated with at least two antidepressants.

Embodiment 160. A method of treating treatment-resistant depression comprising:

selecting a human being suffering from depression who has previously been unsuccessfully treated with at least one antidepressant; and orally administering a dextromethorphan-bupropion combination treatment once or twice a day to the human being for at least about five weeks;

wherein the dextromethorphan-bupropion combination treatment comprises about 40 mg to about 70 mg of a dextromethorphan and about 100 mg to about 140 mg of a bupropion.

Embodiment 161. The method of embodiment 160, wherein the bupropion comprises an enantiomeric excess of an enantiomer.

Embodiment 162. The method of embodiment 160, wherein the dextromethorphan comprises a deuterium-modified dextromethorphan.

Embodiment 163. The method of embodiment 160, wherein the dextromethorphan-bupropion combination treatment comprises about 40 mg to about 50 mg of the dextromethorphan.

Embodiment 164. The method of embodiment 160, wherein the dextromethorphan-bupropion combination treatment comprises about 100 mg to about 110 mg of the bupropion.

Embodiment 165. The method of embodiment 163, wherein the dextromethorphan-bupropion combination treatment comprises about 100 mg to about 110 mg of the bupropion.

Embodiment 166. The method of embodiment 165, wherein the dextromethorphan and the bupropion are orally administered in a single dosage form that provides immediate release for the dextromethorphan and sustained release for the bupropion.

Embodiment 167. The method of embodiment 166, further comprising orally administering the dextromethorphan-bupropion combination treatment once a day for about 1, 2, 3, 4, 5, 6, or 7 days prior to orally administering the dextromethorphan-bupropion combination treatment twice a day to the human being for at least about five weeks.

Embodiment 168. The method of embodiment 167, wherein the dextromethorphan-bupropion combination treatment comprises about 45 mg of the dextromethorphan.

Embodiment 169. The method of embodiment 168, wherein the dextromethorphan-bupropion combination treatment comprises about 105 mg of the bupropion.

Embodiment 170. The method of embodiment 160, wherein the antidepressant is duloxetine.

Embodiment 171. A method of rapidly relieving the symptoms of depression, comprising administering a combination of bupropion and dextromethorphan once daily or twice daily to a human being in need thereof, wherein the human being experiences a therapeutic effect within 2 weeks of the first day that the combination of bupropion and dextromethorphan is administered.

Embodiment 172. A method of treating depression, comprising administering a combination of bupropion and dextromethorphan once daily or twice daily to a human being in need thereof, wherein the human being is of Asian descent.

Embodiment 173. Use of a combination of bupropion and dextromethorphan in the manufacture of a medicament for rapidly relieving the symptoms of depression, wherein the medicament is administered once daily or twice daily to achieve a therapeutic effect within 2 weeks of the first day that the medicament is administered.

Embodiment 174. Use of a combination of bupropion and dextromethorphan in the manufacture of a medicament for the treatment of a depression, wherein the medicament is administered once daily or twice daily to a human being of Asian descent.

Embodiment 175. The method of embodiment 171 or 172 or the use of embodiment 173 or 174, wherein the human being is of Japanese descent.

Embodiment 176. The method of embodiment 171 or 172 or the use of embodiment 173 or 174, wherein the human being is of Chinese descent.

Embodiment 177. The method of embodiment 171 or 172 or the use of embodiment 173 or 174, wherein the human being is of Korean descent.

Embodiment 178. The method or the use of embodiment 171, 172, 173, 174, 175, 176, or 177, wherein about 105 mg of bupropion hydrochloride, or a molar equivalent amount of: 1) another salt form of bupropion or a 2) free base form of bupropion, is orally administered once daily or twice daily.

Embodiment 179. The method or the use of embodiment 171, 172, 173, 174, 175, 176, 177, or 178, wherein about 44 mg to about 46 mg of dextromethorphan hydrobromide, or a molar equivalent amount of: 1) another salt form of dextromethorphan or a 2) free base form of dextromethorphan, is orally administered once daily or twice daily.

Embodiment 180. The method or the use of embodiment 171, 172, 173, 174, 175, 176, 177, 178, or 179, wherein the human being has previously had an inadequate response to at least one antidepressant therapy.

Embodiment 181. The method or the use of embodiment 171, 172, 173, 174, 175, 176, 177, 178, 179, or 180, wherein the depression is major depressive disorder.

Embodiment 182. The method or the use of embodiment 171, 172, 173, 174, 175, 176, 177, 178, 179, 180, or 181, wherein the depression is treatment resistant depression.

Embodiment 183. The method or the use of embodiment 171, 172, 173, 174, 175, 176, 177, 178, 179, 180, 181, or 182, wherein the combination of bupropion and dextromethorphan is administered once daily or twice daily for at least 30 days.

Embodiment 184. The method or the use of embodiment 171, 172, 173, 174, 175, 176, 177, 178, 179, 180, 181, or 182, wherein the combination of bupropion and dextromethorphan is administered once daily or twice daily for at least 42 days.

Embodiment 185. The method or the use of embodiment 171, 172, 173, 174, 175, 176, 177, 178, 179, 180, 181, 182, 183, or 184, wherein administration of the combination of bupropion and dextromethorphan results in the MADRS score reduced by at least about 10% as compared with baseline.

Embodiment 186. The method or the use of embodiment 171, 172, 173, 174, 175, 176, 177, 178, 179, 180, 181, 182, 183, or 184, wherein administration of the combination of bupropion and dextromethorphan results in the MADRS score reduced by at least about 10% as compared with placebo.

Embodiment 187. A method of treating nicotine addiction associated with smoking tobacco comprising administering a combination of a bupropion and a dextromethorphan daily for at least 21 consecutive days to a person suffering from nicotine addiction, wherein the person is an ad-lib tobacco smoker, wherein a total amount of 200 mg to 250 mg of bupropion and 80 mg to 140 mg of dextromethorphan are administered to the person daily, and wherein the method is more effective than administering the same amount of bupropion alone.

Embodiment 188. The method of embodiment 187, wherein the administration of the combination of the bupropion and the dextromethorphan resulted in at least 10% greater reduction in an intensity of the nicotine self-administration as compared to bupropion alone as measured by the reduction in the average number of cigarettes smoked per day.

Embodiment 189. The method of embodiment 187, wherein the administration of the combination of the bupropion and the dextromethorphan resulted in at least 15% greater reduction in an intensity of the nicotine self-administration as compared to bupropion alone as measured by the reduction in the average number of cigarettes smoked per day.

Embodiment 190. The method of embodiment 187, wherein the administration of the combination of the bupropion and the dextromethorphan resulted in at least 20% greater reduction in an intensity of the nicotine self-administration as compared to bupropion alone as measured by the reduction in the average number of cigarettes smoked per day.

Embodiment 191. The method of embodiment 187, wherein the administration of the combination of the bupropion and the dextromethorphan resulted in at least 10% greater reduction in expired carbon monoxide levels as compared to bupropion alone.

The method of embodiment 1, wherein the person taking a medication of the combination of the bupropion and the dextromethorphan twice a day in 2 equal amount of divided doses resulted in greater reduction in an intensity of the nicotine self-administration on the day or following day of the administration than the person taking only one of the 2 divided doses or not taking the medication of the combination.

Embodiment 192. The method of embodiment 187, wherein the combination of the bupropion and the dextromethorphan is administered to the person daily for at least 42 consecutive days.

Embodiment 193. The method of embodiment 187, wherein about 105 mg of the bupropion is administered to the person twice daily.

Embodiment 194. The method of embodiment 187, wherein about 200 mg to about 250 mg of the bupropion is administered daily to the person in two divided doses.

Embodiment 195. The method of embodiment 187, wherein about 90 mg of the dextromethorphan is administered to the person daily.

Embodiment 196. The method of embodiment 187, wherein about 45 mg of the dextromethorphan in each dose is administered to the person twice daily.

Embodiment 197. The method of embodiment 1, wherein about 40 mg to about 50 mg of the dextromethorphan in each dose is administered to the person twice daily.

Embodiment 198. The method of embodiment 187, wherein about 45 mg of the dextromethorphan and about 105 mg of bupropion are administered to the person twice daily.

Embodiment 199. The method of embodiment 187, wherein the weight ratio of dextromethorphan to bupropion is about 0.1 to about 0.5.

Embodiment 200. The method of embodiment 187, wherein the weight ratio of dextromethorphan to bupropion is about 0.4 to about 0.5.

Embodiment 201. The method of embodiment 187, wherein, to the person addicted to nicotine, the method is more effective than administering the dextromethorphan alone.

Embodiment 202. The method of embodiment 187, wherein about 105 mg of the bupropion is administered to the person once daily for three days, followed by administering 105 mg of the bupropion in each dose twice daily to the person for at least 21 days.

Embodiment 203. The method of embodiment 202, wherein, to the person addicted to nicotine, the method is more effective, as measured on day 24 of treatment, than a control method, wherein the control method consists of administering 105 mg of the bupropion alone to the person once daily for three days, followed by administering 105 mg of the bupropion alone in each dose twice daily to the person for 21 days.

Embodiment 204. The method of embodiment 187, wherein about 105 mg of the bupropion is administered to the person once daily for three days, followed by administering 105 mg of the bupropion in each dose twice daily to the person for at least 39 days.

Embodiment 205. The method of embodiment 204, wherein, to the person addicted to nicotine, the method is more effective, as measured on day 42 of treatment, than a control method, wherein the control method consists of administering 105 mg of the bupropion alone to the person once daily for three days, followed by administering 105 mg of the bupropion alone in each dose twice daily to the person for 39 days.

Embodiment 206. The method of embodiment 204, wherein, to the person addicted to nicotine, the method is more effective, as measured on day 42 of treatment, than a control method, wherein the control method consists of administering 105 mg of the bupropion alone to the person once daily for three days, followed by administering 105 mg of the bupropion alone in each dose twice daily to the person for 39 days.

Embodiment 207. The method of embodiment 187, wherein about 45 mg of the dextromethorphan is administered to the person once daily for three days, followed by administering 45 mg of the dextromethorphan in each dose twice daily to the person for at least 21 days.

Embodiment 208. The method of embodiment 198, wherein the method is more effective, as measured on day 21 of treatment, than a control method, wherein the control method consists of administering 105 mg of the bupropion alone to the person twice daily to the person for 21 days.

Embodiment 209. The method of embodiment 187, wherein the bupropion has an enantiomeric excess of the R-enantiomer that is at least 90%.

Embodiment 210. The method of embodiment 187, wherein the bupropion has an enantiomeric excess of the S-enantiomer that is at least 90%.

Embodiment 211. The method of embodiment 187, wherein the bupropion is deuterium enriched.

Embodiment 212. The method of embodiment 187, wherein the dextromethorphan is deuterium enriched.

EXAMPLES

Example 1

Fifteen human subjects were randomized into one of two treatment groups receiving either dextromethorphan (DM) alone, or DM in combination with bupropion, as shown in Table 1 below.

TABLE 1

| | Study Design | | | |
|---|---|---|---|---|
| Group | Dose Levels Bupropion/DM | Dosing Regimen | Duration | Total Subjects |
| A | 0 mg/60 mg | DM: Twice daily, Days 1-8 | Days 1-8 | 8 |
| B | 150 mg/60 mg | Bupropion: Once daily, Days 1-3; Twice daily, Days 4-8 DM: Twice daily, Days 1-8 | Days 1-8 | 7 |

All subjects were extensive, including ultra-rapid, metabolizers of dextromethorphan as determined by CYP2D6 genetic testing. Dextromethorphan was dosed at 12-hour intervals on Days 1-8, with a final morning dose on Day 8. Bupropion was dosed once daily on Days 1-3, and at 12-hour intervals thereafter, with a final morning dose on Day 8.

Plasma samples were collected for concentration analysis of dextromethorphan, total dextrorphan, bupropion, hydroxybupropion, erythrohydroxybupropion, and threohydroxybupropion on days 1 and 8. Plasma samples for determination of trough concentrations of dextromethorphan were obtained approximately 12 hours after dosing on days 1, 5, 6, and 8.

Concentrations of dextromethorphan, total dextrorphan (unconjugated and glucuronide forms), bupropion, hydroxybupropion, erythrohydroxybupropion, and threohydroxybupropion, were determined using LC-MS/MS. Pharmacokinetic parameters were calculated.

Phenotypic determination of dextromethorphan metabolizer status was performed by calculating the dextromethorphan/dextrorphan metabolic ratio as described in Jurica et al. *Journal of Clinical Pharmacy and Therapeutics*, 2012, 37, 486-490. Plasma concentrations of dextromethorphan and dextrorphan 3 hours after dosing were used, with a dextromethorphan/dextrorphan ratio of 0.3 or greater indicating a poor metabolizer phenotype.

Results

Plasma concentrations of dextromethorphan were significantly increased with bupropion administration, as illustrated in FIG. 1 and Table 2.

TABLE 2

| Mean Day 8 Dextromethorphan Plasma Concentrations (ng/mL) | | |
|---|---|---|
| Time (hours) | Dextromethorphan (Group A) | Dextromethorphan + Bupropion (Group B) |
| 0 | 1.2 | 110.6 |
| 1 | 2.4 | 129.3 |
| 2 | 3.6 | 153.9 |

TABLE 2-continued

Mean Day 8 Dextromethorphan Plasma Concentrations (ng/mL)

| Time (hours) | Dextromethorphan (Group A) | Dextromethorphan + Bupropion (Group B) |
|---|---|---|
| 3 | 3.6 | 151.6 |
| 4 | 3.3 | 149.1 |
| 6 | 2.5 | 150.0 |
| 8 | 1.9 | 144.4 |
| 12 | 1.1 | 119.3 |
| 24 | 0.4 | 95.3 |
| 36 | 0.1 | 69.0 |

Figure 2:
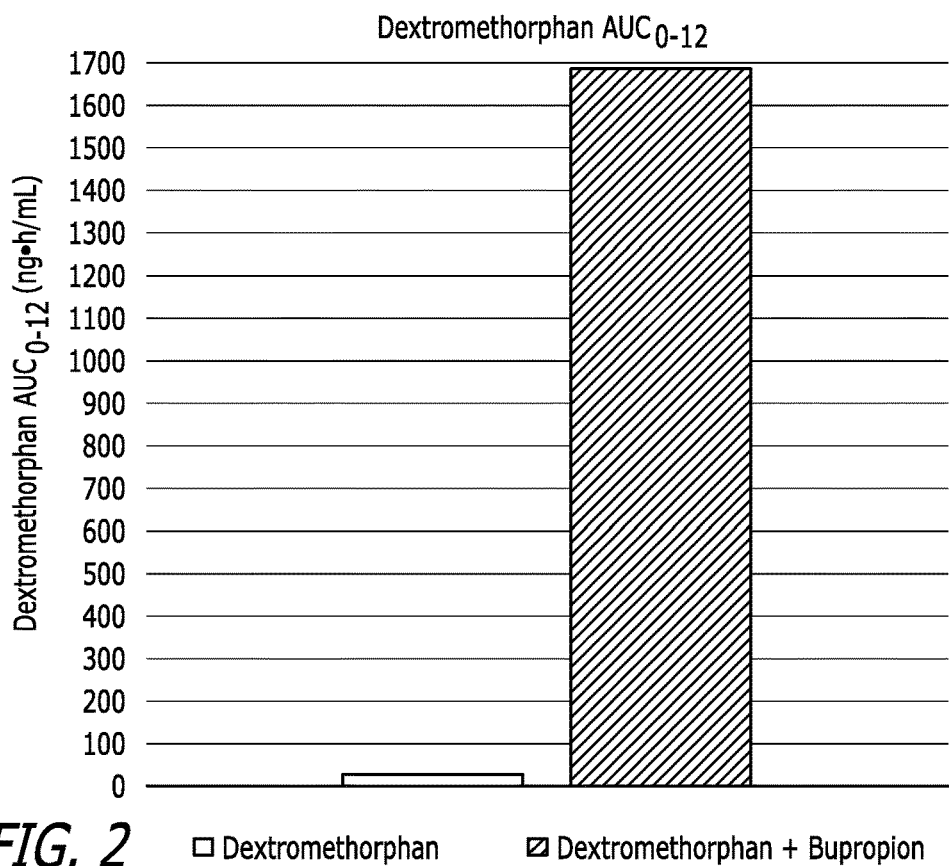
FIG. 2 depicts mean $AUC_{0-12}$ of dextromethorphan on Day 8 for subjects administered dextromethorphan alone or dextromethorphan and bupropion.
Figure 3:
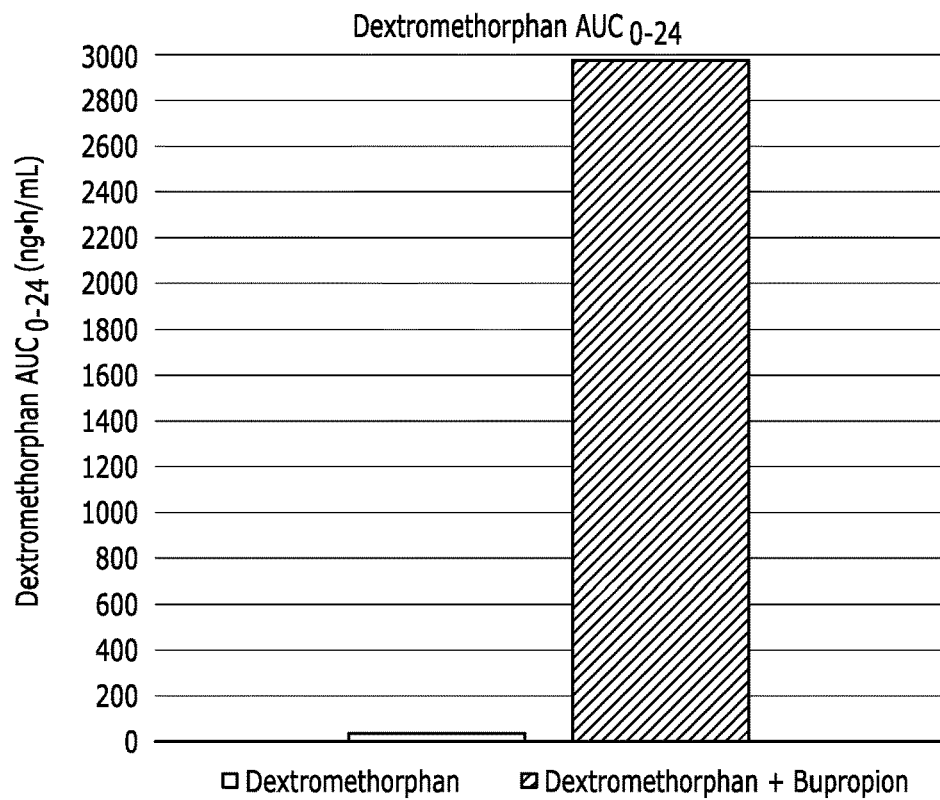
FIG. 3 depicts mean $AUC_{0-24}$ of dextromethorphan on Day 8 for subjects administered dextromethorphan alone or dextromethorphan and bupropion.
Figure 4:
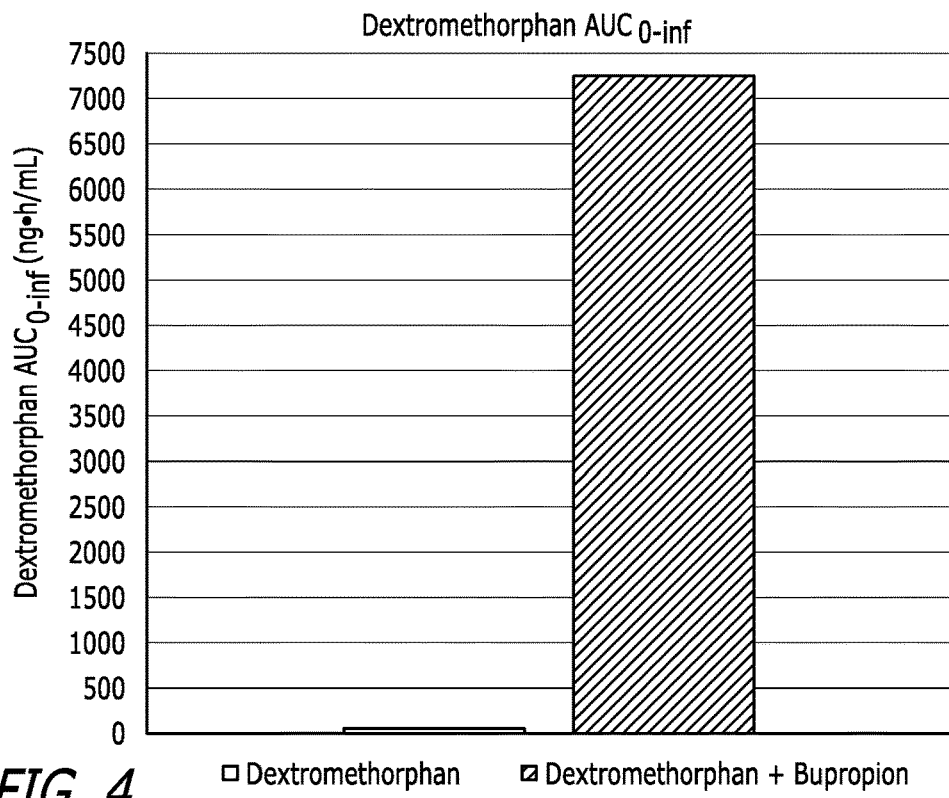
FIG. 4 depicts mean $AUC_{0-inf}$ of dextromethorphan on Day 8 for subjects administered dextromethorphan alone or dextromethorphan and bupropion.
Figure 5:
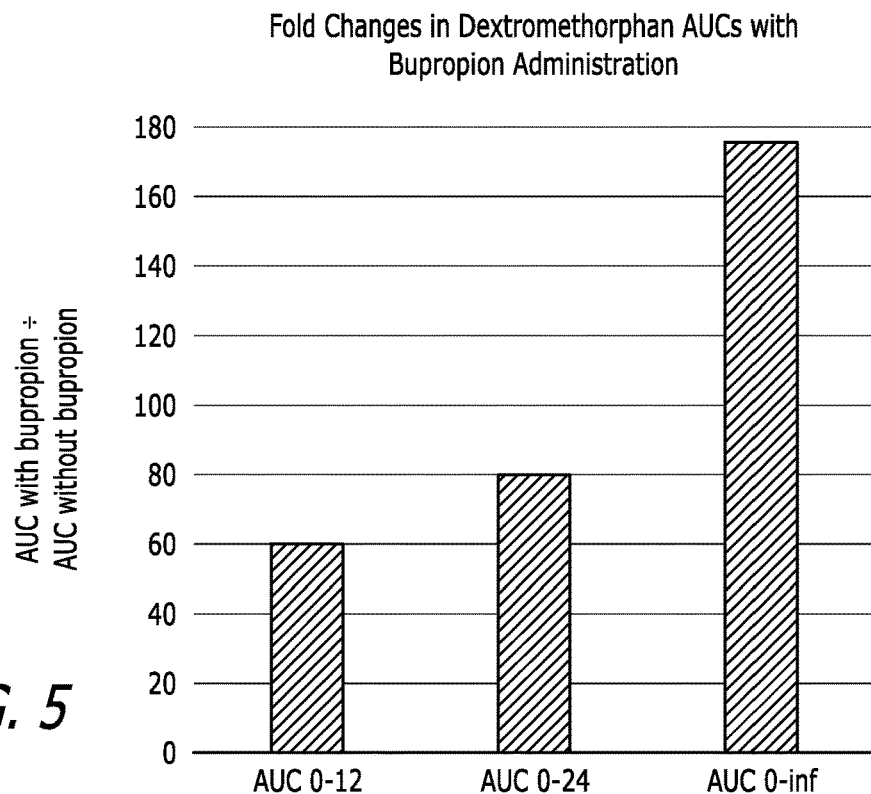
FIG. 5 depicts the fold changes in AUCs of dextromethorphan on Day 8 for subjects administered dextromethorphan alone as compared to dextromethorphan and bupropion.
Figure 6:
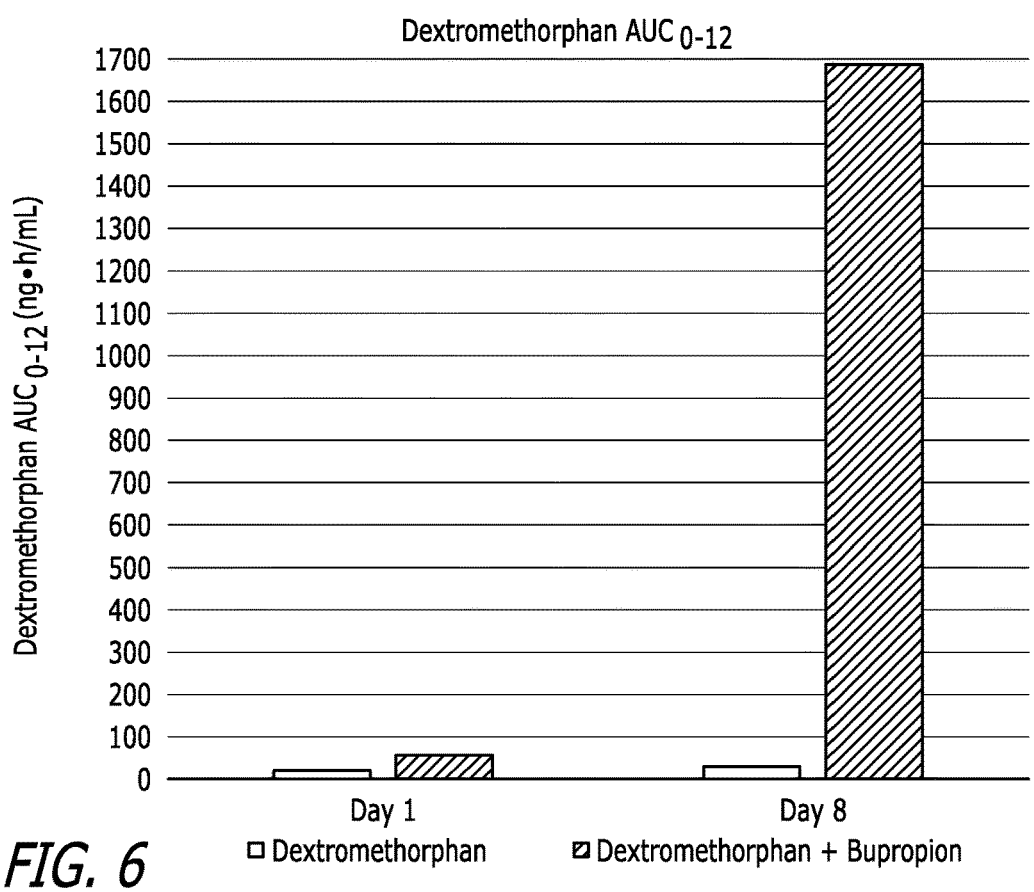
FIG. 6 depicts mean $AUC_{0-12}$ of dextromethorphan on Day 1 and Day 8 for subjects administered dextromethorphan alone or dextromethorphan and bupropion.

The AUC of dextromethorphan was significantly increased with administration of bupropion as show in FIGS. 2-4. As shown in FIG. 5 and Table 2A, administration of bupropion with dextromethorphan resulted in an approximately 60-fold, 80-fold, and 175-fold increase in mean dextromethorphan $AUC_{0-12}$, $AUC_{0-24}$, and $AUC_{0-inf}$, respectively on Day 8 as compared to administration of dextromethorphan alone. As shown in FIG. 6 and Table 2B, the increase in dextromethorphan AUC occurred as early as Day 1 (an approximate 3-fold increase in $AUC_{0-12}$)

TABLE 2A

Day 8 Values

|  | Dextromethorphan (Group A) | Dextromethorphan + Bupropion (Group B) |
|---|---|---|
| $AUC_{0-12}$ (ng * hr/mL) | 28.1 | 1,686.3 |
| $AUC_{0-24}$ (ng * hr/mL) | 37.1 | 2,975.3 |
| $AUC_{0-inf}$ (ng * hr/mL) | 41.2 | 7,237.3 |
| $C_{max}$ (ng/mL) | 3.8 | 158.1 |
| $C_{min}$ (ng/mL) | 1.1 | 119.3 |
| $C_{avg}$ (ng/mL) | 2.3 | 140.5 |

TABLE 2B

Day 1 Values

|  | Dextromethorphan (Group A) | Dextromethorphan + Bupropion (Group B) |
|---|---|---|
| $AUC_{0-12}$ (ng * hr/mL) | 20.1 | 56.5 |
| $C_{max}$ (ng/mL) | 3.0 | 8.7 |

Figure 7:
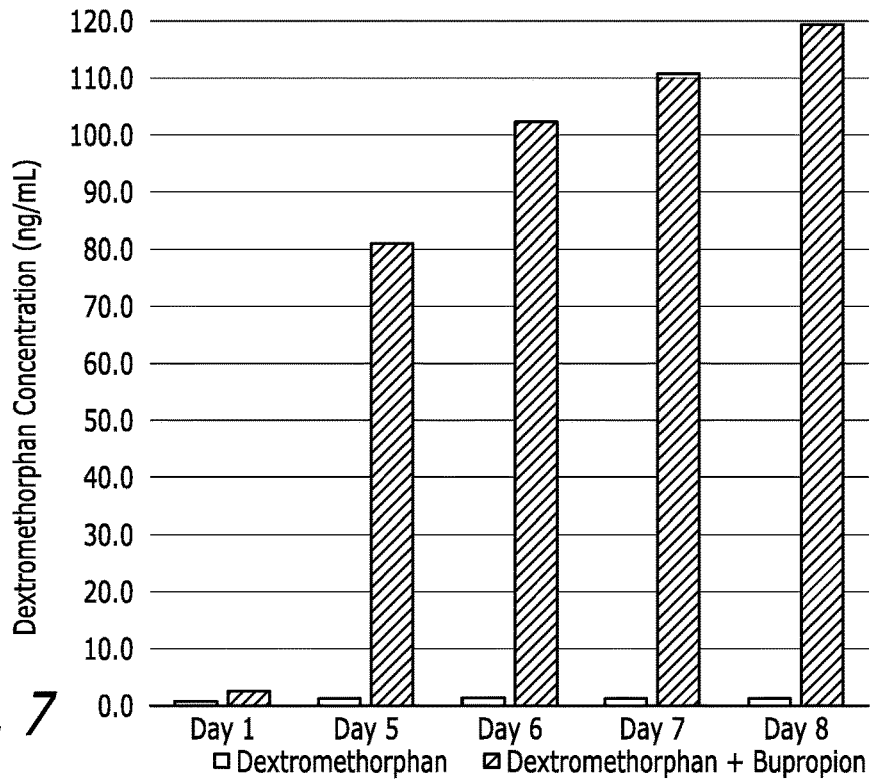
FIG. 7 depicts mean dextromethorphan trough plasma concentrations for subjects administered dextromethorphan alone or dextromethorphan and bupropion.

Trough plasma concentrations (also referred to as "minimum mean plasma concentrations" or "$C_{min}$") of dextromethorphan were significantly increased with administration of bupropion as illustrated in FIG. 7 and Tables 2A and 3. Administration of bupropion with dextromethorphan resulted in an approximately 105-fold increase in mean trough plasma concentration of dextromethorphan on Day 8 as compared to administration of dextromethorphan alone.

Figure 8:
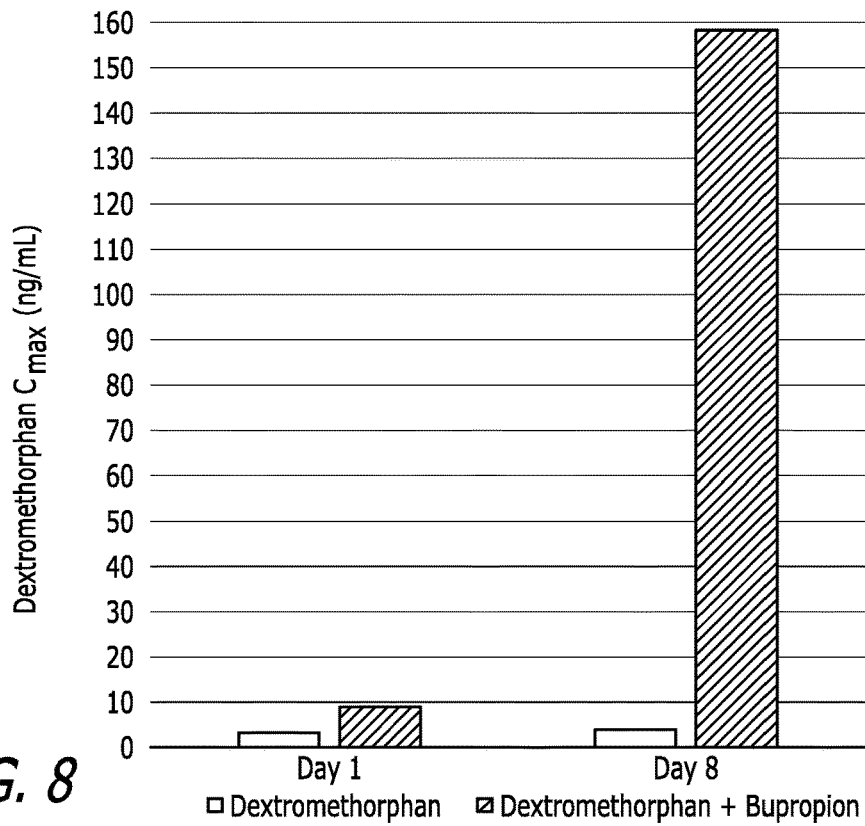
FIG. 8 depicts mean dextromethorphan maximum plasma concentrations on Day 1 and Day 8 for subjects administered dextromethorphan alone or dextromethorphan and bupropion.

Mean average plasma concentrations ($C_{avg}$) of dextromethorphan on Day 8 increased approximately 60-fold with bupropion administration as compared to administration of dextromethorphan alone, as illustrated in Table 2A. Maximum mean plasma concentrations ($C_{max}$) were also significantly increased as illustrated in FIG. 8 and Table 2A.

TABLE 3

Mean Trough Dextromethorphan Plasma Concentrations (ng/mL)

|  | Dextromethorphan (Group A) | Dextromethorphan + Bupropion (Group B) | Fold Change |
|---|---|---|---|
| Day 1 | 0.7 | 2.5 | 3.5 |
| Day 5 | 1.2 | 80.9 | 70 |
| Day 6 | 1.3 | 102.2 | 78 |
| Day 7 | 1.2 | 110.6 | 94 |
| Day 8 | 1.1 | 119.3 | 105 |

The $T_{max}$ and elimination half-life ($T_{1/2\ el}$) of dextromethorphan were significantly increased with administration of bupropion on Day 8. The increase of $T_{1/2\ el}$ shows that the metabolic lifetime of dextromethorphan was increased. Administration of bupropion with dextromethorphan resulted in a mean $T_{max}$ of 3.6 hours, compared to 2.3 hours for dextromethorphan alone. Administration of bupropion with dextromethorphan resulted in a mean $T_{1/2\ el}$ of 27.7 hours, compared to 6.6 hours for dextromethorphan alone.

Figure 9:
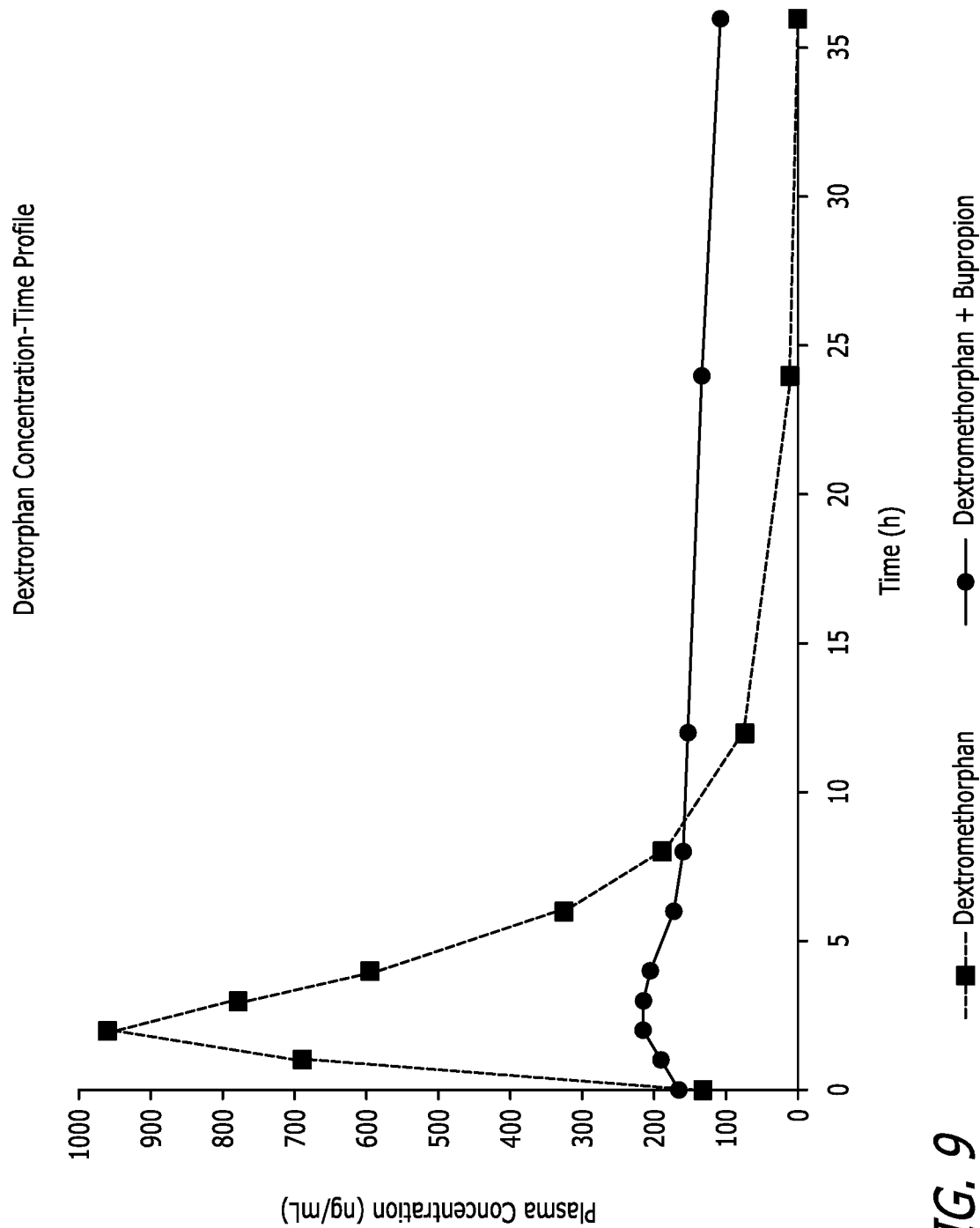
FIG. 9 is a plot of the mean plasma concentrations of dextrorphan over time after dosing on Day 8 for subjects administered dextromethorphan alone or dextromethorphan and bupropion.

Plasma concentrations of dextrorphan were significantly decreased with bupropion administration, as illustrated in FIG. 9 and Table 4.

TABLE 4

Mean Day 8 Dextrorphan Plasma Concentrations (ng/mL)

| Time (hours) | Dextromethorphan (Group A) | Dextromethorphan + Bupropion (Group B) |
|---|---|---|
| 0 | 132.4 | 165.3 |
| 1 | 688.9 | 190.7 |
| 2 | 959.1 | 214.9 |
| 3 | 778.1 | 214.4 |
| 4 | 594.9 | 205.1 |
| 6 | 324.7 | 172.5 |
| 8 | 189.6 | 159.6 |
| 12 | 74.8 | 152.8 |
| 24 | 12.2 | 133.0 |
| 36 | 0.1 | 107.6 |

Figure 10:
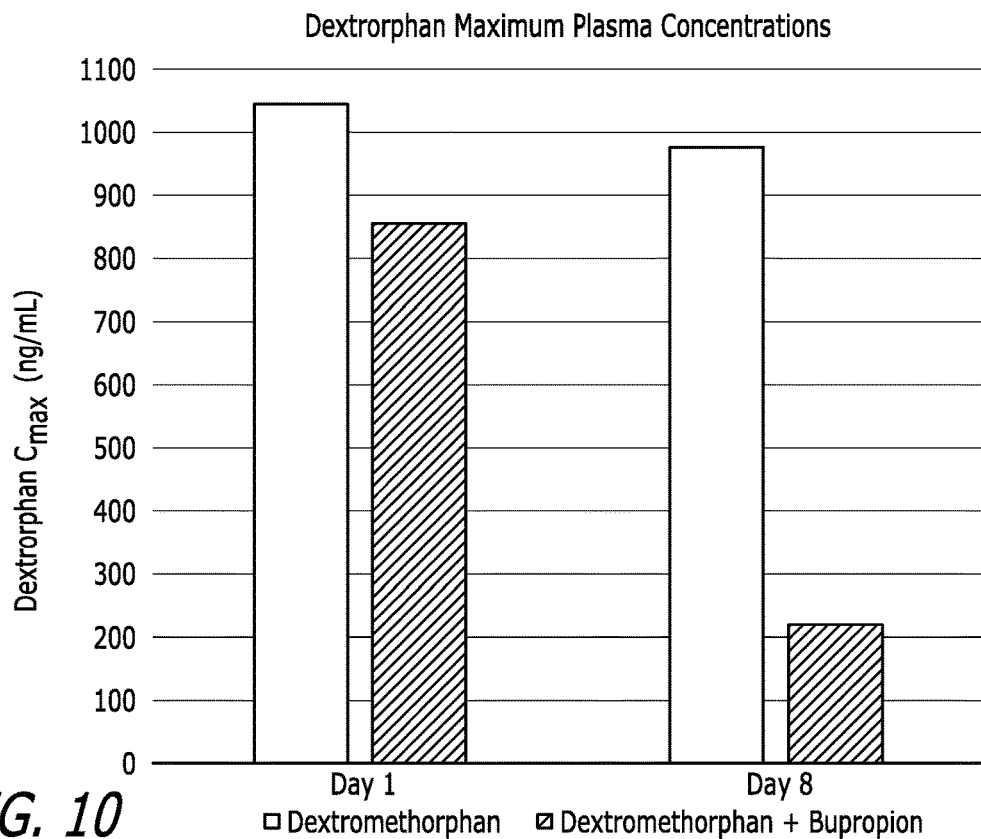
FIG. 10 depicts mean dextrorphan maximum plasma concentrations on Day 1 and Day 8 for subjects administered dextromethorphan alone or dextromethorphan and bupropion.
Figure 11:
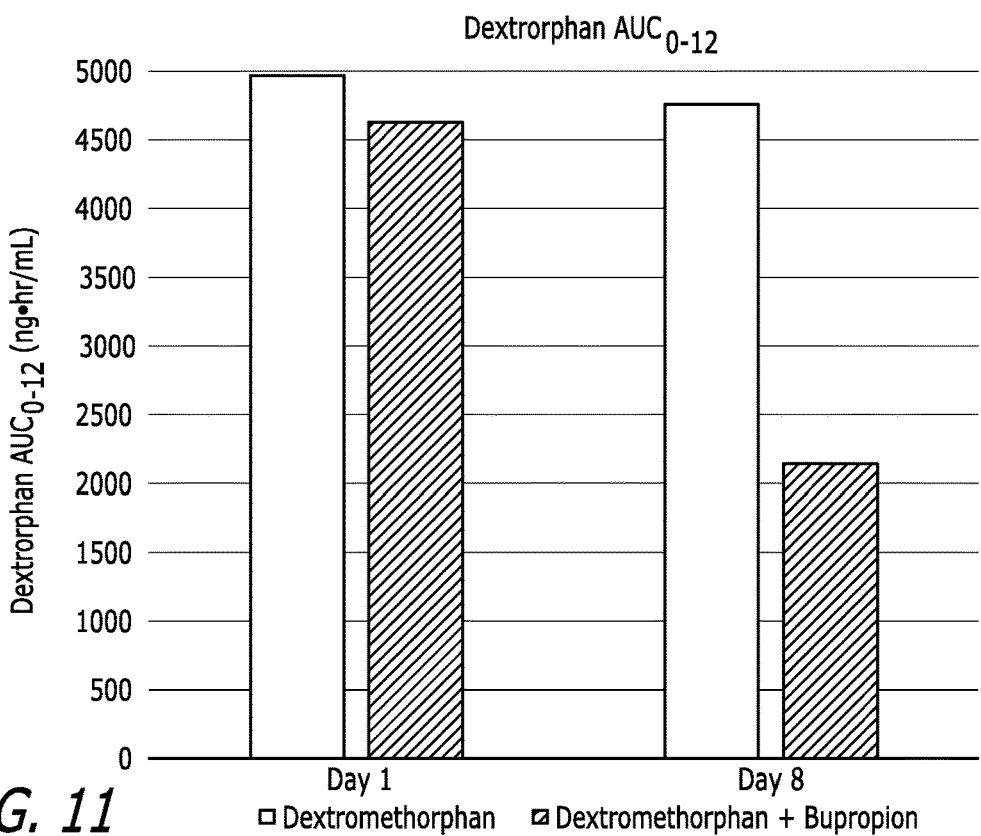
FIG. 11 depicts mean $AUC_{0-12}$ of dextrorphan on Day 1 and Day 8 for subjects administered dextromethorphan alone or dextromethorphan and bupropion.

As shown in FIGS. 10-11, there was an approximate 78% reduction in mean dextrorphan $C_{max}$, and an approximate 55% reduction in mean dextrorphan $AUC_{0-12}$ on Day 8 with administration of bupropion.

Phenotypic determination of dextromethorphan metabolizer status showed that no subjects in either treatment arm were poor metabolizers on Day 1. On Day 8 however, 100% of subjects treated with bupropion had converted to poor metabolizer status as compared to 0% of subjects treated with dextromethorphan alone. The mean plasma dextromethorphan/dextrorphan metabolic ratio increased from 0.01 on Day 1 to 0.71 on Day 8 with bupropion administration. The mean ratio in the group administered DM alone was 0.00 on Day 1 and remained unchanged on Day 8.

On Day 8, average plasma concentrations of bupropion, hydroxybupropion, erythrohydroxybupropion, and threohydroxybupropion were at least 10 ng/mL, 200 ng/mL, 20 ng/mL, and 100 ng/mL, respectively after bupropion administration.

As used in this section, the term "fold change" or "fold increase" refers to the ratio of a value for bupropion with dextromethorphan to the same value for dextromethorphan alone (i.e., the value for bupropion with dextromethorphan divided by the same value for dextromethorphan alone).

Example 2

The ability of various antidepressant compounds to inhibit the metabolism of dextromethorphan was examined using human liver microsomes. Each antidepressant compound was incubated at seven increasing concentrations (0.1-100 μM) in duplicate with human liver microsomes (0.5 mg/mL) in the presence of dextromethorphan (5 μM) at 37° C. The assay was performed in the presence of 2 mM NADPH in 100 mM potassium phosphate (pH 7.4) containing 5 mM magnesium chloride, in a 200 μl assay final volume.

After optimal incubation at 37° C., the reactions were terminated by addition of methanol containing internal standard for analytical quantification. The quenched samples were incubated at 4° C. for 10 minutes and centrifuged at 4° C. for 10 minutes. The supernatant was removed, and the metabolite of dextromethorphan (dextrorphan) was analyzed by LC-MS/MS. A decrease in the formation of the metabolite compared to vehicle control was used to calculate an $IC_{50}$ value (the test concentration which produces 50% inhibition of dextromethorphan metabolism) for each antidepressant compound, with a lower $IC_{50}$ indicating greater potency.

Figure 12:
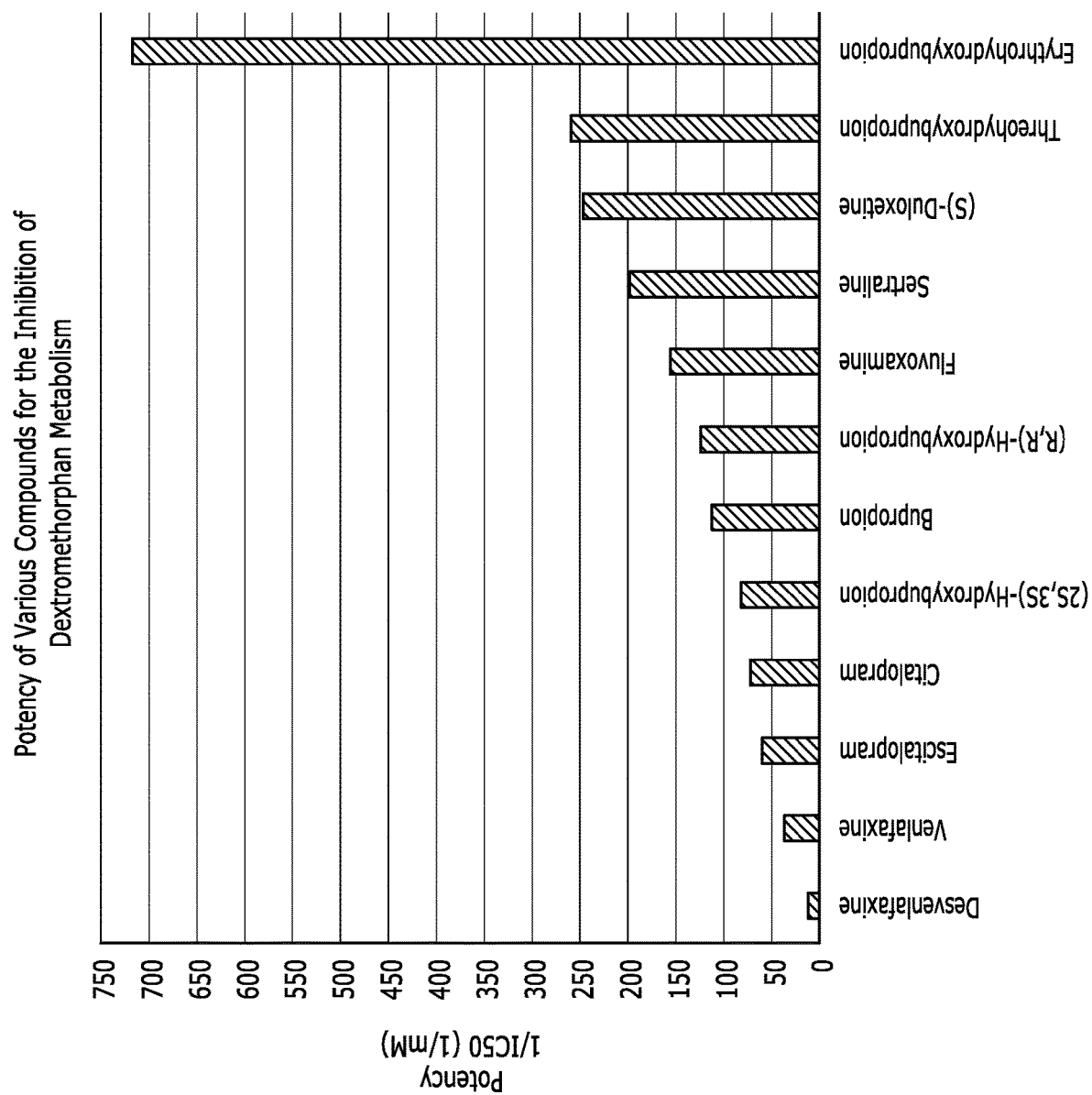
FIG. 12 depicts the potency of various antidepressant compounds for inhibition of the metabolism of dextromethorphan in human liver microsomes.

The results are summarized in Table 5 below, and the corresponding potencies are depicted in FIG. 12.

TABLE 5

Potency of Various Antidepressant Compounds for Inhibition of the Metabolism of Dextromethorphan in Human Liver Microsomes

| Test Compound | Mean $IC_{50}$ (μM) |
|---|---|
| Desvenlafaxine | 97.3 |
| Venlafaxine | 27.7 |
| Escitalopram | 17.1 |
| Citalopram | 14.1 |
| (2S,3S)-Hydroxybupropion | 12.5 |
| Bupropion | 9.1 |
| (R,R)-Hydroxybupropion | 8.2 |
| Fluvoxamine | 6.5 |
| Sertraline | 5.1 |
| (S)-Duloxetine | 4.1 |
| Threohydroxybupropion | 3.9 |
| Erythrohydroxybupropion | 1.4 |

Example 3

Phase 2 clinical trial design:

The Phase 2 clinical trial with the administration of a combination of dextromethorphan and bupropion (DM/BU) was a randomized, double-blind, active-controlled, multi-center, U.S. trial with 80 adult patients with confirmed diagnosis of moderate to severe major depressive disorder (MDD), who received a twice daily dose for a 6-week treatment period. Dose groups (1:1 randomization) included DM/BU (45 mg dextromethorphan/105 mg bupropion) with 43 patients, or active comparator bupropion (105 mg) with 37 patients. Among these patients, 23% of them had received prior first line treatment for depression. The clinical trial had extensive quality control measures.

The Primary Endpoint:

The changes from baseline in the Montgomery-Åsberg Depression Rating Scale (MADRS) total score over the 6-week treatment period were calculated at each time point and averaged.

Figure 13:
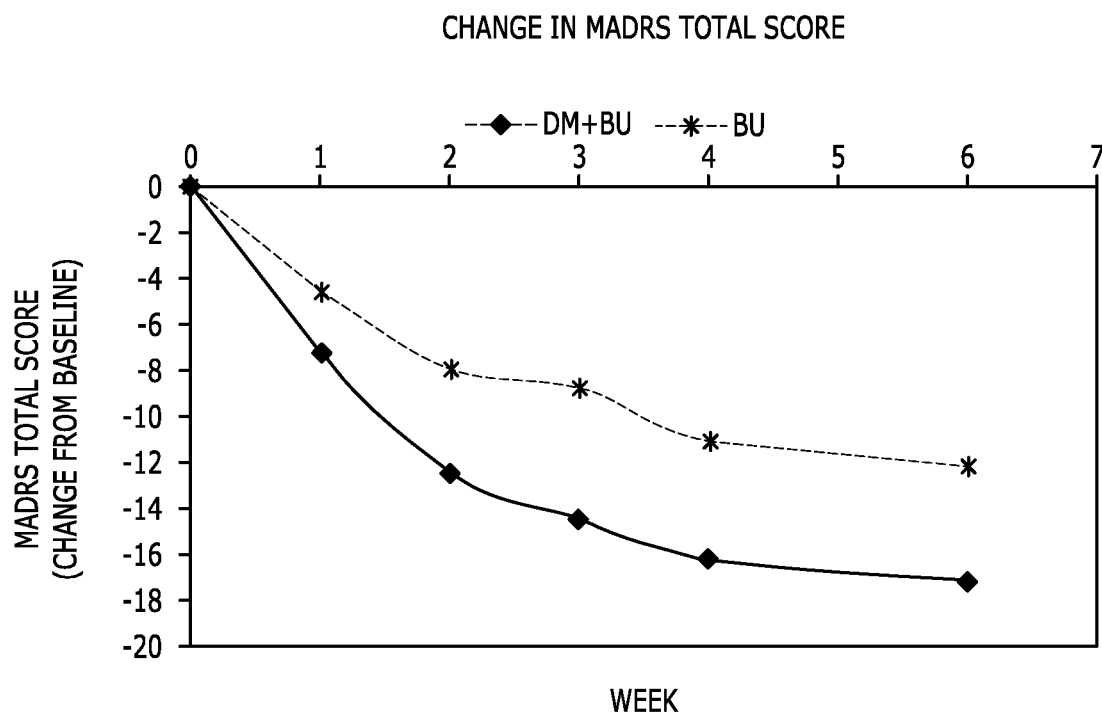
FIG. 13 is a plot of the average MADRS total score change from baseline over time during the 6-week dosing period for subjects administered bupropion alone or the combination of dextromethorphan and bupropion.

FIG. 13 and Table A shows the changes in MADRS total score over the time during the 6-week dosing period for the subjects administered bupropion (BU) or the combination of dextromethorphan and bupropion (DM/BU).

TABLE A

| Primary Endpoint | DM + BU | BU | P-Value |
|---|---|---|---|
| Change in MADRS Total Score over 6-week period (averaged) | −13.7 | −8.8 | <0.001 |
| Change in MADRS Total Score at week 6 | −17.2 | −12.1 | 0.013 |

The Secondary Endpoints:

Table B listed the secondary endpoints with P-values.

TABLE B

| Secondary Endpoint | P-Value* |
|---|---|
| MADRS Total Score Change Weeks 1-2 | 0.01 |
| % Achieving Remission on MADRS at Week 2 | 0.004 |
| % Achieving Remission on MADRS at Week 6 | 0.004 |
| MADRS-6 Change at Week 6 | 0.007 |
| % of Responders on MADRS-6 (≥50% reduction from baseline) at Week 6 | 0.014 |
| Clinical Global Impression-Improvement (CGI-I) at Week 1 | 0.045 |
| CGI-I at Week 6 | 0.051 |
| Clinical Global Impression-Severity (CGI-S) at Week 6 | 0.028 |

*P-values are for DM/BU versus active comparator bupropion (BU). Multiple secondary endpoints favored DM/BU.

Figure 14:
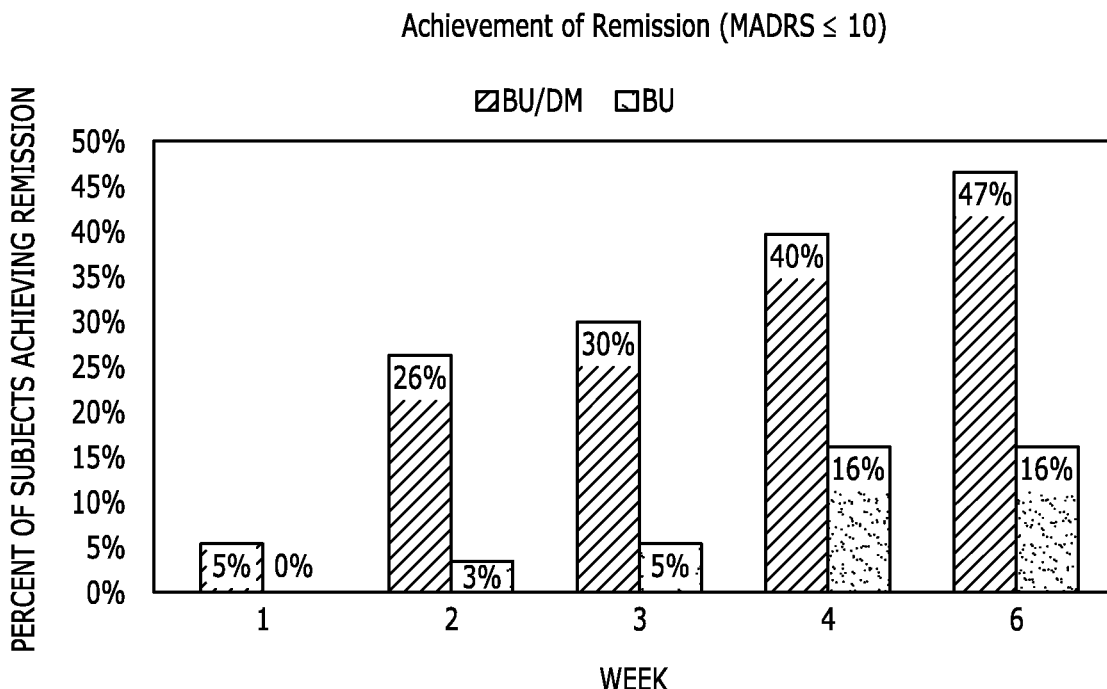
FIG. 14 depicts the percent of subjects achieving remission (MADRS 10) over time during the 6-week dosing period for subjects administered bupropion alone or the combination of dextromethorphan and bupropion.

FIG. 14 shows the percent of subjects achieving remission (as determined by MADRS 10) over the time during the 6-week dosing period for the subjects administered bupropion (BU) or the combination of dextromethorphan and bupropion (DM/BU).

Safety:

The clinical study showed that the administration of the DM/BU was safe and well tolerated with similar rates of adverse events in the DM/BU and bupropion arms. No serious adverse events were observed. There was no meaningful difference between the two treatment arms in discontinuations due to adverse events. The most commonly reported adverse events in the DM/BU arm were nausea, dizziness, dry mouth, decreased appetite, and anxiety. The DM/BU was not associated with psychotomimetic effects, weight gain, or increased sexual dysfunction.

SUMMARY

Statistically significant improvements on MADRS and secondary efficacy endpoints for DM/BU in patients with MDD were achieved. Early and sustained separation from active comparator bupropion were observed. The administration of DM/BU was safe and well-tolerated with no psychotomimetic effects, weight gain, or increased sexual dysfunction Thus, DM/BU demonstrated significant and rapid antidepressant activity with a favorable safety profile in the clinical trial in MDD.

Results:

FIGS. 13 and 14 are prepared based on the results of the US clinical trials with 80 adult patients having depression with 43 patients treated with the combination of 45 mg of DM and 105 mg of BU, and 37 patients treated with 105 mg of BU alone who received a twice daily dose for the 6-week treatment period. Among these patients, 23% of them had received prior first line treatment for depression.

As shown in FIG. 13 and Table A, the MADRS total score (depression rating scale) was significantly reduced with the combination of DM and BU than that of BU alone even at the first week of the treatment. At week 6, administration of the combination DM/BU reduced the MADRS total score by about 42% as compared to bupropion alone.

As shown in FIG. 14, even in as early as the second week of the treatment, the remission rate for the combination of DM/BU is significantly higher than that for the comparator BU alone (about 8 times) with about 20% higher remission rate. At week 6 of the treatment, the administration of combination DM/BU resulted in about 30% higher remission rate than that of the comparator BU alone.

The above clinical study showed that the administration of the combination of bupropion with dextromethorphan (DM/BU) provides greater efficacy than would otherwise be achieved by administering bupropion alone. This clinical study demonstrated that the combination of dextromethorphan and bupropion has an additive or synergistic efficacy in treating depression.

Example 4: Product Kit

In some embodiments, a product kit comprises a combination of dextromethorphan and bupropion, for treating depression, wherein the product kit contains a dosage form containing about 30 mg to about 60 mg of dextromethorphan and about 100 mg to about 200 mg of bupropion, and wherein administration of the dosage form once daily or twice daily results in greater efficacy in the human being than that for administering bupropion alone. In some embodiments, the product kit contains 45 mg of dextromethorphan and 105 mg of bupropion.

In some embodiments, a product kit comprises an oral sustained release delivery system for dextromethorphan, comprising bupropion; dextromethorphan; and a water soluble vehicle in a dosage form, wherein the dosage form contains about 30 mg to about 60 mg of dextromethorphan and about 100 mg to about 200 mg of bupropion, and wherein the use of the dosage form once or twice daily for at least eight days results in the increase of elimination half-life ($T_{1/2}$) of dextromethorphan than that for administration dextromethorphan alone on the eighth day.

Example 5

Nearly 40 million American adults smoke and around 70% of them report that they want to quit. Tobacco use results in approximately 500,000 premature deaths each year in the U.S. alone, according to the Centers for Disease Control and Prevention. Smoking is the single largest cause of premature deaths worldwide accounting for an estimated almost 20% of all deaths in developed countries [Dani J A and Heinemann S (1996) Neuron 16:5, pp. 905-8]. Direct health care and lost productivity costs as a result of smoking total nearly $300 billion a year in the U.S. alone. It is estimated that only 3 to 5% of cigarette smokers who attempt to quit without assistance are successful for 6-12 months, and the relapse rate remains above 80% even with current treatments [Hughes J R, et al. (2004) Addiction 99:1, pp. 29-38]. As the vast majority of smokers who attempt to quit fail to do so highlighting the need for new approaches. The combination of dextromethorphan and bupropion (DM/BU) has the potential to address this condition due to the novel mechanisms of action of DM/BU.

The dextromethorphan component of DM/BU is a sigma-1 receptor agonist, nicotinic acetylcholine receptor antagonist, and inhibitor of the serotonin and norepinephrine transporters. The bupropion component of DM/BU serves to increase the bioavailability of dextromethorphan, and is a norepinephrine and dopamine reuptake inhibitor, and a nicotinic acetylcholine receptor antagonist. Both components of DM/BU are nicotinic acetylcholine receptor antagonists, a mechanism that is relevant to nicotine dependence. Thus, DM/BU provides a potentially new mechanism of action for smoking cessation treatment.

Phase 2 Clinical Trial Design:

The clinical trial was a Phase 2, randomized, double-blind, active-controlled study to evaluate the efficacy and safety of DM/BU for smoking cessation treatment. A total of 58 smokers were randomized in a 1:1 ratio to receive either DM/BU (45 mg dextromethorphan/105 mg bupropion) (n=31), or the active comparator bupropion (105 mg) (n=27), twice daily, and assessed over a 3-week period. Enrolled subjects were daily smokers using 10 or more cigarettes per day. The average number of cigarettes smoked per day at baseline was 20 for DM/BU and 17 for the bupropion treatment groups.

The Primary Endpoint:

The primary outcome measure was the change in smoking intensity, measured using the number of cigarettes smoked per day, assessed via daily smoking diaries.

Reduction in ad-lib smoking was selected as the primary endpoint in this trial because it has been shown to correlate with smoking abstinence.

Safety:

Medication adherence was similar between the study arms for both the morning dose (97.1% for DM/BU and 96.6% for bupropion) and the evening dose (76.3% for DM/BU and 79.4% for bupropion). In the study, DM/BU was safe and well tolerated with no serious adverse events. The most commonly reported side effects were headache, dry mouth, and insomnia/vivid dreams, with similar incidences in both treatment arms.

Results:

Treatment with DM/BU resulted in a 25% greater reduction in the average number of cigarettes smoked per day over the 3-week period, the prespecified primary endpoint, as compared to bupropion (average reductions of 8.49 and 6.79 cigarettes per day for DM/BU and bupropion, respectively, p=0.0016).

Consistent with this finding, a greater proportion of smokers receiving DM/BU experienced a more than 50% reduction in expired carbon monoxide levels, a biochemical marker of smoking intensity, as compared to those treated with bupropion (52.0% for DM/BU versus 30.4% for bupropion, p=0.15).

In addition, the human subjects who took DM/BU as prescribed on a given day smoked 1.0 fewer cigarette on the day of medication use of DM/BU (p=0.026) and 1.2 fewer cigarettes on the following day (p=0.008) as compared to those who missed one or both doses of DM/BU.

SUMMARY

The treatment with DM/BU achieves the prespecified primary endpoint in Phase 2 Trial in Smoking Cessation. The treatment with DM/BUdemonstrated statistically significant reduction in daily smoking compared to the active comparator bupropion alone (p=0.0016). The findings in this phase 2 clinical trial are notable because DM/BU was compared to bupropion, which is an approved treatment for smoking cessation.

Furthermore, it is worth noting that the improvement of DM/BU over bupropion observed in this clinical trial in human beings is similar in magnitude to the improvement over placebo reported for the approved smoking cessation treatment varenicline in studies with a similar design. Varenicline is a prescription medication used to treat smoking addiction. This medication is the first approved nicotinic receptor partial agonist. Specifically, varenicline is a partial agonist of the alpha4/beta2 subtype of the nicotinic acetylcholine receptor.

Example 6

A Phase 3, randomized, double-blind, multicenter, placebo-controlled clinical trial of the combination of dextromethorphan (DM) and bupropion (BU or BUP) in patients with major depressive disorder (MDD) was conducted in the U.S. A total of 327 patients with a confirmed diagnosis of moderate to severe MDD were randomized in a 1:1 ratio to receive 45 mg dextromethorphan/105 mg bupropion (DM/BU) (n=163), or placebo (n=164) once daily for the first 3 days (day 1, day 2, and day 3) and twice daily thereafter (starting day 4) for a total of 6 weeks.

Baseline inclusion criteria included: Male or female 18-65 years of age, meeting DSM-5 criteria for current MDD without psychotic features, a Montgomery-Åsberg Depression Rating Scale (MADRS) total score of at least 25, and CGI-S score of at least 4. Exclusion criteria included: a history of electroconvulsive therapy, vagusnerve stimulation, transcranial magnetic stimulation, or any experimental central nervous system treatment of, during the current episode or in the past 6 months, Schizophrenia, bipolar disorder, obsessive compulsive disorder, and Psychiatric symptoms secondary to any other general medical condition.

Patient demographics and baseline characteristics are shown in Table 6 below:

TABLE 6

|  | 45 mg DM/105 mg BU | Placebo |
|---|---|---|
| Age (years) | 42.1 (12.71) | 41.1 (13.78) |
| Female Gender, n (%) | 98 (60.1%) | 117 (71.3%) |
| Race, n (%) | | |
| White | 88 (54.0%) | 92 (56.1%) |
| Black or African American | 61 (37.4%) | 55 (33.5%) |
| Asian | 9 (5.5%) | 8 (4.9%) |
| Other or Not Reported | 5 (3.1%) | 9 (5.5%) |
| BMI (mg/kg$^2$) | 29.2 (5.59) | 29.4 (5.66) |
| MADRS Total Score | 33.6 (4.43) | 33.2 (4.36) |
| CGI-S Score | 4.6 (0.59) | 4.6 (0.57) |

Data are mean (SD) unless otherwise stated.
Abbreviations:
BMI = Body Mass Index;
BU = Bupropion;
CGI-S = Clinical Global Impression-Severity;
DM = Dextromethorphan;
MADRS = Montgomery-Asberg Depression Rating Scale Demographics and baseline characteristics were similar across both treatment groups. Study completion rates were greater than 75% in both treatment groups.

The primary endpoint of the study was the change from baseline in the MADRS total score at Week 6. Secondary endpoints included MADRS change at Weeks 1 and 2, remission, response, Clinical Global Impression-Improvement (CGI-I), Clinical Global Impression-Severity (CGI-S), Patient Global Impression-Improvement (PGI-I), MADRS-6, Sheehan Disability Scale (SDS), other quality of life measures, safety, and tolerability. P-values were calculated based on least square mean estimates.

DM/BU met the primary endpoint and rapidly and significantly improved symptoms of depression. Specifically, DM/BU demonstrated rapid, durable, and statistically significant improvement in depressive symptoms as measured by MADRS total score compared to placebo (p=0.002 on primary endpoint). DM/BU demonstrated a highly statistically significant reduction in the Montgomery-Åsberg Depression Rating Scale (MADRS) total score compared to placebo at Week 6, with mean reductions from baseline of 16.6 points for DM/BU and 11.9 points for placebo (p=0.002).

Figure 15:
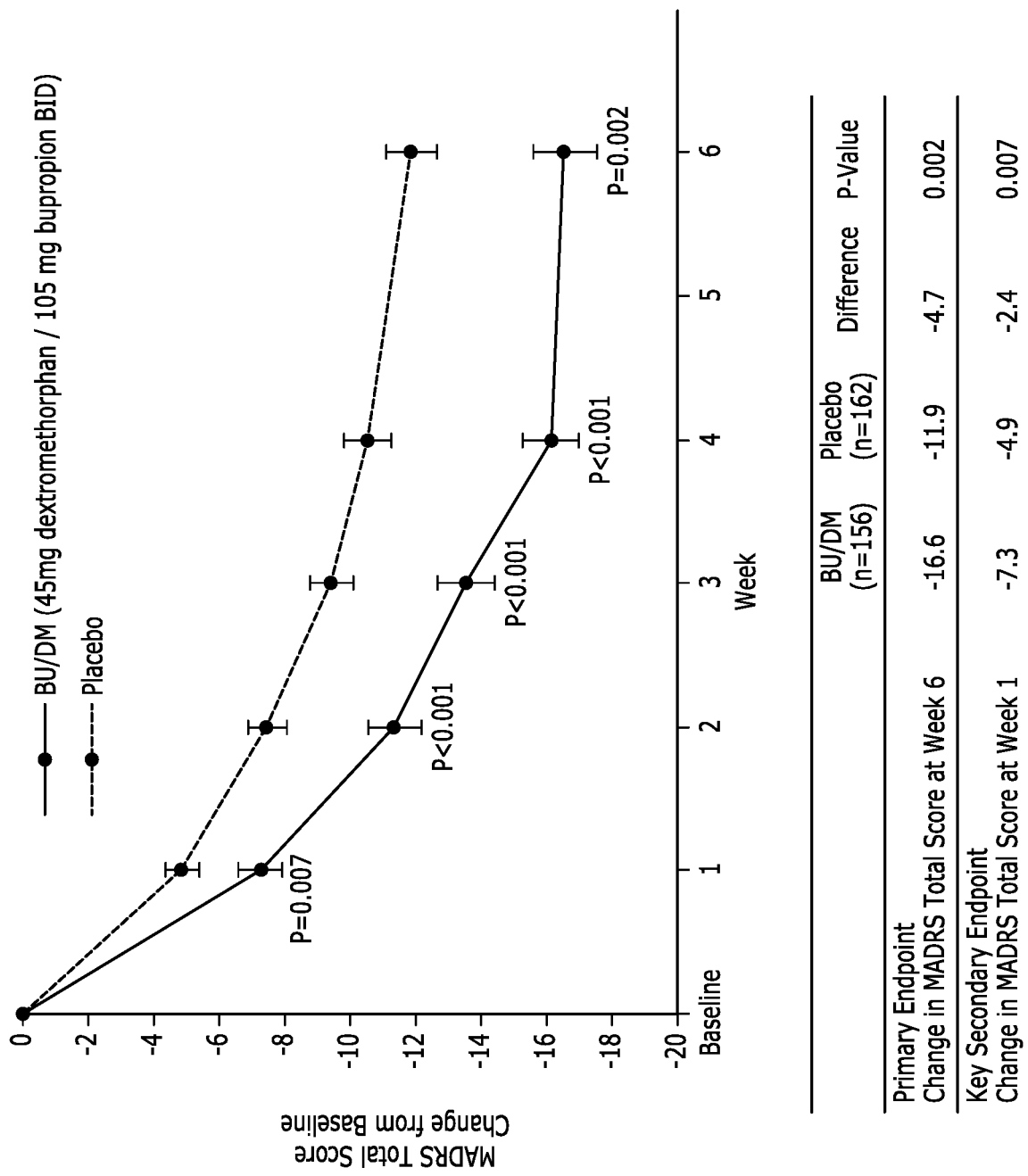
FIG. 15 is a plot of the reduction in MADRS total score over time for the subjects described in Example 6.

Additionally, a statistically significant improvement was observed at Week 1, or only 4 days after the start of twice daily dosing. As depicted in FIG. 15, statistically significant improvements at Week 1 were observed for MADRS total score, with a reduction in MADRS total score of 7.3 points for DM/BU compared to the reduction of 4.9 points for placebo (key secondary endpoint, p=0.007), with statistical significance for this measure maintained at all time points thereafter (e.g., Week 2, 3, 4, 5, or 6). Statistically significant improvements for Patient Global Impression-Improvement (PGI-I) (p=0.008); Clinical Global Impression-Severity (CGI-S) (p=0.013); Clinical Global Impression-Improvement (CGI-I) (p=0.035); Quick Inventory of Depressive Symptomatology-Self-Rated (QIDS-SR-16) (p=0.016); Quality of Life Enjoyment and Satisfaction Questionnaire-Short Form (Q-LES-Q-SF) (p=0.031); and other endpoints were also observed at Week 1 and at every time point thereafter (e.g. Week 2, 3, 4, 5, or 6).

Figure 16:
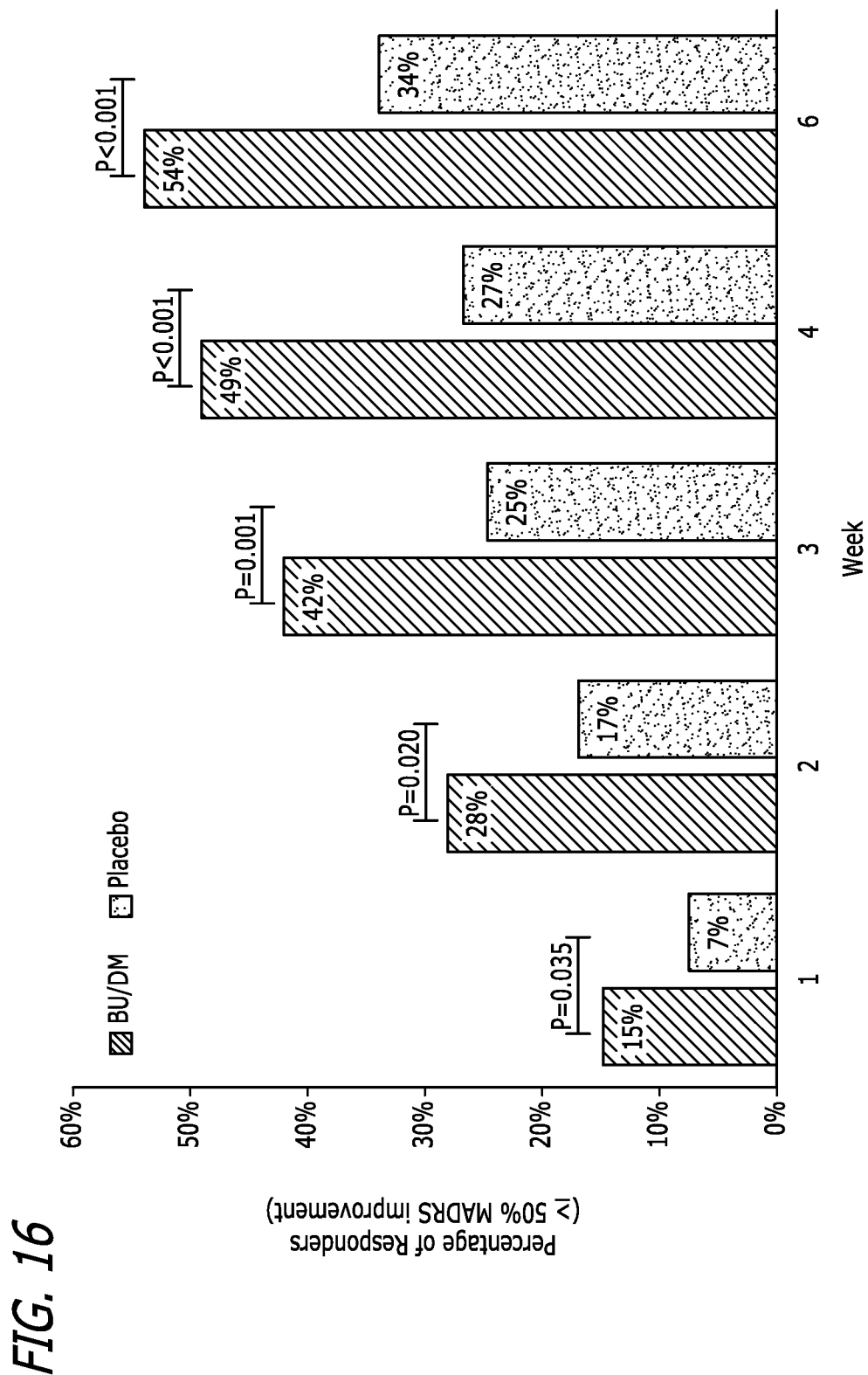
FIG. 16 is a plot of the percentage of responders over time for the subjects described in Example 6.

As shown in FIG. 16, response, defined as a ≥50% improvement in the MADRS total score, was seen at Week 6 in 54.0% of patients who received DM/BU, compared to 34.0% of patients who received placebo (p<0.001).

Figure 17:
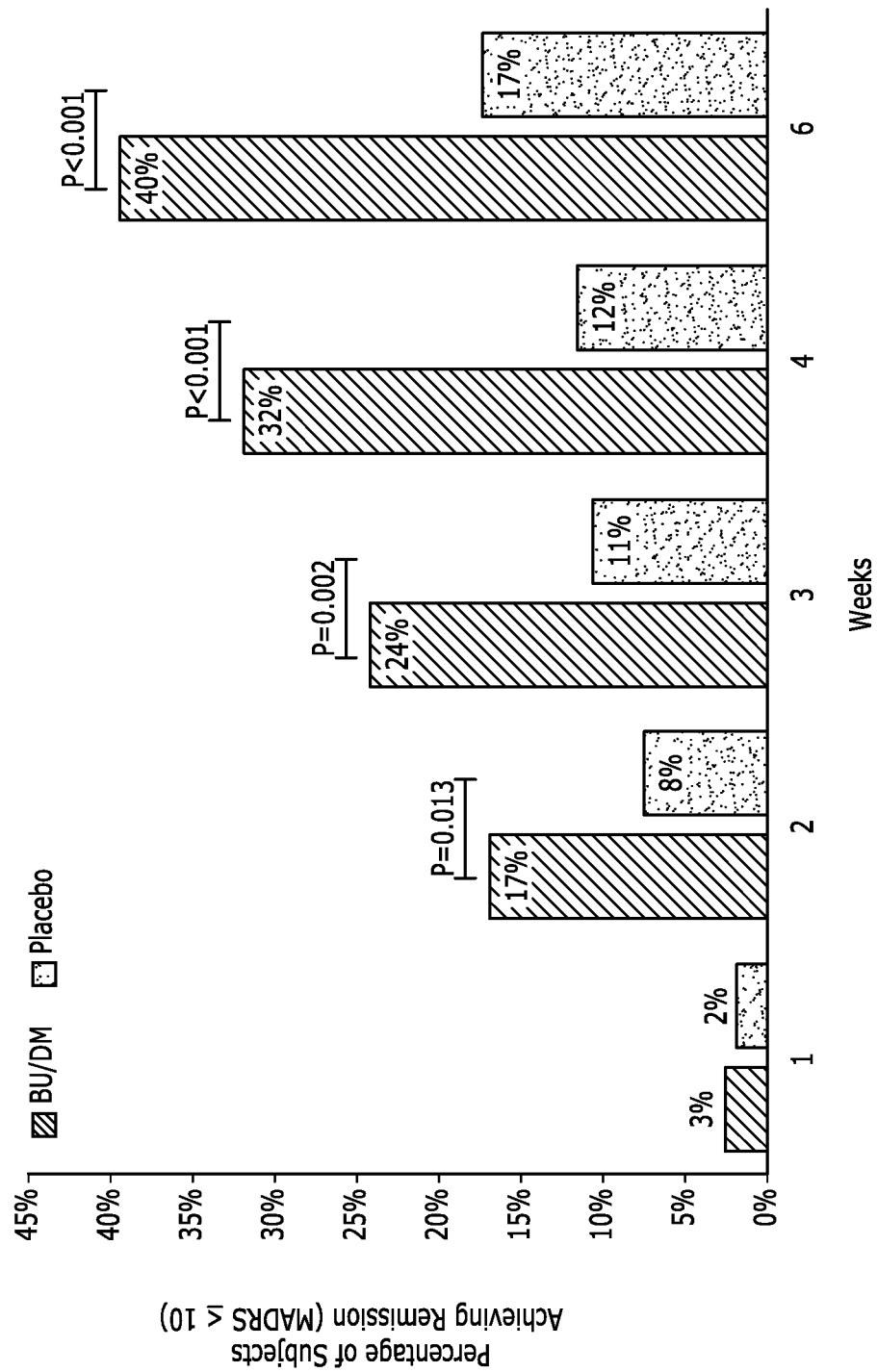
FIG. 17 is a plot of the percentage of subjects in remission over time for the subjects described in Example 6.

As shown in FIG. 17, rates of remission from depression (defined as MADRS≤10) were statistically significantly greater for DM/BU compared to placebo at Week 2 (p=0.013) and at every time point thereafter (e.g., Week 3, 4, or 6), being achieved by 39.5% of DM/BU patients compared to 17.3% of placebo patients at Week 6 (p<0.001).

DM/BU was also associated with a statistically significant reduction in functional impairment, as measured by the Sheehan Disability Scale (SDS), compared to placebo at Week 2 (p=0.003), and at every time point thereafter (p=0.002, at Week 6).

On all secondary endpoints including the following, DM/BU demonstrated statistically significant improvement at Week 6 compared to placebo, reflecting increasing treatment effects over time: clinical response on the MADRS total score (defined as ≥50%) (p<0.001); PGI-I (p=0.007); CGI-S (p=0.002); CGI-I (p=0.016); QIDS-SR-16 (p=0.001); Sheehan Disability Scale (SDS) (p=0.002); and Q-LES-Q-SF (p=0.011).

DM/BU was well tolerated in the phase 3 clinical trial. The most commonly reported adverse events in the DM/BU arm were dizziness, nausea, headache, diarrhea, somnolence, and dry mouth. There was one serious adverse event in the DM/BU arm which was deemed by the investigator not to be study-drug related. The rates of discontinuation due to adverse events were low in both treatment groups (6.2% for DM/BU and 0.6% for placebo). Treatment with DM/BU was not associated with psychotomimetic effects or weight gain.

Example 7

A Phase 3, randomized, double-blind, active controlled trial was conducted to assess the efficacy and safety of DM/BU in the treatment of treatment resistant depression (TRD). Patients with major depressive disorder (MDD) who had previously failed one or two antidepressant treatments were treated in an open-label fashion with 150 mg bupropion twice daily (300 mg total daily dose) (n=799, n represents of number of patients) during a 6-week lead-in period. Patients who failed to respond to bupropion during this lead-in period were randomized in a 1:1 ratio to treatment with bupropion at this same total daily dose (n=156), or to treatment with DM/BU (45 mg dextromethorphan/105 mg bupropion) twice daily (90 mg dextromethorphan/210 mg bupropion total daily dose) (n=156), for 6 weeks. Inclusion criteria for the open-label period included males or females 18-65 years of age, a history of inadequate response to 1 or 2 prior antidepressant treatments, established by the Antidepressant Treatment Response Questionnaire (ATRQ), and a Hamilton Depression Rating Scale (HAMD-17) total score of ≥18. Inclusion criteria for the double-blind period included inadequate response to 2 or 3 prior antidepressant treatments, including open-label period failure. Exclusion criteria included a history of electroconvulsive therapy, vagus nerve stimulation, transcranial magnetic stimulation, or any experimental central nervous system treatment during the current episode or in the past 6 months, schizophrenia, bipolar disorder, obsessive compulsive disorder, psychiatric symptoms secondary to any other general medical condition.

Demographics and baseline characteristics are shown in Table 7 below. Study completion rates were similar across both treatment groups, 89% for dextromethorphan/bupropion and 94% for bupropion.

TABLE 7

Demographics and Baseline Characteristics

|  | Dextromethorphan(45 mg)/Bupropion (105 mg) | Bupropion (150 mg) |
| --- | --- | --- |
| Age (years) | 44.3 (12.19) | 45.1 (12.56) |
| Female Gender, n (%) | 101 (65.6%) | 97 (62.6%) |
| Race, n (%) |  |  |
| White | 100 (64.9%) | 106 (68.4%) |
| Black or African American | 41 (26.6%) | 39 (25.2%) |
| Asian | 2 (1.3%) | 6 (3.9%) |
| Other or Not Reported | 11 (7.1%) | 4 (2.6%) |
| BMI (mg/kg$^2$) | 29.9 (5.85) | 29.5 (5.64) |
| MADRS Total Score | 33.4 (5.61) | 33.2 (5.17) |
| CGI-S Score | 4.6 (0.61) | 4.6 (0.54) |

Data are mean (SD) unless otherwise stated
Abbreviations:
BMI = Body Mass Index;
CGI-S = Clinical Global Impression-Severity;
MADRS = Montgomery-Asberg Depression Rating Scale The change in depressive symptoms over time was measured using the Montgomery-Asberg Depression Rating Scale (MADRS) and the Quick Inventory of Depressive Symptomatology-Self-Rated (QIDS-SR-16). The primary endpoint was the change from baseline in the MADRS after 6 weeks of treatment. The key secondary endpoints were the change from baseline in the MADRS after 1 week of treatment, after 2 weeks of treatment, the average change over entire 6-week double-blind treatment period, and the Sheehan Disability Scale (SDS). Other prespecified secondary efficacy variables included the Cognitive subscale of the Massachusetts General Hospital Cognitive and Physical Functioning Questionnaire (CPFQ), and the Hamilton Anxiety Scale (HAM-A).

Figure 18:
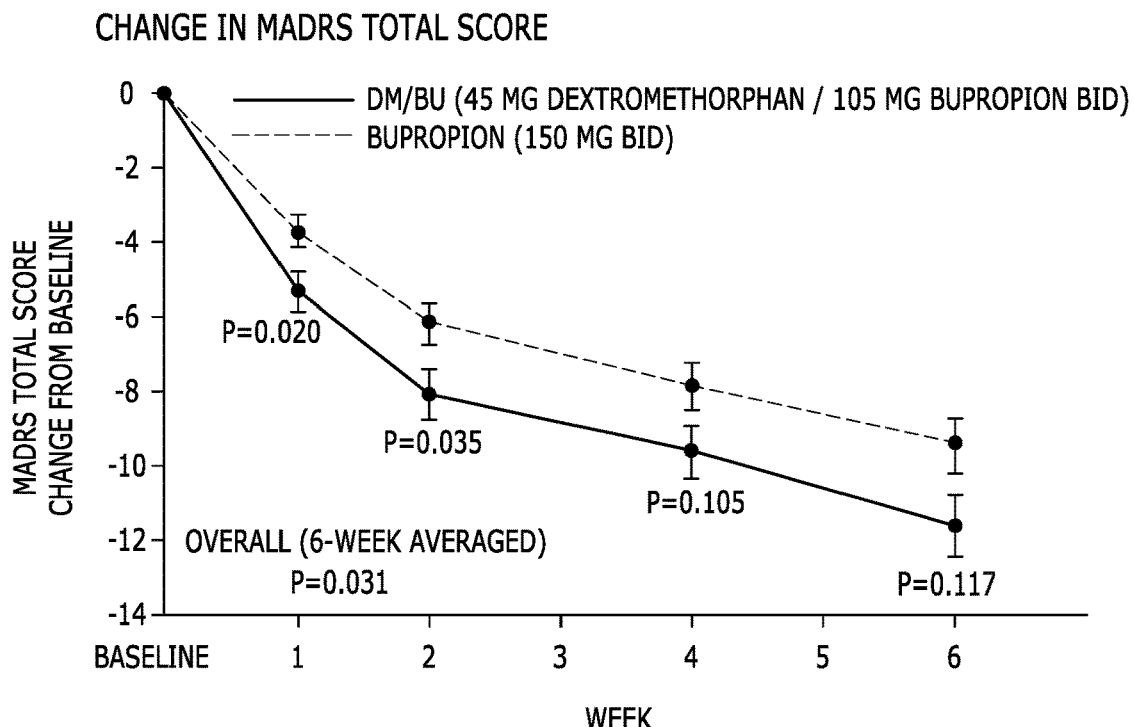
FIG. 18 is a plot of the MADRS total score change from baseline over time for the subjects described in Example 7.

As shown in FIG. 18, DM/BU rapidly and significantly improved symptoms in patients with TRD as measured by MADRS averaged over the entire 6-week treatment period, a key secondary endpoint, with mean reductions of 8.6 for DM/BU (n=154) versus 6.7 for bupropion (n=155) (p=0.031). The rapid onset of action with DM/BU treatment was demonstrated with statistically significant mean MADRS reductions at Week 1, the earliest time point measured, of 5.2 versus 3.6 respectively for DM/BU and bupropion (p=0.02), and at Week 2 of 8.0 versus 6.1 respectively for DM/BU and bupropion (p=0.035), both time points being key secondary endpoints. At Week 6 (primary endpoint), DM/BU demonstrated a numerically greater improvement in MADRS, with mean reductions of 11.6 for DM/BU versus 9.4 for bupropion (p=0.117), but did not reach statistical significance on the Week 6.

Figure 19:
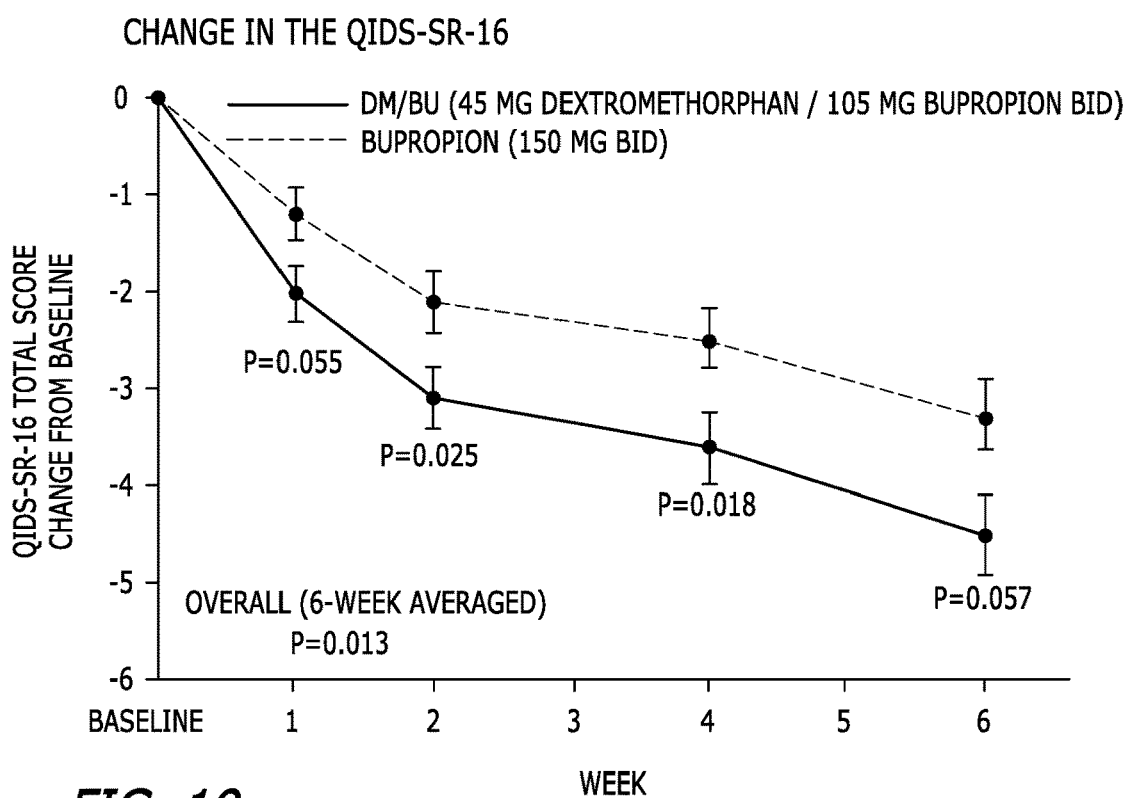
FIG. 19 is a plot of the AIDS-SR-16 total score change from baseline over time for the subjects described in Example 7.

As shown in FIG. 19, DM/BU rapidly and significantly improved depressive symptoms in patients with TRD as measured by the Quick Inventory of Depressive Symptomatology-Self-Rated (QIDS-SR-16) averaged over the entire 6-week treatment period, with mean reductions of 3.3 for DM/BU versus 2.3 for bupropion (p=0.013).

Figure 20:
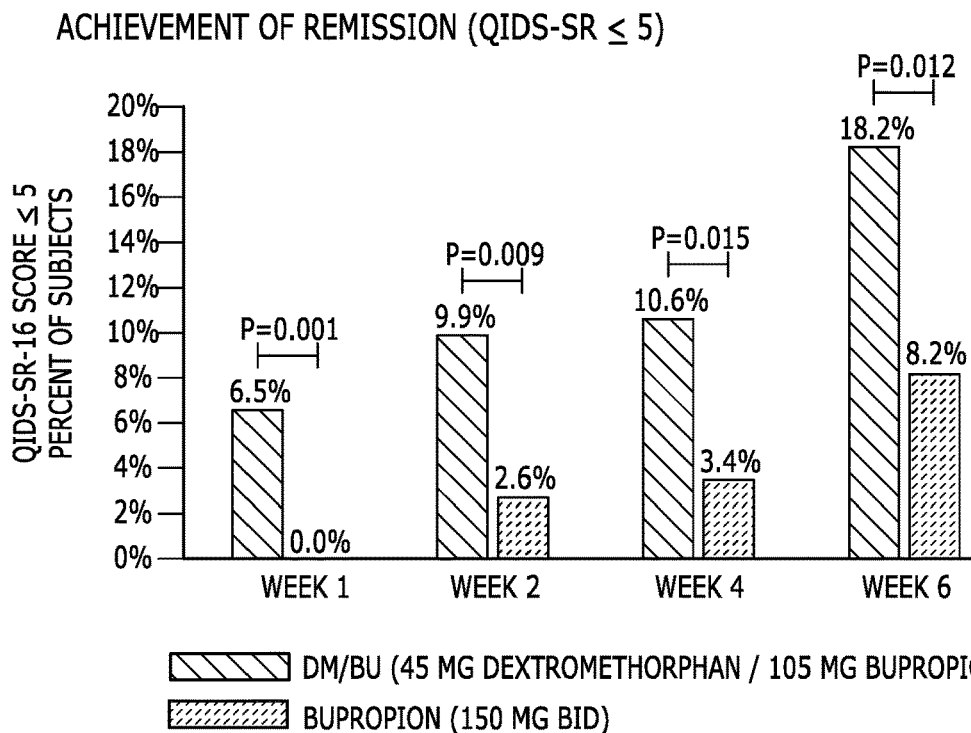
FIG. 20 is a plot of the percentage of subjects in remission (QIDS-SR-16 Score 5) over time for the subjects described in Example 7.

As shown in FIG. 20, rates of remission from depression (defined as QIDS-SR-16≤5) were statistically significantly greater for DM/BU compared to bupropion at Week 1 (p=0.001) and at every time point evaluated thereafter, being achieved by 18.2% of DM/BU patients compared to 8.2% of bupropion patients at Week 6 (p=0.012).

Figure 21:
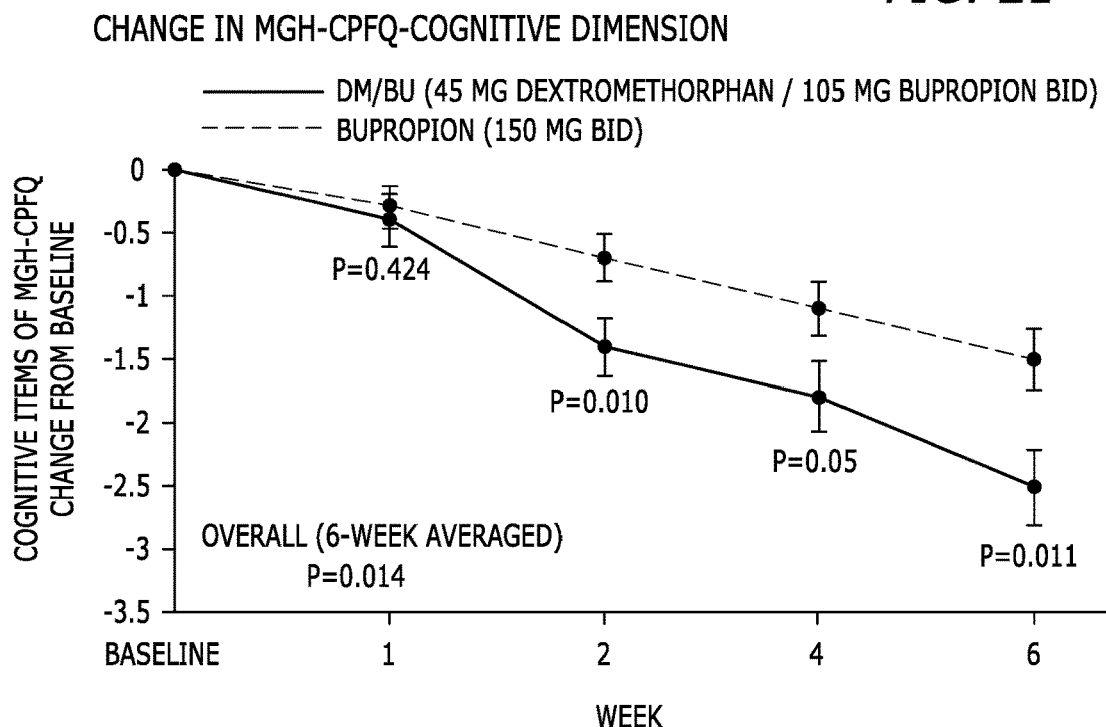
FIG. 21 is a plot of the Cognitive Items of MGH-CPFQ change from baseline over time for the subjects described in Example 7.

As shown in FIG. 21, DM/BU significantly improved cognitive function in patients with TRD as compared to bupropion, assessed using the Cognitive subscale of the Massachusetts General Hospital Cognitive and Physical Functioning Questionnaire (CPFQ) (p=0.011). Cognitive dysfunction is well documented in the different phases of major depression, and plays an important role in functional recovery from major depression. The improvement in cognitive function with DM/BU was rapid as compared to bupropion, reaching statistical significance as early as Week 2 (p=0.01) and at every time point evaluated thereafter. The Cognitive subscale of the CPFQ assesses sharpness/mental acuity, and the ability to focus/maintain attention, to remember/recall information, and to find words. Statistical significance for the superiority of DM/BU versus bupropion was also achieved for the entire CPFQ (p=0.014), which assesses physical in addition to cognitive functioning.

DM/BU rapidly and significantly reduced anxiety symptoms in patients with TRD as compared to bupropion, assessed using the Hamilton Anxiety Scale (HAM-A) (p=0.009). DM/BU demonstrated numerical improvement versus the active comparator bupropion for all other efficacy variables assessed.

DM/BU was well tolerated in the trial. The most commonly reported adverse events in the DM/BU arm were dizziness and nausea. The rates of discontinuation due to adverse events were low in both treatment groups (2.6% for DM/BU and 1.9% for bupropion). There were three serious adverse events in the DM/BU arm, consisting of migraine; overdose; and suicidal ideation, which occurred more than one week after the cessation of treatment. Treatment with DM/BU was not associated with psychotomimetic effects, weight gain, or sexual dysfunction. Adverse events are listed in Table 8 below.

TABLE 8

Treatment-Emergent Adverse Events

| | Double-blind Period[b] | | Open-label Period |
|---|---|---|---|
| | DM/BU (N = 154) | BU (N = 156) | BU (n = 310) |
| AnyTEAE[a] | 67 (43.5%) | 61 (39.1%) | 135 (43.5) |
| Dizziness | 13 (8.4%) | 0 | 9 (2.9%) |
| Nausea | 8 (5.2%) | 3 (1.9%) | 22 (7.1%) |
| Dry mouth | 6 (3.9%) | 3 (1.9%) | 13 (4.2%) |
| Headache | 4 (2.6%) | 7 (4.5%) | 14 (4.5%) |
| Insomnia | 3 (1.9%) | 5 (3.2%) | 19 (6.1%) |
| Constipation | 3 (1.9%) | 3 (1.9%) | 13 (4.2%) |
| Anxiety | 2 (1.3%) | 0 | 11 (3.5%) |
| Irritability | 0 | 2 (1.3%) | 10 (3.2%) |

Abbreviations:
AE = adverse event.
Data presented as number of subjects (% of subjects)
[a]Treatment-emergent AEs occurring in ≥3 subjects during the open-label period or ≥5% of subjects during the double-blind period are reported.
[b]In double-blind period, treatment-emergent AE is defined as any AE with an onset on or after date of randomization and prior to or on visit 9 date or period 2 early termination date.

TABLE 9

Demographics and Baseline Characteristics

| | DM/BU (n = 152) | | Bupropion (n = 49) | | Placebo (n = 156) | |
|---|---|---|---|---|---|---|
| Age (years) | 75.2 | (5.71) | 76.4 | (6.13) | 75.1 | (5.96) |
| Female Gender, n (%) | 86 | (56.6%) | 22 | (44.9%) | 91 | (58.3%) |
| Race, n (%) | | | | | | |
| White | 136 | (89.5%) | 43 | (87.8%) | 128 | (82.1%) |
| Black or African American | 11 | (7.2%) | 5 | (10.2%) | 25 | (16.0%) |
| Asian | 1 | (0.7%) | 0 | | 1 | (0.6%) |
| Other or Not Reported | 4 | (2.6%) | 1 | (2.0%) | 2 | (1.3%) |
| CMAI Score | 60.7 | (17.40) | 66.1 | (19.65) | 59.4 | (15.60) |
| CGI-S (agitation) | 4.2 | (0.77) | 4.4 | (0.82) | 4.2 | (0.65) |
| NPI-A/A Score | 7.2 | (2.17) | 6.9 | (2.45) | 6.8 | (2.07) |
| MMSE | 18.7 | (3.76) | 17.8 | (4.19) | 18.8 | (3.70) | mITT population.
Data are mean (SD) unless otherwise stated.
Abbreviations:
BMI = Body Mass Index;
BU = bupropion;
CGI-S = Clinical Global Impression-Severity;
CMAI = Cohen-Mansfield Agitation Inventory;
DM = dextromethorphan;
mITT = modified intent to treat;
MMSE = Mini-mental state examination;
NPI-A/A = Neuropsychiatric Inventory-Agitation and Aggressive domain.

Example 8

A Phase 2/3 randomized, double-blind, controlled, multicenter, U.S. clinical trial was conducted to evaluate the efficacy and safety of DM/BU in patients with agitation associated with Alzheimer's disease. A total of 366 patients with a diagnosis of probable Alzheimer's disease and clinically meaningful agitation associated with their disease were randomized, initially in a 1:1:1 ratio, to receive DM/BU (dextromethorphan/bupropion, dose escalated from 30 mg/105 mg once daily in the first week, to 30 mg/105 mg twice daily in the second week, to 45 mg/105 mg twice daily thereafter), bupropion (dose escalated from 105 mg once daily in the first week to 105 mg twice daily thereafter), or matching placebo, for 5 weeks. An independent data monitoring committee performed an interim futility analysis and recommended no further randomization to the bupropion arm. Subsequently, patients were randomized in a 1:1 ratio to receive DM/BU or placebo. Total patients randomized were 159, 49, and 158 to the DM/BU, bupropion, and placebo arms, respectively. The mean Cohen-Mansfield Agitation Inventory (CMAI) total scores at baseline were 60.8, 66.1, and 59.3, respectively for the DM/BU, bupropion, and placebo groups. The minimum score on the CMAI is 29, corresponding to the total absence of symptoms, with higher scores corresponding to greater agitation. The primary endpoint of the study was the change from baseline in the CMAI total score at Week 5. P-values were calculated based on least square mean estimates.

Inclusion criteria included male or female 65-90 years of age, diagnosis of probable Alzheimer's disease, according to the 2011 NIA-AA criteria, diagnosis of agitation, according to the IPA provisional definition of agitation, MMSE score between 10 and 24, an NPI-AA score 4, and community dwelling. Exclusion criterial included dementia of non-Alzheimer's type and current use of a selective serotonin reuptake inhibitor and/or a serotonin and norepinephrine inhibitor (SSRI/SNRI). Demographics and baseline characteristics are shown in Table 9 below.

Figure 22:
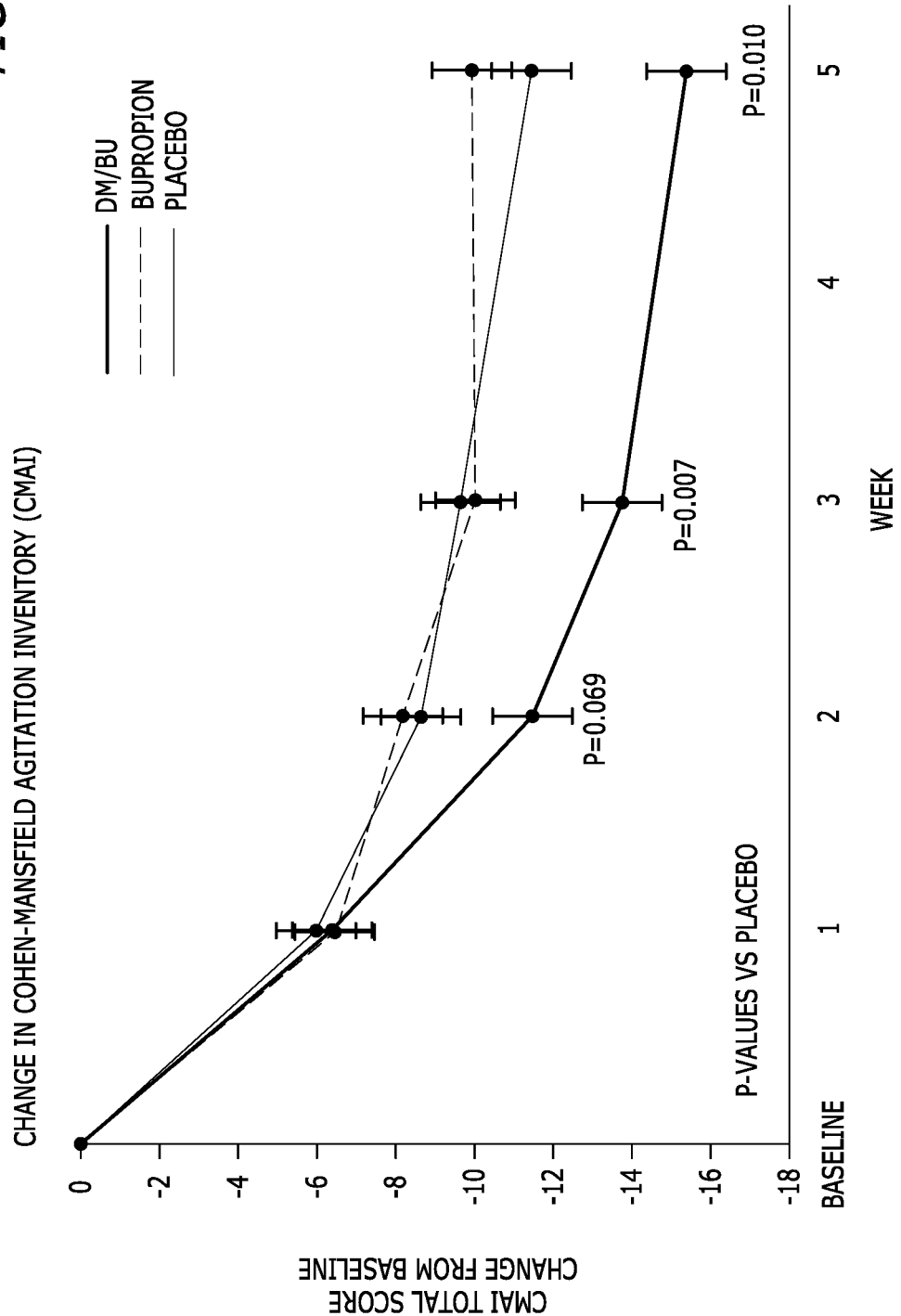
FIG. 22 is a plot of the CMAI total score change from baseline over time for the subjects described in Example 8.

As shown in FIG. 22, DM/BU met the primary endpoint by demonstrating a statistically significant mean reduction in the Cohen Mansfield Agitation Inventory (CMAI) total score compared to placebo at Week 5, with mean reductions from baseline of 15.4 points for DM/BU (n=152), 10.0 for BU 9n=49), and 11.5 points for placebo (n=156) (p=0.010).

Figure 23:
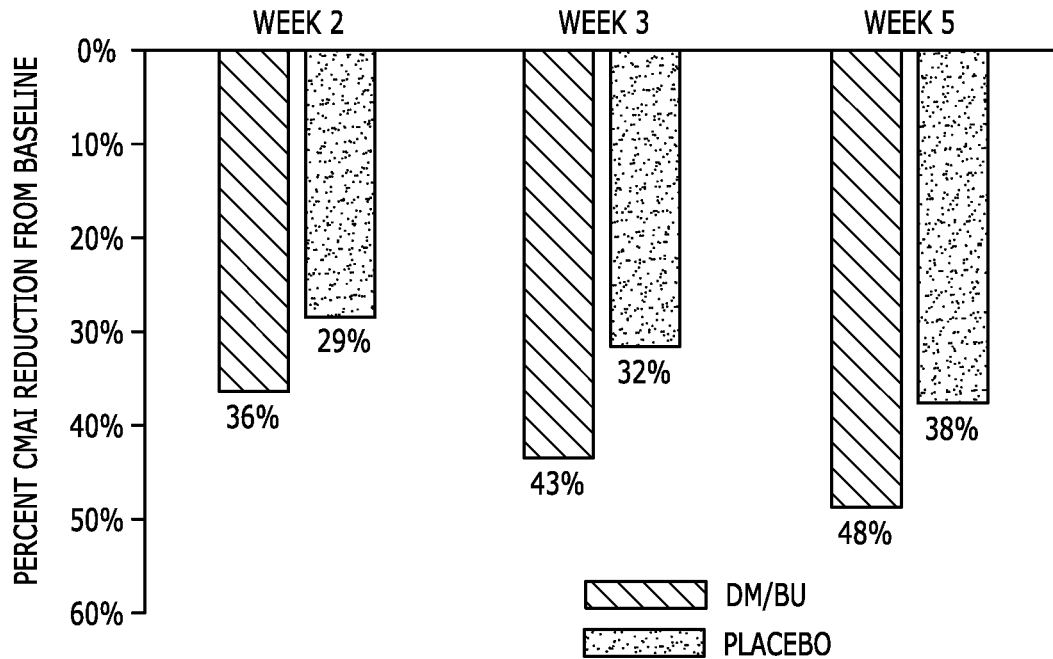
FIG. 23 is a plot of the percent CMAI reduction from baseline over time for the subjects described in Example 8.

As shown in FIG. 23, These results represent a mean percentage reduction of CMAI from baseline of 48% for DM/BU versus 38% for placebo. The CMAI is a 29-item caregiver-rated scale that assesses the frequency of agitation-related behaviors in patients with dementia, including excessive motor activity such as pacing and restlessness, verbal aggression such as screaming and shouting, and physical aggression such as grabbing, pushing, and hitting. DM/BU was also statistically superior to bupropion on the CMAI total score (p<0.001) at week 5, demonstrating component contribution.

DM/BU rapidly improved agitation symptoms. DM/BU numerically separated from placebo at Week 2 with a mean reduction from baseline in the CMAI total score of 11.5 points for DM/BU compared to 8.7 points for placebo (p=0.069).

DM/BU demonstrated a statistically significant mean reduction from baseline in the CMAI total score of 13.8 points for DM/BU compared to 9.7 points for placebo at Week 3 (p=0.007), with statistical significance for this measure maintained thereafter.

Figure 24:
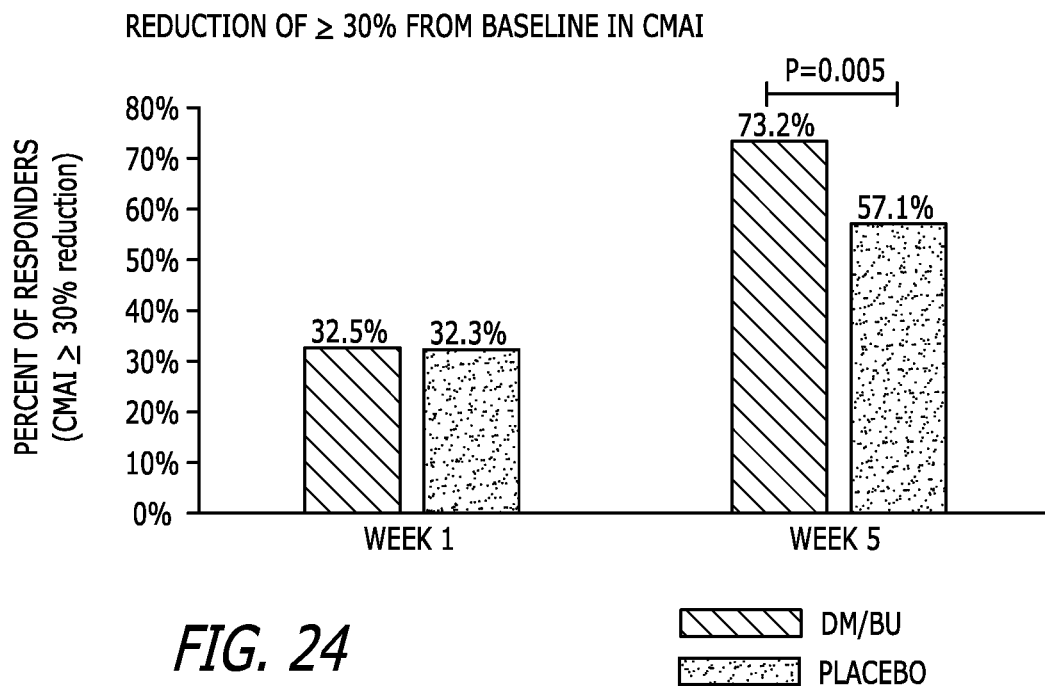
FIG. 24 is a plot of is a plot of the percentage of responders with CMAI reduction 30% from baseline over time for the subjects described in Example 8.

As shown in FIG. 24, a statistically significantly greater proportion of patients achieved a clinical response on the CMAI, defined as a 30% or greater improvement from baseline, with DM/BU as compared to placebo (73% versus 57%, p=0.005). These results were consistent with clinicians' global assessments of change measured using the modified Alzheimer's Disease Cooperative Study-Clinical Global Impression of Change for Agitation (mADCS-CGIC). DM/BU demonstrated statistically significantly greater improvement in agitation as compared to placebo on this measure (p=0.036).

treatments in the current major depressive episode prior to being treated with a combination of 45 mg of dextromethorphan hydrobromide and 105 mg of bupropion hydrochloride, given twice a day. Preliminary results for the ongoing study are depicted in Table 11 below.

TABLE 11

|  | Baseline | Week 1 | Week 2 | Week 4 | Week 6 | Week 8 | Week 12 |
| --- | --- | --- | --- | --- | --- | --- | --- |
| MADRS | 33.28 | 23.11 | 18.28 | 14.58 | 9.20 | 9.11 | 11.15 |
| MADRS Change from BL |  | −10.2 | −15.2 | −18.7 | −24.1 | −24.0 | −22.2 |

DM/BU was safe and well tolerated in the trial. The most commonly reported adverse events in the DM/BU arm were somnolence (8.2% for DM/BU versus 4.1% for bupropion and 3.2% for placebo), dizziness (6.3%, 10.2%, 3.2%, for DM/BU, bupropion, and placebo arms respectively), and diarrhea (4.4%, 6.1%, 4.4%, for DM/BU, bupropion, and placebo arms respectively). The rates of discontinuation due to adverse events were 1.3%, 2.0%, and 1.3% in the DM/BU, bupropion, and placebo arms, respectively. Serious adverse events were reported in 3.1% of patients treated with DM/BU, compared to 8.2% of bupropion, and 5.7% of placebo-treated patients. No serious adverse events were deemed to be related to study drug in any treatment arm. There was one death in the placebo arm, one in the bupropion arm, and none in the DM/BU arm. There was no evidence of cognitive decline for patients treated with DM/BU as shown by the Mini-Mental State Examination (MMSE), a widely utilized measure of general cognitive function. Treatment with DM/BU was not associated with sedation. Adverse events are listed in Table 10 below.

TABLE 10

Treatment-Emergent Adverse Event

|  | DM/BU (n = 159) | Bupropion (n = 49) | Placebo (n = 158) |
| --- | --- | --- | --- |
| Subjects with any TEAE | 70 (44.0%) | 30 (61.2%) | 52 (32.9%) |
| Somnolence | 13 (8.2%) | 2 (4.1%) | 5 (3.2%) |
| Dizziness | 10 (6.3%) | 5 (10.2%) | 5 (3.2%) |
| Diarrhea | 7 (4.4%) | 3 (6.1%) | 7 (4.4%) |
| Headache | 6 (3.8%) | 3 (6.1%) | 5 (2.5%) |
| Falls | 4 (2.5%) | 7 (14.3%) | 3 (1.9%) |
| Fatigue | 3 (1.9%) | 5 (10.2%) | 2 (1.3%) |
| Insomnia | 1 (0.6%) | 3 (6.1%) | 3 (1.9%) |
| Serious AEs | 5 (3.1%) | 4 (8.2%) | 9 (5.7%) |
| Discontinuation due to AEs | 2 (1.3%) | 1 (2.0%) | 2 (1.3%) |
| Deaths | 0 | 1 (2.0%) | 1 (0.6%) |

Abbreviations:
AE = adverse event;
TEAE = Treatment-emergent adverse event.
Safety Population, data presented as number of subjects (% of subjects).
Treatment-emergent AEs occurring in ≥5% of subjects in any treatment group are presented.

Example 9

An open label study was started with 47 patients having major depressive disorder who had received two or more Example 10

The open label study of Example 9 was continued. A total of 70 patients were enrolled who had ongoing symptoms of depression despite receiving treatment with two or more prior antidepressants during the current major depressive episode. Patients were treated with a 45 mg dextromethorphan-105 mg bupropion modulated delivery tablet twice daily for up to 12 months. The results are summarized in Table 12.

TABLE 12

| Timepoint | MADRS Reduction |
| --- | --- |
| Baseline | 0 |
| 1 week | −10.4 |
| 2 weeks | −14.7 |
| 6 weeks | −20.6 |
| 6 months | −22.9 |
| 1 year | −26.3 |

MADRS Reduction: mean reduction of MADRS score from baseline.

Figure 25:
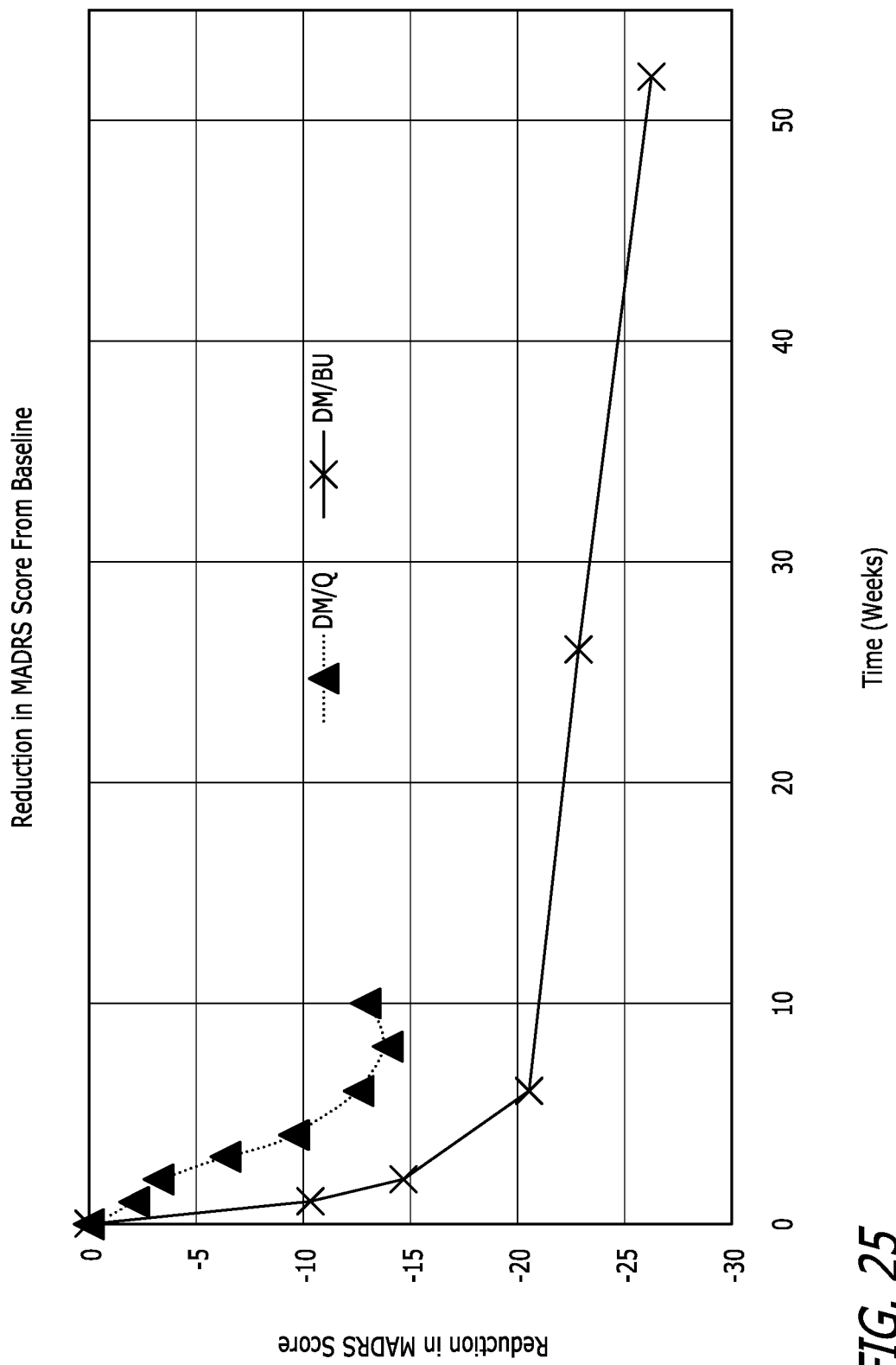
FIG. 25 depicts the reduction in MADRS Score from baseline from the clinical trial of DM/BU in Example 10 as compared to the combination of dextromethorphan and quinidine (DM/Q) as reported in Murrough (Journal of Affective Disorders 218 (2017) 277-283, FIG. 3A).

FIG. 25 depicts the reduction in MADRS Score from baseline from this trial DM/BU as compared to the combination of dextromethorphan and quinidine (DM/Q) as reported in Murrough (Journal of Affective Disorders 218 (2017) 277-283, FIG. 3A).

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating depression while reducing the risk of an adverse event associated with treatment with bupropion, comprising orally administering a daily dose of bupropion that is about 200 mg to about 250 mg of bupropion hydrochloride, or a molar equivalent amount of bupropion in another salt form or the free base form, and a daily dose of dextromethorphan that is about 80 mg to about 100 mg of dextromethorphan hydrobromide, or a molar equivalent amount of dextromethorphan in another salt form or the free base form, to a human being in need thereof for at least 8 consecutive days, wherein the daily dose of the bupropion and the dextromethorphan achieves the same or an improved therapeutic effect in treating depression as compared to administering a higher daily dose of bupropion alone, thereby reducing the risk of the adverse event associated with treatment with bupropion.

2. The method of claim 1, wherein about 105 mg of bupropion hydrochloride is orally administered twice a day to the human being.

3. The method of claim 2, wherein about 45 mg of dextromethorphan hydrobromide is orally administered twice a day to the human being.

4. The method of claim 1, wherein the adverse event is headache.

5. The method of claim 1, wherein the adverse event is insomnia.

6. The method of claim 1, wherein the adverse event is irritability.

7. The method of claim 1, wherein the adverse event is nausea.

8. The method of claim 1, wherein the adverse event is anxiety.

9. The method of claim 1, wherein the adverse event is weight gain.

10. The method of claim 1, wherein the adverse event is seizure.

11. The method of claim 1, wherein the human being is suffering from major depressive disorder.

12. The method of claim 1, wherein the human being is suffering from treatment-resistant major depressive disorder.

13. A method of treating depression while reducing the risk of an adverse event associated with treatment with bupropion, comprising orally administering a combination of bupropion that is about 70 mg to about 95 mg of the bupropion free base, or a molar equivalent amount of bupropion in a salt form, and dextromethorphan that is about 30 mg to about 42 mg of the dextromethorphan free base, or a molar equivalent amount of dextromethorphan in a salt form, to a human being in need thereof once a day or twice a day for at least 8 consecutive days, wherein administering the combination of the bupropion and the dextromethorphan achieves the same or an improved therapeutic effect in treating depression as compared to administering a higher molar equivalent amount of bupropion alone, thereby reducing the risk of the adverse event associated with treatment with bupropion.

14. The method of claim 13, wherein the adverse event is headache.

15. The method of claim 13, wherein the adverse event is insomnia.

16. The method of claim 13, wherein the adverse event is irritability.

17. The method of claim 13, wherein the adverse event is nausea.

18. The method of claim 13, wherein the adverse event is anxiety.

19. The method of claim 13, wherein the adverse event is weight gain.

20. The method of claim 13, wherein the adverse event is seizure.

21. The method of claim 13, wherein the human being is suffering from major depressive disorder.

22. The method of claim 13, wherein the human being is suffering from treatment-resistant major depressive disorder.

* * * * *